(12) United States Patent
Rinaldi et al.

(10) Patent No.: US 11,707,524 B2
(45) Date of Patent: Jul. 25, 2023

(54) LIQUID PHARMACEUTICAL COMPOSITION

(71) Applicant: Fresenius Kabi Deutschland GmbH, Bad Homburg (DE)

(72) Inventors: Gianluca Rinaldi, Monterotondo (IT); Silvia Fratarcangeli, Ceprano (IT); Alessandra Del Rio, Rome (IT)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 17/198,983

(22) Filed: Mar. 11, 2021

(65) Prior Publication Data

US 2021/0196824 A1  Jul. 1, 2021

Related U.S. Application Data

(63) Continuation of application No. 16/943,086, filed on Jul. 30, 2020, now abandoned, which is a (Continued)

(30) Foreign Application Priority Data

May 23, 2014  (EP) .................................. 14169753

(51) Int. Cl.
*A61K 39/395* (2006.01)
*A61K 9/00* (2006.01)
(Continued)

(52) U.S. Cl.
CPC ...... *A61K 39/39591* (2013.01); *A61K 9/0019* (2013.01); *A61K 9/19* (2013.01);
(Continued)

(58) Field of Classification Search
None
See application file for complete search history.

(56) References Cited

U.S. PATENT DOCUMENTS

| | | |
|---|---|---|
| 5,900,404 A | 5/1999 | Gegg et al. |
| 6,090,382 A | 7/2000 | Salfeld et al. |

(Continued)

FOREIGN PATENT DOCUMENTS

| | | |
|---|---|---|
| CN | 104707146 A | 6/2015 |
| EP | 3085385 A1 | 10/2016 |

(Continued)

OTHER PUBLICATIONS

Shire SJ, Shahrokh Z, Liu J. Challenges in the development of high protein concentration formulations. J Pharm Sci. Jun. 2004;93(6):1390-402. doi: 10.1002/jps.20079. PMID: 15124199. (Year: 2004).*

(Continued)

*Primary Examiner* — Michelle S Horning
(74) *Attorney, Agent, or Firm* — Goodwin Procter LLP

(57) ABSTRACT

The present invention relates to novel liquid pharmaceutical compositions of adalimumab, which include adalimumab or a biosimilar thereof, an acetate buffering agent/system such as sodium acetate/acetic acid, and a sugar stabiliser such as trehalose. Such a combination of components furnishes formulations having a stability (e.g. on storage and when exposed to stress) which is comparable to or an improvement upon those known in the art, and with fewer ingredients. Such advances will help adalimumab treatments to become more widely available at lower cost, and prolong the viability of pre-loaded delivery devices (e.g. pre-filled syringes) to reduce unnecessary waste of the drug.

11 Claims, 11 Drawing Sheets

Related U.S. Application Data continuation of application No. 16/584,399, filed on Sep. 26, 2019, now Pat. No. 10,729,769, which is a continuation of application No. 15/313,470, filed as application No. PCT/EP2015/060816 on May 15, 2015, now Pat. No. 10,426,832.

(51) Int. Cl.

| | | |
|---|---|---|
| A61K 47/26 | (2006.01) | |
| C07K 16/24 | (2006.01) | |
| A61K 9/19 | (2006.01) | |
| A61K 47/02 | (2006.01) | |
| A61K 47/12 | (2006.01) | |
| A61K 39/00 | (2006.01) | |

(52) U.S. Cl.
CPC .............. *A61K 47/02* (2013.01); *A61K 47/12* (2013.01); *A61K 47/26* (2013.01); *C07K 16/241* (2013.01); *A61K 2039/505* (2013.01); *A61K 2039/54* (2013.01); *C07K 2317/21* (2013.01); *C07K 2317/76* (2013.01)

(56) References Cited

U.S. PATENT DOCUMENTS

| | | | |
|---|---|---|---|
| 6,171,586 | B1 | 1/2001 | Lam et al. |
| 8,420,081 | B2 | 4/2013 | Fraunhofer et al. |
| 8,802,101 | B2 | 8/2014 | Krause et al. |
| 9,861,695 | B2 | 1/2018 | Manning et al. |
| 10,155,039 | B2 | 12/2018 | Manning et al. |
| 10,426,832 | B2 | 10/2019 | Rinaldi et al. |
| 10,426,833 | B2 | 10/2019 | Rinaldi et al. |
| 10,493,152 | B2 | 12/2019 | Rinaldi et al. |
| 10,716,852 | B2 | 7/2020 | Manning et al. |
| 10,729,769 | B2 | 8/2020 | Rinaldi et al. |
| 10,772,961 | B2 | 9/2020 | Rinaldi et al. |
| 10,980,881 | B2 * | 4/2021 | Lee .................... A61K 9/0019 |
| 2004/0033228 | A1 | 2/2004 | Krause et al. |
| 2009/0130119 | A1 | 5/2009 | Abate et al. |
| 2009/0291062 | A1 | 11/2009 | Fraunhofer et al. |
| 2010/0137213 | A1 | 6/2010 | Fernandez et al. |
| 2010/0278822 | A1 | 11/2010 | Fraunhofer et al. |
| 2011/0300135 | A1 | 12/2011 | Lobo et al. |
| 2013/0243764 | A1 | 9/2013 | Ellis et al. |
| 2014/0086930 | A1 | 3/2014 | Krause et al. |
| 2014/0086931 | A1 | 3/2014 | Krause et al. |
| 2014/0141007 | A1 | 5/2014 | Fraunhofer et al. |
| 2014/0186361 | A1 * | 7/2014 | Manning ................. A61P 9/10 424/142.1 |
| 2014/0314781 | A1 | 10/2014 | Krause et al. |
| 2017/0182162 | A1 | 6/2017 | Rinaldi et al. |
| 2017/0189527 | A1 | 7/2017 | Rinaldi et al. |
| 2017/0196974 | A1 | 7/2017 | Rinaldi et al. |
| 2020/0155677 | A1 | 5/2020 | Rinaldi et al. |
| 2021/0308262 | A1 | 10/2021 | Rinaldi et al. |
| 2021/0322551 | A1 | 10/2021 | Rinaldi et al. |

FOREIGN PATENT DOCUMENTS

| | | |
|---|---|---|
| IN | 610/MUM/2012 | 11/2013 |
| IN | 1606/MUM/2012 | 11/2013 |
| IN | 3031/MUM/2012 | 11/2013 |
| IN | 1248/MUM/2014 | 4/2014 |
| JP | S63-88197 A | 4/1988 |
| WO | WO-1997/029131 A1 | 8/1997 |
| WO | WO-2004/091658 A1 | 10/2004 |
| WO | WO-2005/072772 A1 | 8/2005 |
| WO | WO-2006/012500 A2 | 2/2006 |
| WO | WO-2006/044908 A2 | 4/2006 |
| WO | WO-2006/131013 A2 | 12/2006 |
| WO | WO-2009/073569 A2 | 6/2009 |
| WO | WO-2009/076105 A2 | 6/2009 |
| WO | WO-2010/129469 A1 | 11/2010 |
| WO | WO-2011/104381 A2 | 9/2011 |
| WO | WO-2011/109365 A2 | 9/2011 |
| WO | WO-2011/119487 A2 | 9/2011 |
| WO | WO-2011/161226 A2 | 12/2011 |
| WO | WO-2012/065072 A2 | 5/2012 |
| WO | WO-2012/089778 A1 | 7/2012 |
| WO | WO-2012/121754 A1 | 9/2012 |
| WO | WO-2013/006454 A1 | 1/2013 |
| WO | WO-2013/011076 A2 | 1/2013 |
| WO | WO-2013/164837 A1 | 11/2013 |
| WO | WO-2013/186230 A1 | 12/2013 |
| WO | WO-20 14/039903 A2 | 3/2014 |
| WO | WO-2014/066468 A1 | 5/2014 |
| WO | WO-2014/068021 A1 | 5/2014 |
| WO | WO-2014/068026 A1 | 5/2014 |
| WO | WO-2014/068029 A1 | 5/2014 |
| WO | WO-2014/071212 A1 | 5/2014 |
| WO | WO-2015/151115 A1 | 10/2015 |
| WO | WO-2015/177058 A1 | 11/2015 |
| WO | WO-2015/177059 A1 | 11/2015 |

OTHER PUBLICATIONS

"Highlights of Prescribing Information" for Humira® Dec. 6, 2018, AbbVie, Inc., North Chicago, IL, USA.

Andya et al., (1996), "The effect of sugars and buffer excipients on the stabilization of a lyophilized formulation for an anti-IgE humanized monoclonal antibody," Pharmaceutical Research (New York) 13(9 Suppl): S78.

Bedu-Addo et al., (2002), "Preformulation development of recombinant pegylated staphylokinase SY161 using statistical design," *AAPS PharmSci*. 4(4):E19.

Bedu-Addo et al., (2004), Pharmaceutical Technology Lyophilization: Understanding Lyophilization Formulation Development pp. 10-18.

Bender (2013), "Alternative buffers for pharmaceutical anti-TNFalpha monoclonal antibody formulations" (10 pages).

Cavatur et al., "Crystallization behavior of mannitol in frozen aqueous solutions", Pharm Res, Jun. 2002; 19(6): 894-900.

Decision in *Amgen, Inc. v. Abbvie Biotechnology Ltd.*, IPR2015-01514, U.S. Pat. No. 8,916,157, Paper 9, (PTAB, Jan. 14, 2015).

Decision in *Amgen, Inc. v. Abbvie Biotechnology Ltd.*, IPR2015-01517, U.S. Pat. No. 8,916,158, Paper 9, (PTAB, Jan. 14, 2016).

European Medicines Agency Assessment Report for Simponi (golimumab), 2009, (70 pages).

Fransson and Espander-Jansson, "Local tolerance of subcutaneous injections", J Pharm Pharmacol, 1996; 48(10): 1012-5.

Frenken et al., "Identification of the Component Part in an Epoeitn Alfa Preparation That Causes Pain After Subcutaneous Injection", American Journal of Kidney Diseases, vol. 22, No. 4, Oct. 1993, (553-556).

Harries and Rosgen, (2008) "A Practical Guide on HowOsmolytes Modulate Macromolecular Properties," Chapter 22 in Methods in Cell Biology, vol. 86, Elsevier, Inc. (57 pages).

Hawe, et al., "Fluorescent molecular rotors as dyes to characterize polysorbate-containing IgG formulations", Pharm Res. Feb. 2010; 27(2): 314-26.

Hovgaard et al., eds., (2013), "Pharmaceutical Formulation Development of Peptides and Proteins, 2nd Edition," CRC Press, p. 155, 8.2.1. "Buffers" (2 pages).

Humira (adalimumab): Prescribing Information (2003), Abbot Laboratories, North Chicago, IL (13 pages).

Humira (adalimumab): Prescribing Information (2014), AbbVie, Inc., North Chicago, IL. (80 pages).

International Search Report for International Patent Application No. PCT/EP2015/060816 dated Jun. 24, 2015 (3 pages).

Jain and Roy, "Trehalose and Protein Stability", Current Protocols in Protein Science, Feb. 2010; Chapter 4:Unit 4.6 (4 pages).

Jeong (2012) "Analytical Methods and Formulation Factors to Enhance Protein Stability in Solution," Archives of Pharmacal Research, 35(11):1871-1886.

Laursen et al., "Pain perception after subcutaneous injections of media containing different buffers", Basic Clin Pharmacol Toxicol, Feb. 2006; 98(2): 218-21.

(56) References Cited

OTHER PUBLICATIONS

Matheus et al., "A critical evaluation of Tm(FTIR) measurements of high-concentration IgG1 antibody formulations as a formulation development tool", Pharm Res. Jul. 2006; 23(7): 1617-27.
Mensink et al., (2017) "How Sugars Protect Proteins in the Solid State and During Drying (Review): Mechanisms of Stabilization In Relation to Stress Conditions", Eur. J. Pharm. Biopharm., 114:288-295.
Piedmonte et al., "Sorbitol crystallization can lead to protein aggregation in frozen protein formulations", Pharm Res., Jan. 2007; 24(1): 136-46.
Rathore and Rajan, "Current perspectives on stability of protein drug products during formulation, fill and finish operations", Biotechnol Prog, May-Jun. 2008; 245(3):504-14.
Response filed Apr. 16, 2014, in U.S. Appl. No. 14/091,938 (US 2014/00886931).
Ruzin, "Plant Microtechnique and Microscopy", New York Oxford Press, 1999 (14 pages).
Saito, "Development of a genral Strategy for formulation optimizatoin of therapeutic monoclonal antiboides", Osaka Unversitey Knowledge Archive, Jul. 2013 (123 pages).
Sharma et al., (2009) "The Formulation and Delivery of Monoclonal Antibodies", Chapter 30 (pp. 675-709) in Therapeutic Monoclonal Antibodies: From Bench to Clnic, Zhiqiang An, Ed., John Wiley & Sons, Inc.
Shire et al., (2004), "Challenges in the development of high protein concentration formulations", J. Pharm. Sci.; 93(6):1390-402.
Sigma-Aldrich, www.sigmaaldrich.com/life-science/core-bioreagentsjbiological-buffers/learning-center/buffer-reference-center.html (publication date: Apr. 23, 2014) (4 pages).
Simponi: Highlights of Prescribing Information (2009), Centocor Ortho Biotech, Inc., Horsham, PA (47 pages).
Singh et al., "Best Practices for formulation and manufacturing of biotech drug products", Biopharm International, Jun. 2009; 22(6): 32-48.
Wang , (1999), "Instability, stabilization, and formulation of liquid protein pharmaceuticals", *International Journal of Pharmaceutics*, 185:129-188.
Wang et al., (2007), "Antibody Structure, Instability, and Formulation", *Journal of Pharmaceutical Sciences*, 96(1):1-26.
Warne, (2010), "Formulation Development of Phase 1-2 biopharmaceuticals: an efficient and timely approach", Chapter 6 in Formulation and Process Development Strategies for Manufacturing Biopharmaceuticals, Jameel and Hershenson, eds., John Wiley & Sons, Inc. (14 pages).
Warne, Development of high concentration protein biopharmaceuticals: the use of platform approaches in formulation development, Eur. J. Phar. Biopharm. Jun. 2011; 78(2): 208-12.
Written Opinion of the International Searching Authority for International Patent Application No. PCT/EP2015/0060816 dated Jun. 24, 2015 (5 pages).
Zhou et al., (2012) "Investigation of freeze/thaw-related quality attributes of a liquid biopharmaceutical formulation: the role of saccharide excipients", PDA J Pharm Sci Technol. May-Jun;66(3):221-35.
U.S. Appl. No. 15/313,470 (U.S. Pat. No. 10,426,832), filed Nov. 22, 2016, Rinaldi et al., Liquid Pharmaceutical Composition.
U.S. Appl. No. 16/584,399 (U.S. Pat. No. 10,729,769), filed Sep. 26, 2019, Rinaldi et al., Liquid Pharmaceutical Composition .
U.S. Appl. No. 16/943,086, filed Jul. 30, 2020, Rinaldi et al., Liquid Pharmaceutical Composition.
U.S. Appl. No. 17/069,118, filed Oct. 13, 2020, Rinaldi et al., Liquid Pharmaceutical Composition.
U.S. Appl. No. 15/313,480 (U.S. Pat. No. 10,493,152, filed Nov. 22, 2016, Rinaldi et al., Adalimumab Formulations.
U.S. Appl. No. 16/694,627 (U.S. Pat. No. 10,772,961), filed Nov. 25, 2019, Rinaldi et al., Liquid Pharmaceutical Composition.
U.S. Appl. No. 16/990,954, filed Aug. 11, 2020, Rinaldi et al., Liquid Pharmaceutical Composition.
U.S. Appl. No. 15/313,487 (U.S. Pat. No. 10,426,833), filed Nov. 22, 2016, Rinaldi et al., Liquid Pharmaceutical Composition.
U.S. Appl. No. 16/584,418, filed Sep. 26, 2019, Rinaldi et al., Liquid Pharmaceutical Composition.
U.S. Appl. No. 15/548,730, filed Aug. 3, 2017, Rinaldi et al., Liquid Pharmaceutical Composition.
U.S. Pharmacopeia National Formulary USP 37 NF32 vol. 1, 2014 "USP and NF Excipients" (8 pages).
Krishan et al., "Chapter 16: Development of Formulations for Therapeutic Monoclonal Antibodies and Fc Fusion Proteins" in Formulation and Process Development Strategies for Manufacturing Biopharmaceuticals, ed. Jameel and Hershenson, John Wiley & Sons, Inc., 2010 (39 pages).
U.S. Appl. No. 17/348,078, filed Jun. 15, 2021, Rinaldi et al., Liquid Pharmaceutical Composition.
U.S. Appl. No. 17/348,368, filed Jun. 15, 2021, Rinaldi et al., Liquid Pharmaceutical Composition.
"Golimumab for the Treatment of Rheumatoid Arthritis After Failure of Previous Disease-Modifying Antirheumatic Drugs" dated Jul. 2, 2010, accessed at <https://www.nice.org.uk/guidance/ta225/documents/rheumatoid-arthritis-after-failure-of-previous-antirheumatic-drugs-golimumab-manufacturer-submission2>.
Humira® (Adalimumab) Highlights of Prescribing Information, Jan. 2008, p. 1-34, AbbVie, Inc., North Chicago, IL, USA.
Humira® (Adalimumab) Product Information, Version 21, Mar. 21, 2011, p. 1 -38, Abbott Australasia Pty Ltd., (Botany, NSW, Australia).
Baumgarten et al., (1985), "Normal Human Synovial Fluid: Osmolality and Exercise Induced Changes," J. Bone Joint Surg., 67A(9):1336-1339.
Shanfield et al., (1988), "Synovial Fluid Osmolality in Osteoarthritis and Rheumatoid Arthritis," Clin. Orthop. Relat. Res., 235:289-295.
Sweeney et al., (1993), "Limitation of methods of osmometry: measuring the osmolality of biological fluids," Am J Physiol. 264(3 Pt 2):R469-80.
Anonymous, User Guide for Gonoetc Cryoscopic Osmometer OSMOMAT® 030, dated May 2006 (53 pages).
Anonymous, Section 2.2.35 "Osmolality" from European Pharmacopoeia, European Directorate for the Quality of Medicines & Healthcare (EDQM), Oct. 2020 (1 page).
Anonymous, Section 4.4.6 "Tonicity, Osmolarity, and Preparation of Isotonic Solutions" from Pharmaceutical Dosage Forms and Drug Delivery, CRC Press, Oct. 2011, pp. 63-66.
Anonymous, Chapter 8 "Isotonicity" from Pharmaceutical Calculations, 2017, John Wiley & Sons, pp. 310, 311, and 313.
Anonymous, "Osmolality, Blood" from Mosby's Diagnostic and Laboratory Test Reference, Sep. 2014, p. 669.
"*Application No. 7610240rig1s000, Labeling*," Label for Amjevita, Center for Drug Evaluation and Research (2016) (71 pages).
"Chapter 6: *Injectable Formulations of Poorly Water-Soluble Drugs*" by Bouquet and Wagner, in *Formulating Poorly Water Soluble Drugs*, ed. by R. Williams et al., Springer, 2012, pp. 209-242.
Baker et al., (2010), "Immunogenicity of protein therapeutics: The key causes, consequences and challenges," Self/Nonself 1(4):314-322.
Banks et al., (2009), "The Effect of Sucrose Hydrolysis on the Stability of Protein Therapeutics during Accelerated Formulation Studies," J Pharm Sci. 98(12):4501-4510.
Brummit et al., (2011), "Nonnative Aggregation of an lgG1 Antibody in Acidic Conditions, Part 2: Nucleation and Growth Kinetics with Competing Growth Mechanisms," J Pharm Sci. 100(6):2014-2119.
Carpenter et al., (1997), "Rational Design of Stable Lyophilized Protein Formulations: Some Practical Advice," Pharm Res. 14(8):969-975.
Chennamsetty et al., (2009), "Design of therapeutic proteins with enhanced stability," PNAS 106(29):11937-11942.
Daugherty and Mrsny (2006), "Formulation and delivery issues for monoclonal antibody therapeutics," Adv Drug Delivery Reviews 58:686-706.
Drugbank, "Adalimumab," available at https://www.drugbank.ca/drugs/DB00051 ("Drugbank") accessed Sep. 13, 2019 (10 pages).

(56) References Cited

OTHER PUBLICATIONS

FDA Guidance, Q4B Evaluation and Recommendation of Pharmacopoeial Texts for Use in the ICH Regions, Annex 3(R1) Test for Particulate Contamination: Subvisible Particles General Chapter Guidance for Industry, ICH, Sep. 2017, Revision 1, (10 pages).
Gadgil et al., (2007), "The LC/MS Analysis of Glycation of IgG Molecules in Sucrose Containing Formulations," J Pharm Sci. 96(10):2607-262.
Gekko and Timasheff, (1981), "Mechanism of Protein Stabilization by Glycerol: Preferential Hydration in Glycerol-Water Mixtures," Biochemistry 20:4667-4676.
*Guidance for Industry, Q1A(R2) Stability Testing of New Drug Substances and Products*, ICH, FDA (2003; 25 pages).
*Guideline for Industry, Quality of Biotechnological Products: Stability Testing of Biotechnological/Biological Products*, ICH Q5C Harmonized Tripartite Guideline (FDA, 1996, 12 pages).
Ha et al., (2002), "Peroxide Formation in Polysorbate 80 and Protein Stability," J Pharm Sci. 91(10):2252-2264.
*Handbook of Therapeutic Antibodies*, ed. by S. Dübel, WILEY-VCH Verlag GmbH & Co.KGaA, vol. 1, 2007 (186 pages).
Hawe et al., (2012), "Forced degradation of therapeutic proteins," J. Pharm. Sci. 101:895-913.
Hong et al., (2009),"Size-exclusion Chromatography for the Analysis of Protein Biotherapeutics and their Aggregates," J Liquid Chromatography & Related Techs. 34:2923-2950.
Jefferis, (2009), "Glycosylation as a strategy to improve antibody-based therapeutics," Nature 8:226-34.
Kayser et al., (2011), "Evaluation of a Non-Arrhenius Model for Therapeutic Monoclonal Antibody Aggregation," J Pharm Sci 100(7):2526-2542.
Kayser et al., (2011), "Glycosylation influences on the aggregation propensity of therapeutic monoclonal antibodies," Biotechnol. J. 6:34-44.
Kerwin, (2008), "Polysorbates 20 and 80 Used in the Formulation of Protein Biotherapeutics: Structure and Degradation Pathways," J Pharm Sci. 97(8):2924-2935.
Li et al., (1996), "Effects of Reducing Sugars on the Chemical Stability of Human Relaxin in the Lyophilized State," J Pharm Sci. 85(8):873-877.
Manning et al., (2010), "Stability of Protein Pharmaceuticals: An Update," Pharm Res. 27(4):544-75.
Mason et al., (2012), "Effect of pH and Light on Aggregation and Conformation of an IgG1 mAb," Mol Pharmaceutics 9:774-790.
Parkins and Lashmar, (2000), "The formulation of biopharmaceutical products," Pharm Sci Technol Today, 3(4):129-137.
*Protein Formulation and Delivery*, 2nd ed. by E. McNally and J. Hastedt, Informa Healthcare USA, Inc., vol. 175, 2nd ed, 2008, (133 pages).
*Stability testing of active pharmaceutical ingredients and finished pharmaceutical products, Annex 2*, WHO Technical Report Series, No. 953 (2009; 44 pages).
USP 30/NF 25, "<788> Particulate Matter in Injections," The U.S. Pharmacopeial Convention, 2007, p. 321-327, and USP 30/NF 25, "<788> Particulate Matter in Injections," The U.S. Pharmacopeial Convention, 2007, Supplement 2, p. 3970-3979.
USP 35/NF 30, "<1049> Quality of Biotechnological Products: Stability Testing of Biotechnological/Biological Products," The U.S. Pharmacopeial Convention, 2011, pp. 550-553.
Wang and Roberts, (2013), "Non-Arrhenius Protein Aggregation," AAPS J. 15(3) 840-851.
Wang, W., (2015), "Tolerability of hypertonic injectables," Int J Pharm. 490(1-2):308-15.
Zhou et al., (2011), "Biologies Formulation Factors Affecting Metal Leachables from Stainless Steel," AAPS PharmSciTech 12(1):411-421.
Zhou, S. et al., (2012), Biotherapeutic Formulation Factors Affecting Metal Leachables from Stainless Steel Studied by Design of Experiments AAPS PharmSciTech 13(1):284-294.
Kamerzell et al., (2011), "Protein-excipient interactions: Mechanisms and biophysical characterization applied to protein formulation development," *Advanced Drug Delivery Reviews*, 63:1118-1159.
Kohle et al., (2009) "Impact of Freezing on pH of Buffered Solutions and Consequences for Monoclonal Antibody Aggregation," *Biotechnol. Prog.*, 26(3):727-733.
U.S. Appl. No. 17/979,272, Liquid Pharmaceutical Composition, filed Nov. 2, 2022.
U.S. Appl. No. 17/979,309, Liquid Pharmaceutical Composition, filed Nov. 2, 2022.

* cited by examiner ated to and the benefit of benefit of
LIQUID PHARMACEUTICAL COMPOSITION

CROSS-REFERENCE TO RELATED APPLICATIONS

This application is a continuation of U.S. patent application Ser. No. 16/943,086 filed Jul. 30, 2020, which is a continuation of U.S. patent application Ser. No. 16/584,399 filed Sep. 26, 2019, issued as U.S. Pat. No. 10,729,769 on Aug. 4, 2020, which is a continuation of U.S. patent application Ser. No. 15/313,470, filed Nov. 22, 2016, issued as U.S. Pat. No. 10,426,832 on Oct. 1, 2019, which is a U.S. national stage application under 35 U.S.C. § 371 of International Patent Application No. PCT/EP2015/060816, filed May 15, 2015, which claims priority to and the benefit of European Patent Application No. 14169753.2, filed May 23, 2014, the contents of each of which are incorporated by reference herein in their entireties.

INTRODUCTION

The present invention relates to a novel protein formulation. In particular, the invention relates to a liquid pharmaceutical composition of adalimumab, to a method of manufacturing the composition, to a kit including the composition, to a package including the composition, to a method of manufacturing the package, and to methods of treatment using the composition and/or package.

BACKGROUND

Treatment of tumour necrosis factor-alpha (TNF-α)-related autoimmune diseases, such as rheumatoid arthritis, psoriasis and other autoimmune diseases, has been achieved through the use of FDA-approved drugs such as Adalimumab (HUMIRA®, Abbott Corporation). Adalimumab is a human monoclonal antibody that inhibits human TNF-α activity so as to prevent it from activating TNF receptors, thereby downregulating inflammatory responses associated with autoimmune diseases. Approved medical indications for Adalimumab include rheumatoid arthritis, psoriatic arthritis, ankylosing spondylitis, Crohn's disease, ulcerative colitis, moderate to severe chronic psoriasis and juvenile idiopathic arthritis.

Adalimumab is generally delivered to a patient via subcutaneous injection, and is thus provided in a liquid form, typically in packages such as vials, preloaded syringes, or preloaded "pen devices". Commercially available pen devices (HUMIRA® Pen) generally include a 1 mL pre-filled glass syringe, preloaded with 0.8 mL of a sterile formulation of 40 mg Adalimumab (see below), with a fixed needle (either gray natural rubber or a latex free version) and a needle cover. Commercial formulations (HUMIRA®) of Adalimumab contain the following ingredients:

| Ingredient | Amount per container (mg) (filling volume = 0.8 mL) | Amount (mg/mL) |
|---|---|---|
| Adalimumab | 40 | 50 |
| Citric Acid Monohydrate | 1.04 | 1.3 |
| Dibasic sodium phosphate dihydrate | 1.22 | 1.53 |
| Mannitol | 9.6 | 12 |
| Monobasic sodium phosphate dihydrate | 0.69 | 0.86 |
| Polysorbate 80 | 0.8 | 1 |

-continued

| Ingredient | Amount per container (mg) (filling volume = 0.8 mL) | Amount (mg/mL) |
|---|---|---|
| Sodium chloride | 4.93 | 6.16 |
| Sodium citrate | 0.24 | 0.3 |
| WFI and sodium hydroxide | q.b. to adjust pH to 5.2 | q.b. to adjust pH to 5.2 |

Adalimumab, and its method of manufacture, is described in WO97/29131 (BASF) as D2E7, and elsewhere in the art.

Though the aforementioned commercial formulation of Adalimumab is stable (at least to some extent), the relevant antibody may be unstable over prolonged periods or under stressed conditions, thus precluding prolonged storage of said formulations. Such degradation of the formulation may be due to a variety of factors, including:

Physical effects, such as:
  Inadequate inhibition of aggregation of the relevant protein molecules (a function supposedly served by Tween®80 (polysorbate 80));
  Inadequate inhibition of precipitation;
  Inadequate inhibition of adsorption of the relevant protein molecules at the interface of water and air or at the contact surface of any packaging material (a function supposedly served by Tween®80 (polysorbate 80));
  Inadequate regulation of osmotic pressure (a function supposedly served by mannitol);
Chemical effects, such as:
  Inadequate regulation of oxidation (a function supposedly served by mannitol and potentially undermined by Tween®80 (polysorbate 80), which can promoted oxidation of double bonds);
  Inadequate inhibition of photo-oxidation;
  Inadequate inhibition of hydrolysis of ester bonds leading to the formation of acid, aldehyde and peroxide products, thus affecting the stability of the antibody;
  Inadequate stabilisation and maintenance of pH;
  Inadequate inhibition of protein fragmentation;
  Inadequate inhibition of protein unfolding;

Any, some, or all of the above factors can lead to either an unviable drug product (which may be unsafe for use in medical treatments) or a drug product whose viability is variable and unpredictable, especially in view of the variable stresses (agitation, heat, light) different batches of drug product may be exposed to during manufacture, transport, and storage.

In terms of the physical and chemical stabilisation of Adalimumab, the complex array of components within the aforementioned commercial formulations appears to perform below expectations, especially in view of the large number of components. Though this particular combination of excipients undoubtably represents a 'delicate balance' (given the interplay between various technical factors) and was the result of extensive research and development, in view of the risk of underperformance it is questionable whether such a large number of different excipients is justified, especially given that this inevitably increases processing and cost burdens, toxicity risks, and risks of deleterious interactions between components that could compromise the formulation. Even if the overall performance of the commercial formulations could not be surpassed, an alternative formulation having comparative performance but containing few components would represent a highly desirable replacement for the commercial formulations, for at least the aforesaid reasons.

In order to guarantee reproducible clinical performance of a protein-based pharmaceutical product, such products must remain in a stable and consistent form over time. It is well-established that molecular alterations can occur during every stage of the manufacturing process, including during the production of the final formulation and during storage. Molecular alterations can modify a quality attribute of a biopharmaceutical product, resulting in an undesirable change in the identity, strength or purity of the product. Some such problems are outlined above.

The primary goal of formulation development is to provide a pharmaceutical composition that will support the stability of a biopharmaceutical protein during all stages of its production, storage, shipping and use. Formulation development for an innovative biopharmaceutical protein, or a biosimilar monoclonal antibody (mAb), is essential to its safety, clinical efficacy and commercial success.

There is therefore a need for the provision of alternative or improved liquid formulations of adalimumab. Desirably, any new formulations would solve at least one of the aforementioned problems and/or at least one problem inherent in the prior art, and may suitably solve two or more of said problems. Desirably, the problem(s) of the prior art may be solved whilst reducing the complexity of the formulation.

SUMMARY OF THE INVENTION

According to a first aspect of the present invention there is provided a liquid pharmaceutical composition comprising adalimumab (which suitably includes any biosimilar thereof); an acetate buffering agent (or an acetate buffer system); and a sugar stabiliser; wherein the composition optionally comprises (or excludes) any one or more additional components defined herein in relation to a liquid pharmaceutical composition (e.g. including surfactant, excluding arginine, etc.), optionally in any amount, concentration, or form stipulated herein; and wherein the composition optionally exhibits any one or more parameters or properties given herein in relation to a liquid pharmaceutical composition (e.g. pH, osmolality, aggregation, fragmentation, protein unfolding, turbidity, etc.).

According to a second aspect of the present invention there is provided a liquid pharmaceutical composition comprising adalimumab; an acetate buffering agent (or an acetate buffer system); and a sugar stabiliser; wherein the composition is either (substantially or entirely) free of arginine (suitably L-arginine) or comprises arginine in a concentration of at most 0.1 mM.

According to a third aspect of the present invention there is provided a liquid pharmaceutical composition comprising adalimumab; an acetate buffering agent (or an acetate buffer system); and a sugar stabiliser; wherein the composition is either (substantially or entirely) free of arginine or comprises arginine in a molar ratio of arginine to acetate buffering agent of at most 1:150 (i.e. less than or equal to one mole of arginine for every 150 moles of acetate buffering agent).

According to a fourth aspect of the present invention there is provided a liquid pharmaceutical composition comprising adalimumab; an acetate buffering agent (or an acetate buffer system); and a sugar stabiliser; wherein the composition is either (substantially or entirely) free of arginine or comprises arginine in a weight ratio of arginine to adalimumab of at most 1:3000 (i.e. less than or equal to one part by weight of arginine for every 3000 parts by weight adalimumab).

According to a fifth aspect of the present invention there is provided a package (e.g. pre-filled syringe, pen, intravenous bag, or a package/container containing any of the aforementioned) comprising a liquid pharmaceutical composition as defined herein.

According to a sixth aspect of the present invention there is provided a drug delivery device (e.g. pre-filled syringe or pen, or intravenous bag) comprising a liquid pharmaceutical composition as defined herein.

According to a seventh aspect of the present invention there is provided a kit of parts comprising a drug delivery device, a liquid pharmaceutical composition as defined herein (optionally contained in a package or container), and optionally a set of instructions with directions regarding the administration (e.g. sub-cutaneous) of the liquid pharmaceutical composition.

According to an eighth aspect of the present invention there is provided a method of manufacturing a liquid pharmaceutical composition, the method comprising mixing together adalimumab; an acetate buffering agent (or an acetate buffer system); a sugar stabiliser; and optionally any one or more additional components defined herein in relation to a liquid pharmaceutical composition, optionally in any amount, concentration, or form stipulated; and optionally adjusting any one or more parameters given herein in relation to a liquid pharmaceutical composition (e.g. pH, osmolality).

According to a ninth aspect of the present invention there is provided a liquid pharmaceutical composition obtainable by, obtained by, or directly obtained by a method of manufacturing a liquid pharmaceutical composition as defined herein.

According to a tenth aspect of the present invention there is provided a method of manufacturing a package or a drug delivery device, the method comprising incorporating a liquid pharmaceutical composition as defined herein within a package or drug delivery device.

According to an eleventh aspect of the present invention there is provided a package or a drug delivery device obtainable by, obtained by, or directly obtained by a method of manufacturing a package or a drug delivery device as defined herein.

According to a twelfth aspect of the present invention there is provided a method of treating a disease or medical disorder in a patient in need of such treatment, said method comprising administering to said patient a therapeutically effective amount of a liquid pharmaceutical composition as defined herein.

According to a thirteenth aspect of the present invention there is provided a liquid pharmaceutical composition as defined herein for use in therapy.

According to a fourteenth aspect of the present invention there is provided a use of a liquid pharmaceutical composition as defined herein in the manufacture of a medicament for the treatment of a disease or disorder.

According to a fifteenth aspect of the present invention there is provided a method of treating a tumour necrosis factor-alpha (TNF-α)-related autoimmune disease in a patient in need of such treatment, said method comprising administering to said patient a therapeutically effective amount of a liquid pharmaceutical composition as defined herein.

According to a sixteenth aspect of the present invention there is provided a liquid pharmaceutical composition as defined herein for use in the treatment of a tumour necrosis factor-alpha (TNF-α)-related autoimmune disease.

According to a seventeenth aspect of the present invention there is provided a use of a liquid pharmaceutical composition as defined herein in the manufacture of a medicament for the treatment of a tumour necrosis factor-alpha (TNF-α)-related autoimmune disease.

According to an eighteenth aspect of the present invention there is provided a method of treating rheumatoid arthritis, psoriatic arthritis, ankylosing spondylitis, Crohn's disease, ulcerative colitis, moderate to severe chronic psoriasis and/or juvenile idiopathic arthritis in a patient in need of such treatment, said method comprising administering to said patient a therapeutically effective amount of a liquid pharmaceutical composition as defined herein.

According to a nineteenth aspect of the present invention there is provided a liquid pharmaceutical composition as defined herein for use in the treatment of rheumatoid arthritis, psoriatic arthritis, ankylosing spondylitis, Crohn's disease, ulcerative colitis, moderate to severe chronic psoriasis and/or juvenile idiopathic arthritis.

According to a twentieth aspect of the present invention there is provided a use of a liquid pharmaceutical composition as defined herein in the manufacture of a medicament for the treatment of rheumatoid arthritis, psoriatic arthritis, ankylosing spondylitis, Crohn's disease, ulcerative colitis, moderate to severe chronic psoriasis and/or juvenile idiopathic arthritis.

In further aspects, the invention provides a liquid pharmaceutical composition, a package, a drug delivery device, a kit of parts, a method of manufacturing a liquid pharmaceutical composition, a method of manufacturing a package or a drug delivery device, a method of treating, a liquid pharmaceutical composition for use, and a use of a liquid pharmaceutical composition in the manufacture of a medicament, essentially as defined herein (including in any of the aforementioned twenty aspects) except that, rather than being specific to "adalimumab" (and biosimilars thereof), the invention may instead apply (and thereby be defined as relating) to any TNF-α-inhibiting antibody (anti-TNF-α antibody) (or any biosimilar thereof), albeit suitably an antibody that inhibits human TNF-α activity, and most suitably a human monoclonal antibody that inhibits human TNF-α activity. Suitably the anti-TNF-α antibody is a therapeutically effective medicament (at least when administered in appropriate quantities to a patient in need thereof) (or a biosimilar thereof—see below for definitions of biosimilars in relation to adalimumab, which applies equally to all anti-TNF-α antibodies), suitably one which has received FDA approval. As such, any reference herein to "adalimumab" may, unless incompatible therewith, be construed as a reference to any anti-TNF-α antibody for the purpose of these additional aspects of the invention (whether this relates to absolute or relative amounts, concentrations, parameters, or properties, or whether it relates to certain definitions, such as what constitutes a biosimilar).

One of these further aspects of the present invention provides a liquid pharmaceutical composition comprising an anti-TNF-α antibody (which suitably includes any biosimilar thereof); an acetate buffering agent (or an acetate buffer system); and a sugar stabiliser; wherein the composition optionally comprises (or excludes) any one or more additional components defined herein in relation to a liquid pharmaceutical composition (e.g. including surfactant, excluding arginine, etc.), optionally in any amount, concentration, or form stipulated herein; and wherein the composition optionally exhibits any one or more parameters or properties given herein in relation to a liquid pharmaceutical composition (e.g. pH, osmolality, aggregation, fragmentation, protein unfolding, turbidity, etc.).

In a particular embodiment, the anti-TNF-α antibody is selected from the group including adalimumab, infliximab, certolizumab pegol, golimumab.

Any features, including optional, suitable, and preferred features, described in relation to any particular aspect of the invention may also be features, including optional, suitable and preferred features, of any other aspect of the present invention.

BRIEF DESCRIPTION OF THE DRAWINGS

For a better understanding of the invention, and to show how embodiments of the same are put into effect, reference is now made, by way of example, to the following diagrammatic drawings, in which.

DETAILED DESCRIPTION OF THE INVENTION

Definitions

Figure 1:
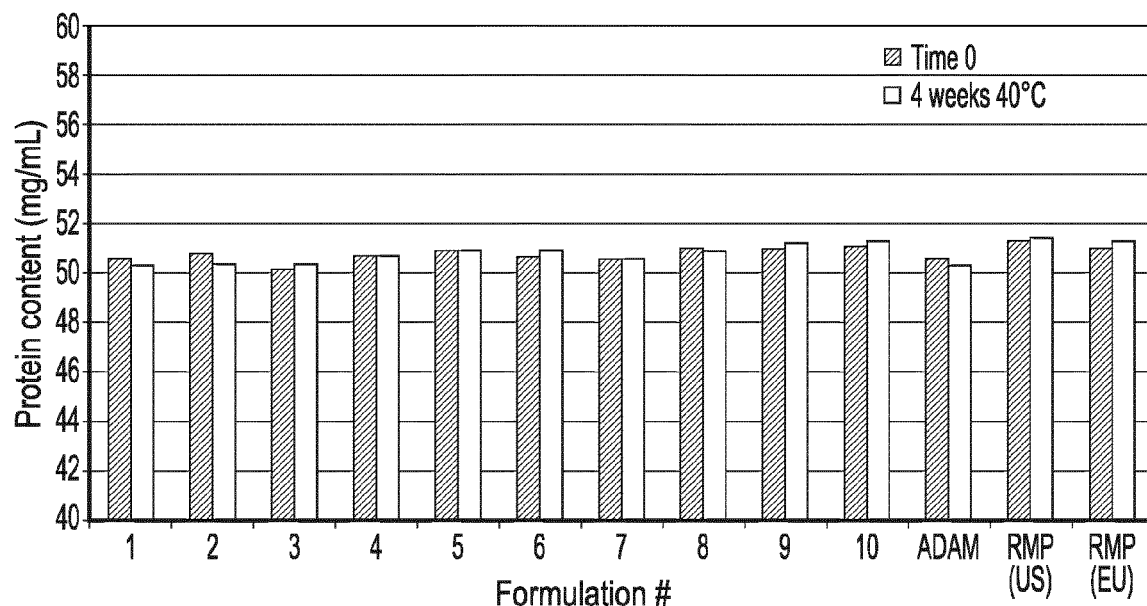
FIG. 1 is a bar chart showing the protein content (mg/mL), as determined by OD, of the DoE1 formulations (of Example 1), along with reference standards (representing comparator HUMIRA® formulations), at an arbitrary start point (blue bars, time=0) and after 4 weeks (red bars) of the formulation(s) being heated at 40° C.

Unless otherwise stated, the following terms used in the specification and claims have the following meanings set out below.

References herein to "adalimumab" include the originator drug substance (as commercially available), adalimumab as defined in WO97/29131 (BASF) (particularly D2E7 therein) and elsewhere in the art, and also biosimilars thereof. D2E7 of WO97/29131 "has a light chain CDR3 domain comprising the amino acid sequence of SEQ ID NO: 3 and a heavy chain CDR3 domain comprising the amino acid sequence of SEQ ID NO: 4". Preferably, the D2E7 antibody has a light chain variable region (LCVR) comprising the amino acid sequence of SEQ ID NO: 1 and a heavy chain variable region (HCVR) comprising the amino acid sequence of SEQ ID NO: 2. WO97/29131 gives details of each of these sequence listings. References herein to "adalimumab" may include biosimilars which, for instance, may share at least 75%, suitably at least 80%, suitably at least 85%, suitably at least 90%, suitably at least 95%, suitably at least 96%, suitably at least 97%, suitably at least 98% or most suitably at least 99% protein sequence identity with any one of protein sequences disclosed in either WO97/29131 (especially in relation to D2E7) or elsewhere in relation to "adalimumab". Alternatively or additionally, references herein to "adalimumab" may include biosimilars which exhibit at least 75%, suitably at least 80%, suitably at least 85%, suitably at least 90%, suitably at least 95%, suitably at least 96%, suitably at least 97%, suitably at least 98% or most suitably at least 99% protein sequence homology with any one of protein sequences disclosed in either WO97/29131 (especially in relation to D2E7) or elsewhere in relation to "adalimumab". Alternatively or additionally, a biosimilar may have a (slightly) different glycosylation profile, even if the protein sequence is substantially the same or different to the extent specified above.

The term "biosimilar" (also known as follow-on biologics) is well known in the art, and the skilled person would readily appreciate when a drug substance would be considered a biosimilar of adalimumab. Furthermore, such "biosimilars" would need to be officially approved as a "biosimilar" for marketing before said "biosimilar" is sold on the open market. The term "biosimilar" is generally used to describe subsequent versions (generally from a different source) of "innovator biopharmaceutical products" ("biologics") whose drug substance is made by a living organism or derived from a living organism or through recombinant DNA or controlled gene expression methodologies) that have been previously officially granted marketing authorisation. Since biologics have a high degree of molecular complexity, and are generally sensitive to changes in manufacturing processes (e.g. if different cell lines are used in their production), and since subsequent follow-on manufacturers generally do not have access to the originator's molecular clone, cell bank, know-how regarding the fermentation and purification process, nor to the active drug substance itself (only the innovator's commercialized drug product), any "biosimilar" is unlikely to be exactly the same as the innovator drug product.

For the purposes of various molar calculations (e.g. for molar ratios between adalimumab and another component of the liquid pharmaceutical composition of the invention) the molecular weight of adalimumab may be taken to be 144190.3 g/mol (reference molecular weight) based on details disclosed on the CAS database for CAS #331731-18-1, Adalimumab, where the molecular formula is taken as $C_{6428}H_{9912}N_{1694}O_{1987}S_{46}$. As such, a liquid pharmaceutical composition containing 50 mg/mL adalimumab may be considered a 0.347 mM (or 347 µM) solution of adalimumab. This is not intended to be in any way limiting regarding the nature of any biosimilars of adalimumab covered by the scope of the present invention, nor the level of glycosylation, either of which may affect the actual molecular weight. However, where a biosimilar does have a different molecular weight, the abovementioned reference molecular weight should be suitably used for the purposes of assessing whether or not such a biosimilar falls within the scope of any molar definitions stipulated within this specification. So the number of moles in a known weight of said biosimilar should be calculated, just for the purposes of this invention, using the above reference molecular weight.

Herein, the term "buffer" or "buffer solution" refers to a generally aqueous solution comprising a mixture of an acid (usually a weak acid, e.g. acetic acid, citric acid, imidazolium form of histidine) and its conjugate base (e.g. an acetate or citrate salt, for example, sodium acetate, sodium citrate, or histidine) or alternatively a mixture of a base (usually a weak base, e.g. histidine) and its conjugate acid (e.g. protonated histidine salt). The pH of a "buffer solution" will change very only slightly upon addition of a small quantity of strong acid or base due to the "buffering effect" imparted by the "buffering agent".

Herein, a "buffer system" comprises one or more buffering agent(s) and/or an acid/base conjugate(s) thereof, and more suitably comprises one or more buffering agent(s) and an acid/base conjugate(s) thereof, and most suitably comprises one buffering agent only and an acid/base conjugate thereof. Unless stated otherwise, any concentrations stipulated herein in relation to a "buffer system" (i.e. a buffer concentration) suitably refers to the combined concentration of the buffering agent(s) and/or acid/base conjugate(s) thereof. In other words, concentrations stipulated herein in relation to a "buffer system" suitably refer to the combined concentration of all the relevant buffering species (i.e. the species in dynamic equilibrium with one another, e.g. acetate/acetic acid). As such, a given concentration of an acetate buffer system generally relates to the combined concentration of acetate (or acetate salt(s), e.g. sodium acetate) and acetic acid. The overall pH of the composition comprising the relevant buffer system is generally a reflection of the equilibrium concentration of each of the relevant buffering species (i.e. the balance of buffering agent(s) to acid/base conjugate(s) thereof).

Herein, the term "buffering agent" refers to an acid or base component (usually a weak acid or weak base) of a buffer or buffer solution. A buffering agent helps maintain the pH of a given solution at or near to a pre-determined value, and the buffering agents are generally chosen to complement the pre-determined value. A buffering agent is suitably a single compound which gives rise to a desired buffering effect, especially when said buffering agent is mixed with (and suitably capable of proton exchange with) an appropriate amount (depending on the pre-determined pH desired) of its corresponding "acid/base conjugate", or if the required amount of its corresponding "acid/base conjugate" is formed in situ—this may be achieved by adding strong acid or base until the required pH is reached. By way of example:

An acetate "buffering agent" is suitably an acetate salt, for example, sodium acetate, suitably mixed with its acid/base conjugate, acetic acid. Such a buffer system may be formed by simply mixing a given amount of sodium acetate with a given amount of acetic acid. Alternatively, however, such a buffer may be formed by adding a given amount of a base, suitably a strong base (e.g. sodium hydroxide) to the acetic acid until the desired pH (and thus the desired balance of sodium acetate/acetic acid) is reached. Herein, except where the contrary is stated, any concentrations given in relation to an acetate buffer or acetate buffering agent suitably refer to the combined concentration of the buffering agent(s) (e.g. sodium acetate) and/or acid/base conjugate(s) thereof (e.g. acetic acid). The skilled person is readily able to calculate such concentrations. Such concentrations may be calculated by reference to the combined concentrations of buffering agent(s) and acid/base conjugate(s), where a buffer system is formed by simply mixing together buffering agent(s) and acid/base conjugate(s). Alternatively, where a buffer system is formed by mixing either the buffering agent(s) or acid/base conjugate(s) with a pH adjuster (e.g. strong acid or strong base) to produce a mixture of each, suitably such concentrations may be calculated by reference to the starting amounts/concentrations of the buffering agent(s) or acid/base conjugate(s) respectively. For example, where a buffer system is formed using a known amount/concentration of acetic acid which is mixed with a pH adjuster (e.g. sodium hydroxide) until the desired pH is reached, the concentration of the buffer system may be calculated by reference to the initial amount of acetic acid.

Herein, an "acid/base conjugate" refers to the conjugate acid or conjugate base (whichever is relevant at a particular pH—typically the conjugate acid in the context of the present invention) of a particular "buffering agent". The acid/base conjugate of an acetate buffering agent (e.g. sodium acetate) is suitably acetic acid.

Herein, the term "buffering species" refers to the particular species (excluding any associated counteranions or countercations—i.e. ignore sodium ions for sodium acetate/acetic acid systems) of a given buffer system which are in dynamic equilibrium with (and proton-exchange with) one another. For example, acetate anions and acetic acid together constitute the "acetate buffering species" of a "acetate buffer system".

Since it is somewhat difficult to define quantities (whether absolute or relative) of a buffer system by reference to weight (since the total weight will depend on the desired pH, which will affect the amount of counterions present), herein weight-based quantities may instead be determined by reference to a theoretical weight of the relevant "buffering species". At least two species are present in any given set of "buffering species" (in relative amounts that can only be determined by reference to the pH), each with a different molecular weight (which usually differs by just 1). Therefore, to enable viable weight calculations and references, for the purposes of this specification the weight of any given set of "buffering species" is given as a theoretical weight based on just one of the buffering species, namely the most acidic of the buffering species (i.e. the most protonated form at any given pH). So the weight of a given set of "buffering species" is quoted as the weight of acid-species equivalents. By way of example, in an acetate buffer system the acetate buffering species may consist of acetate anions (ignore countercations) and acetic acid. The weight of the "buffering species" is therefore calculated as if acetic acid was the only species present in the buffer system (even though acetate is clearly present alongside acetic acid). Thus, any reference to a weight or weight ratio involving a "acetate buffering species" suitably refers to the theoretical weight of acetic acid equivalents within the buffer system. As such, where a composition is formed by adding a pH adjuster (e.g. sodium hydroxide) to a fixed amount of acetic acid, the original weight of acetic acid may be considered to be the weight of the "buffering species" regardless of the ultimate pH. Alternatively, if the concentration (i.e. molarity) of a buffer system is known, this can be converted into a weight of "buffering species" by reference to the molecular weight of the most acidic form of the relevant buffering species (e.g. acetic acid), and ignoring the fact that acetate anions are also present.

Unless stated otherwise, references herein to an "amino acid" or "amino acids", whether specific (e.g. arginine, histidine) or general (e.g. any amino acid), in the context of their presence or otherwise within compositions (especially pharmaceutical liquid compositions of the invention) relate to the corresponding free amino acid(s) (regardless of its/their protonation state and/or salt form, though for consistency amounts are suitably calculated by reference to the free amino acid per se). This may suitably include natural and/or artificial amino acids. Unless stated to the contrary, such references are not intended to relate to amino acid residue(s) covalently incorporated as part of a larger compound (as opposed to a composition comprising multiple compounds), such as a peptide or protein (where such amino acid residues are linked via peptide bonds). As such, though adalimumab, as a protein, contains amino acid residues, it is not considered to comprise any "free amino acid(s)". By way of example, a composition defined as being "free of arginine" does not contain any free arginine but it may still include one or more proteins (e.g. adalimumab) which do themselves comprise arginine residues.

Unless stated otherwise, references herein to any one or more "amino acids", whether specific or general, suitably relate to the L-stereoisomers or a racemate thereof, most suitably L-amino acids.

The term "substantially free", when used in relation to a given component of a composition (e.g. "a liquid pharmaceutical composition substantially free of arginine"), refers to a composition to which essentially none of said component has been added. As explained above, such references have no bearing on the presence of amino acid residue(s) within a protein structure. When a composition is "substantially free" of a given component, said composition suitably comprises no more than 0.001 wt % of said component, suitably no more than 0.0001 wt % of said component, suitably no more than 0.00001 wt %, suitably no more than 0.000001 wt %, suitably no more than 0.0000001 wt % thereof, most suitably no more than 0.0001 parts per billion (by weight).

The term "entirely free", when used in relation to a given component of a composition (e.g. "a liquid pharmaceutical composition substantially free of arginine"), refers to a composition containing none of said component. As explained above, such references have no bearing on the presence of amino acid residue(s) within a protein structure.

Herein, in the context of the present specification, a "strong acid" is suitably one having a $pK_a$ of −1.0 or less, whereas a "weak acid" is suitably one having a $pK_a$ of 2.0 or more. Herein, in the context of the present specification, a "strong base" is suitably one whose conjugate acid has a $pK_a$ of 12 or higher (suitably 14 or higher), whereas a "weak base" is suitably one whose conjugate acid has a $pK_a$ of 10 or less.

Herein, a "stabiliser" refers to a component which facilitates maintenance of the structural integrity of the biopharmaceutical drug, particularly during freezing and/or lyophilization and/or storage (especially when exposed to stress). This stabilising effect may arise for a variety of reasons, though typically such stabilisers may act as osmolytes which mitigate against protein denaturation. Typical stabilisers include amino acids (i.e. free amino acids not part of a peptide or protein—e.g. glycine, arginine, histidine, aspartic acid, lysine) and sugar stabilisers, such as a sugar polyol (e.g. mannitol, sorbitol), and/or a disaccharide (e.g. trehalose, sucrose, maltose, lactose), though the liquid pharmaceutical compositions of the invention include a stabiliser, at least one of which is a sugar stabiliser (i.e. either a sugar polyol or a disaccharide). Most suitably the at least one sugar stabiliser is a non-reducing sugar (be it a sugar polyol or a disaccharide).

Herein, a "non-reducing sugar" is generally a sugar without any aldehyde moieties or without the capability of forming an aldehyde moiety (e.g. through isomerism).

Herein, a "tonicity modifier" or "tonicifier" refers to a reagent whose inclusion within a composition suitably contributes to (or increases) the overall osmolality and osmolarity of the composition. Suitably, a tonicifier, as used herein includes an agent which functions to render a solution similar in osmotic characteristics to physiologic fluids.

Herein, references to specific amounts of a given component of a composition, especially a buffering agent, stabiliser, amino acid, surfactant, or tonicifier, suitably relate to the amounts of the pure anhydrous form of the relevant component (or compositions formed by using said amounts of the pure anhydrous form), even though such a component may be used in a non-anhydrous form when forming the composition. Amounts of any corresponding non-anhydrous forms (e.g. monohydrates, dihydrates, etc.) may be readily calculated by simply using the appropriate multiplier. For instance, unless stated otherwise (as per the Examples, where quantities relate to trehalose dihydrate), amounts stipulated in relation to trehalose refer to the anhydrous form of trehalose (or compositions formed by using the stipulated amounts/concentrations of anhydrous trehalose), which has a molecular weight of 342.296 g/mol, so to calculate the corresponding amount of trehalose dihydrate needed to form the same composition (less water would have to be added) it is necessary to multiply the stipulated amount by 378.33/342.296, since 378.33 is the molecular weight of trehalose dihydrate. The skilled person would readily understand how to judiciously adjust the quantity of diluent/water depending on the form of the components used, in order to derive the target concentrations.

Herein, the term "pharmaceutical composition" refers to a formulation of a pharmaceutical active which renders the biological activity of the active ingredient therapeutically effective, but which does not include other ingredients which are obviously toxic to a subject to which the formulation are intended to be administered.

Herein, the term "stable" generally refers to the physical stability and/or chemical stability and/or biological stability of a component, typically an active or composition thereof, during preservation/storage.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

In the context of the present invention, a "therapeutically effective amount" or "effective amount" of the antibody means an amount that is effective, when administered to a mammal for treating a disease or disorder, in prophylactic and therapeutic aspect and the antibody is effective in treatment of the diseases concerned.

The "therapeutically effective amount" will vary depending on the compound, the disease and its severity and the age, weight, etc., of the mammal to be treated.

The term "human TNF-α" refers to the human cytokine which exists in a 17 kD secreted form and a 26 kD membrane-associated form, and in a biologically active form, TNF-α could be observed as a trimer of covalently-bound 17 kD molecule. Its specific structure can be found in Pennica, D. et al. (1984) Nature 312: 724-729; Davis, J. M. et al. (1987) Biochemistry 26, 1322-1326; and Jones, E. Y. et al. (1989) Nature 338: 225-228.

The term "recombinant human antibody" is intended to include a human antibody prepared, expressed, produced or isolated using a recombinant method.

Herein, amounts stipulated for components and ingredients, whether specified in terms of "parts", ppm (parts per million), percentages (%, e.g. wt %), or ratios, are intended to be by weight, unless stated otherwise.

Where the quantity or concentration of a particular component of a given composition is specified as a weight percentage (wt % or % w/w), said weight percentage refers to the percentage of said component by weight relative to the total weight of the composition as a whole. It will be understood by those skilled in the art that the sum of weight percentages of all components of a composition (whether or not specified) will total 100 wt %. However, where not all components are listed (e.g. where compositions are said to "comprise" one or more particular components), the weight percentage balance may optionally be made up to 100 wt % by unspecified ingredients (e.g. a diluent, such as water, or other non-essentially but suitable additives).

Herein, unless stated otherwise, the term "parts" (e.g. parts by weight, pbw) when used in relation to multiple ingredients/components, refers to relative ratios between said multiple ingredients/components. Expressing molar or weight ratios of two, three or more components gives rise to the same effect (e.g. a molar ratio of x, y, and z is $x_1:y_1:z_1$ respectively, or a range $x_1-x_2:y_1-y_2:z_1-z_2$). Though in many embodiments the amounts of individual components within a composition may be given as a "wt %" value, in alternative embodiments any or all such wt % values may be converted to parts by weight (or relative ratios) to define a multi-component composition. This is so because the relative ratios between components is often more important than the absolute concentrations thereof in the liquid pharmaceutical compositions of the invention. Where a composition comprising multiple ingredients is described in terms of parts by weight alone (i.e. to indicate only relative ratios of ingredients), it is not necessary to stipulate the absolute amounts or concentrations of said ingredients (whether in toto or individually) because the advantages of the invention can stem from the relative ratios of the respective ingredients rather than their absolute quantities or concentrations. However, in certain embodiments, such compositions consists essentially of or consist of the stipulated ingredients and a diluents (e.g. water).

Where a composition is said to comprise a plurality of stipulated ingredients (optionally in stipulated amounts of concentrations), said composition may optionally include additional ingredients other than those stipulated. However, in certain embodiments, a composition said to comprise a plurality of stipulated ingredients may in fact consist essentially of or consist of all the stipulated ingredients.

Herein, where a composition is said to "consists essentially of" a particular component, said composition suitably comprises at least 70 wt % of said component, suitably at least 90 wt % thereof, suitably at least 95 wt % thereof, most suitably at least 99 wt % thereof. Suitably, a composition said to "consist essentially of" a particular component consists of said component save for one or more trace impurities.

Herein, the term "particle size" or "pore size" refers respectively to the length of the longest dimension of a given particle or pore. Both sizes may be measured using a laser particle size analyser and/or electron microscopes (e.g. tunneling electron microscope, TEM, or scanning electron microscope, SEM). The particle count (for any given size) can be obtained using the protocols and equipment outlined in the Examples, which relates to the particle count of sub-visible particles.

Liquid Pharmaceutical Composition

The present invention provides a liquid pharmaceutical composition, suitably as defined herein. The composition suitably comprises a human monoclonal antibody, suitably one which inhibits human TNF-α activity, suitably so as to prevent it from activating TNF receptors. Most suitably the liquid pharmaceutical composition comprises adalimumab, which in itself suitably includes any biosimilar thereof. The composition suitably comprises an acetate buffering agent (or a acetate buffer system). The composition suitably comprises a sugar stabiliser. The composition is suitably (substantially or entirely) free of arginine or comprises arginine either in a concentration of at most 0.1 mM, in a molar ratio of arginine to acetate buffering agent (or a acetate buffer system) of at most 1:150, or in a weight ratio of arginine to adalimumab of at most 1:3000 (i.e. less than or equal to one part by weight of arginine for every 3000 parts by weight acetate buffering agent). Alternatively or in addition, the composition may suitably include any one or more additional components defined herein in relation to a liquid pharmaceutical composition (e.g. including surfactant, excluding arginine, etc.), optionally in any amount, concentration, or form stipulated herein; and wherein the composition optionally exhibits any one or more parameters or properties given herein in relation to a liquid pharmaceutical composition (e.g. pH, osmolality).

Advantageously, the present invention provides alternative and improved liquid pharmaceutical compositions, which generally exhibit better stability and viability than those of the prior art. As is illustrated herein (see Examples), the liquid pharmaceutical formulations of the present invention have comparable or improved characteristics when compared to the conventional formulations of adalimumab, for example the commercially available formulation Humira®, when subjected to different stressing conditions (thermal, mechanical and light). Their performance is also generally comparable or better than many other comparative formulations that were subjected to the same stress testing. Since these stressing conditions are highly representative of the kind of stress such formulations are subjected to during manufacture, transport, and storage, they provide an excellent indication of the advantages of the invention. That such good stability performance can be achieved using less complex formulations with fewer excipients was considered surprising in view of the general teachings of the prior art.

Adalimumab

Adalimumab, which is commercially available in HUMIRA® formulations, and its method of manufacture, is described in WO97/29131 (BASF) as D2E7, and elsewhere in the art. It is described as having "a light chain CDR3 domain comprising the amino acid sequence of SEQ ID NO: 3 and a heavy chain CDR3 domain comprising the amino acid sequence of SEQ ID NO: 4" (WO97/29131). Furthermore, the D2E7 antibody is described as having a light chain variable region (LCVR) comprising the amino acid sequence of SEQ ID NO: 1 and a heavy chain variable region (HCVR) comprising the amino acid sequence of SEQ ID NO: 2 (WO97/29131).

The medical indications and function of Adalimumab, are elucidated hereinbefore.

In the context of the invention "adalimumab" includes biosimilars, as defined herein before, and the skilled person would readily appreciate the scope of the term "adalimumab" in the context of the invention.

In an embodiment, the liquid pharmaceutical composition comprises adalimumab at a concentration of from about 5 to about 150 mg/ml, suitably from about 25 to about 75 mg/mL. For example, the adalimumab may be present in the formulation at a concentration of about 25, about 30, about 35, about 40, about 45, about 50, about 55, about 60, about 65, about 70 or about 75 mg/ml. In an embodiment, the adalimumab is present at a concentration from about 45 to about 55 mg/ml. In an embodiment, the adalimumab is present at a concentration of about 50 mg/ml.

Buffer, Buffering Agent, and pH

Suitably, the liquid pharmaceutical composition is a buffered solution whose pH is stabilised by a buffering agent (or a buffer system), suitably in combination with an acid/base conjugate of the buffering agent. As such, the liquid pharmaceutical composition suitably comprises a buffering agent as defined herein. Preferably, the liquid pharmaceutical composition additionally comprises an acid/base conjugate, wherein said acid/base conjugate corresponds to the conjugate acid or conjugate base of the buffering agent, depending on whether the buffering agent is itself a base or acid respectively. Collectively, the buffering agent and its acid/base conjugate may be considered a "buffer system". The liquid pharmaceutical composition thus suitably comprises a "buffer system" (suitably comprising a buffering agent(s) and an acid/base conjugate(s) thereof), and any concentrations stipulated in relation to the buffer system generally relate to the combined concentrations of the buffering agent(s) and any acid/base conjugate(s) thereof. Any "buffer system" suitably comprises a weak acid and a weak base (see above definitions).

Suitably, the buffering agent is an acetate buffering agent. Suitably the acetate buffering agent is an acetate salt, suitably comprising anionic acetate (i.e. AcO⁻) and one or more pharmaceutically acceptable countercations. A suitable acetate salt may include a metal acetate salt (e.g. an alkali metal acetate or an alkaline earth metal acetate), or a non-metal acetate salt (e.g. ammonium acetate, triethylammonium acetate). In a particular embodiment, the buffering agent (and the acetate salt) is sodium acetate.

Suitably, the liquid pharmaceutical composition comprises an acid/base conjugate of the buffering agent, most suitably acetic acid as the conjugate acid of an acetate salt. The combination of the buffering agent and its acid/base conjugate constitute a buffer system. Suitably, the liquid pharmaceutical composition comprises the buffering agent and its corresponding acid/base conjugate, suitably such that together the buffering agent and its acid/base conjugate are present at a level (i.e. absolute amount or concentration) and in a relative amount (or concentration) sufficient to provide the desired pH for the composition. The buffer system may be formed by simply mixing the buffering agent with its acid/base conjugate or may alternatively be formed by mixing an acid or base with either the buffering agent or its acid/base conjugate in order to form in situ the desired mixture of buffering agent and acid/base conjugate. For example, the buffer system may be formed by simply mixing the acetate buffering agent (e.g. sodium acetate) with its acid/base conjugate (i.e. acetic acid), suitably in a ratio appropriate to furnish the desired pH. Alternatively, the buffer system may be formed by adding a base (e.g. sodium hydroxide) to the acid/base conjugate (i.e. acetic acid) of the acetate buffering agent, suitably in an amount appropriate to furnish the desired pH and mixture of the buffering agent (e.g. sodium acetate) and corresponding acid/base conjugate (i.e. acetic acid). Alternatively, either method of forming the buffer system may be employed, and pH may be judiciously adjusted by either adding further acid (suitably strong acid, such as HCl) or further base (suitably strong base, such as sodium hydroxide).

Most suitably, the buffer system is an acetate buffer system, suitably comprising an acetate salt and acetic acid.

Suitably, the liquid pharmaceutical composition comprises at most one buffering agent. Suitably, the liquid pharmaceutical composition comprises at most one buffer system.

Suitably, the liquid pharmaceutical composition has a pH greater than or equal to 5.0. Suitably, the liquid pharmaceutical composition has a pH less than or equal to 6.7.

In a particular embodiment, especially where the buffering agent is an acetate buffering agent, the liquid pharmaceutical composition has a pH between 5.0 and 5.5. In a particular embodiment, the liquid pharmaceutical composition has a pH between 5.1 and 5.3. In a particular embodiment, the liquid pharmaceutical composition has a pH of about 5.2.

Suitably, the liquid pharmaceutical composition comprises a buffer system (suitably an acetate buffer system comprising an acetate buffering agent) at a concentration of from about 2 to about 50 mM. In an embodiment, the buffer system is present at a concentration of between 5 and 14 mM, most suitably about 10 mM. In an embodiment, the buffer system is present at a concentration of 10 mM. In an embodiment, the liquid pharmaceutical composition comprises a sodium acetate/acetic acid buffer system at a concentration of 10 mM. This includes where the "buffering agent(s)" (e.g. sodium acetate) is formed by the addition of a strong base (e.g. sodium hydroxide) to the conjugate acid of the buffering agent(s) (e.g. acetic acid).

Suitably, the liquid pharmaceutical composition comprises the buffering species (suitably acetate buffering species) at a concentration of from about 0.120 mg/mL to about 3.0 mg/mL. In an embodiment, the buffering species are present at a concentration of between 0.30 mg/mL and 0.84 mg/mL, most suitably about 0.60 mg/mL. This includes where the "buffering agent" (e.g. sodium acetate) is formed by the addition of a strong base (e.g. sodium hydroxide) to the conjugate acid of the buffering agent (e.g. acetic acid).

Suitably, the liquid pharmaceutical composition comprises the buffer system (suitably the acetate buffer system) in a molar ratio of buffer system to adalimumab of from about 5:1 to about 145:1. In an embodiment, the buffer system is present in a molar ratio of buffer system to adalimumab of from about 14:1 to about 40:1, most suitably about 29:1. In an embodiment, the buffer system is present at a concentration of 29:1. This includes where the "buffering agent(s)" (e.g. sodium acetate) is formed by the addition of a strong base (e.g. sodium hydroxide) to the conjugate acid of the buffering agent (e.g. acetic acid).

As illustrated in the Example section, liquid pharmaceutical compositions of the invention including an acetate buffer system perform particularly well in stress tests, especially in relation to fragmentation and protein unfolding, which can be important indicators of stability and drug product viability. Furthermore, liquid pharmaceutical compositions whose acetate buffer system maintains a steady pH 5.2 perform particularly well.

Sugar Stabiliser

Suitably, the liquid pharmaceutical composition comprises a stabiliser, most suitably a sugar stabiliser. Suitably, such a component facilitates maintenance of the structural integrity of the biopharmaceutical drug, particularly during freezing and/or lyophilization and/or storage (especially when exposed to stress).

The liquid pharmaceutical composition may comprise one or more sugar stabilisers, though in preferred embodiments only a single sugar stabiliser is present.

Suitably, the sugar stabiliser is a sugar polyol (including sugar alcohols) and/or a disaccharide.

The sugar stabiliser is suitably selected from the group including trehalose, mannitol, sucrose, sorbitol, maltose, lactose, xylitol, arabitol, erythritol, lactitol, maltitol, inositol.

In a particular embodiment, the sugar stabiliser is selected from the group including trehalose, mannitol, sucrose, maltose, lactose, xylitol, arabitol, erythritol, lactitol, maltitol, inositol.

In a particular embodiment, the sugar stabiliser is a non-reducing sugar, optionally a non-reducing sugar listed anywhere herein.

In a particular embodiment, the sugar stabiliser is selected from the group including trehalose and mannitol.

In a particular embodiment, the sugar stabiliser is trehalose. Trehalose is a particularly advantageous sugar stabiliser for use alongside an acetate buffering agent/buffer system in liquid adalimumab formulations.

Suitably, the liquid pharmaceutical composition comprises at most one sugar stabiliser, suitably at most one sugar polyol and/or disaccharide. Suitably, the liquid pharmaceutical composition comprises trehalose as the only sugar stabiliser.

Suitably the trehalose used to form the liquid pharmaceutical composition is trehalose dihydrate, though suitably any amounts stipulated in relation to trehalose (unless stated otherwise—as done in the Examples) pertain to pure, anhydrous trehalose. Such amounts may be converted into an amount of trehalose dihydrate by applying an appropriate multiplier. Moreover, for the purposes of assessing whether a given formulation falls within the scope of any of the trehalose quantity definitions given herein, an amount of trehalose dihydrate can be readily converted into a corresponding amount of pure, anhydrous trehalose (with an equal number of moles) through applying said multiplier in reverse. This principle may be adopted for any sugar stabiliser component. Concentrations, when given as a molar concentration, will of course be the same regardless of the hydration state of the sugar stabiliser.

Suitably, the liquid pharmaceutical composition comprises the sugar stabilizer(s) (most suitably trehalose) at a concentration of from about 50 to about 400 mM, more suitably from about 100 to about 300 mM, more suitably from about 150 to about 250 mM. In an embodiment, the sugar stabilizer(s) is present at a concentration of between 190 and 210 mM, most suitably about 200 mM. In an embodiment, trehalose is present at a concentration of 200 mM.

Suitably, the liquid pharmaceutical composition comprises the sugar stabilizer(s) (most suitably trehalose) at a concentration of from about 15 mg/mL to about 140 mg/mL, more suitably from about 35 mg/mL to about 100 mg/mL, more suitably from about 45 mg/mL to about 80 mg/mL. In an embodiment, the sugar stabilizer(s) is present at a concentration of between 65 mg/mL and 72 mg/mL, most suitably about 68 mg/mL. In a particular embodiment, trehalose is present at a concentration of about 68 mg/mL (which equates to about 75.7 mg/mL trehalose dihydrate).

Suitably, the liquid pharmaceutical composition comprises the sugar stabilizer(s) (most suitably trehalose) in a molar ratio of sugar stabilizer(s) to adalimumab of from about 145:1 to about 1150:1, more suitably from about 290:1 to about 860:1, more suitably from about 430:1 to about 720:1. In an embodiment, the sugar stabilizer(s) is present at a molar ratio of sugar stabilizer(s) to adalimumab of from about 550:1 to about 605:1, most suitably about 576:1. In an embodiment, trehalose is present at a molar ratio of trehalose to adalimumab of about 576:1.

As illustrated in the Example section, liquid pharmaceutical compositions of the invention including a sugar stabiliser as defined herein perform particularly well in stress tests, especially in relation to aggregation, fragmentation and protein unfolding, which can be important indicators of stability and drug product viability. Furthermore, liquid pharmaceutical compositions comprising trehalose as the sugar stabiliser perform particularly well.

Diluent

The liquid pharmaceutical compositions of the invention may include any one or more pharmaceutically acceptable diluents, or mixture thereof. However, most suitably the liquid pharmaceutical composition is an aqueous pharmaceutical composition. Most suitably the diluent is water, and suitably water alone. The water is suitably water for injection (WFI).

Suitably the diluent may constitute the balance of ingredients in any liquid pharmaceutical composition, for instance so that the weight percentages total 100%.

Suitably any concentrations given herein in relation to any component of the liquid pharmaceutical composition represent concentrations of said component in (and suitably dissolved in) the diluent in admixture with any other components.

The liquid pharmaceutical composition of the invention is suitably a solution, and is suitably (substantially or entirely) free of particulates or precipitates.

Absent or Low Level Components

Low/No Arginine

Suitably the liquid pharmaceutical composition is either (substantially or entirely) free of arginine (suitably L-arginine) or comprises arginine in a concentration of at most 0.1 mM, more suitably at most 0.01 mM, most suitably at most 0.001 mM.

Suitably the liquid pharmaceutical composition is either (substantially or entirely) free of arginine or comprises arginine in a molar ratio of arginine to buffer system of at most 1:150 (i.e. less than or equal to one mole of arginine for every 150 moles of buffer system), more suitably at most 1:1500, most suitably at most 1:15,000.

Suitably the liquid pharmaceutical composition is either (substantially or entirely) free of arginine or comprises arginine in a weight ratio of arginine to adalimumab of at most 1:3000 (i.e. less than or equal to one part by weight of arginine for every 3000 parts by weight adalimumab), more suitably at most 1:30,000, most suitably at most 1:300,000.

Suitably the liquid pharmaceutical composition is either (substantially or entirely) free of arginine or comprises arginine in a molar ratio of arginine to adalimumab of at most 1:3.75 (i.e. less than or equal to one mole of arginine for every 3.75 moles adalimumab), more suitably at most 1:37.5, most suitably at most 1:375.

As explained herein, such references to "arginine" in the context of their presence or otherwise within liquid pharmaceutical compositions relate to the corresponding free amino acid(s) and not amino acid residue(s) covalently incorporated as part of a larger compound, such as a peptide or protein.

As illustrated in the Example section, liquid pharmaceutical compositions of the invention which (substantially or entirely) exclude arginine perform particularly well in stress tests, especially in relation to aggregation, fragmentation and protein unfolding.

Low/No Amino Acids

Suitably the liquid pharmaceutical composition is either (substantially or entirely) free of amino acids or comprises one or more amino acids in a (collective) concentration of at most 0.1 mM, more suitably at most 0.01 mM, most suitably at most 0.001 mM.

Suitably the liquid pharmaceutical composition is either (substantially or entirely) free of amino acids or comprises one or more amino acids in a (collective) molar ratio of amino acids(s) to buffer system of at most 1:150 (i.e. less than or equal to one mole of amino acids(s) for every 150 moles of buffer system), more suitably at most 1:1500, most suitably at most 1:15,000.

Suitably the liquid pharmaceutical composition is either (substantially or entirely) free of amino acids or comprises one or more amino acids in a (collective) weight ratio of amino acids(s) to adalimumab of at most 1:3000 (i.e. less than or equal to one part by weight of amino acids(s) for every 3000 parts by weight adalimumab), more suitably at most 1:30,000, most suitably at most 1:300,000.

Suitably the liquid pharmaceutical composition is either (substantially or entirely) free of amino acids or comprises one or more amino acids in a (collective) molar ratio of amino acid(s) to adalimumab of at most 1:3.75 (i.e. less than or equal to one mole of amino acid(s) for every 3.75 moles adalimumab), more suitably at most 1:37.5, most suitably at most 1:375.

As explained herein, such references to "amino acids" in the context of their presence or otherwise within liquid pharmaceutical compositions relate to the corresponding free amino acid(s) and not amino acid residue(s) covalently incorporated as part of a larger compound, such as a peptide or protein.

Suitably, the amino acids referred to in this section (and deemed either absent or present in low quantities) may be natural and/or artificial amino acids, though they are preferably natural amino acids. In particular, the liquid pharmaceutical compositions are either (substantially or entirely) free of any amino acids selected from the group including: arginine, lysine, aspartic acid, and histidine; or comprises one or more of the aforesaid amino acids in an amount, concentration, molar ratio, or weight ratio as hereinbefore defined in relation to "amino acid(s)".

As illustrated in the Example section, liquid pharmaceutical compositions of the invention which (substantially or entirely) exclude amino acids or certain amino acids, as defined above, perform particularly well in stress tests, especially in relation to aggregation, fragmentation and protein unfolding.

Low/No Surfactants

Suitably the liquid pharmaceutical composition is either (substantially or entirely) free of surfactants (whether cationic, anionic, amphoteric, or non-ionic) with the optional exception of polysorbate 80 (polyoxyethylene (20) sorbitan monooleate) or comprises one or more of said surfactants (optionally excluding polysorbate 80) in a (collective) concentration of at most 1 mM, more suitably at most 0.1 mM, more suitably at most 0.01 mM, more suitably at most 0.001 mM, most suitably at most 0.0001 mM. The liquid pharmaceutical composition may, under such circumstances, optionally comprise polysorbate 80 as defined herein.

Suitably the liquid pharmaceutical composition is either (substantially or entirely) free of surfactants (whether cationic, anionic, amphoteric, or non-ionic) with the optional exception of polysorbate 80 (polyoxyethylene (20) sorbitan monooleate) or comprises one or more of said surfactants (optionally excluding polysorbate 80) in a (collective) molar ratio of surfactant(s) to buffer system of at most 1:10, more suitably at most 1:100, most suitably at most 1:1000, more suitably at most 1:10,000, suitably at most 1:100,000. The liquid pharmaceutical composition may, under such circumstances, optionally comprise polysorbate 80 as defined herein.

Suitably the liquid pharmaceutical composition is either (substantially or entirely) free of surfactants (whether cationic, anionic, amphoteric, or non-ionic) with the optional exception of polysorbate 80 (polyoxyethylene (20) sorbitan monooleate) or comprises one or more of said surfactants (optionally excluding polysorbate 80) in a (collective) weight ratio of surfactant(s) to adalimumab of at most 1:50 (i.e. less than or equal to one part by weight of surfactant(s) for every 50 parts by weight adalimumab), more suitably at most 1:500, more suitably at most 1:5000, more suitably at most 1:50,000, suitably at most 1:500,000. The liquid pharmaceutical composition may, under such circumstances, optionally comprise polysorbate 80 as defined herein.

Suitably the liquid pharmaceutical composition is either (substantially or entirely) free of surfactants (whether cationic, anionic, amphoteric, or non-ionic) with the optional exception of polysorbate 80 (polyoxyethylene (20) sorbitan monooleate) or comprises one or more of said surfactants (optionally excluding polysorbate 80) in a (collective) molar ratio of surfactant(s) to adalimumab of at most 3:1, more suitably at most 0.3:1, more suitably 0.003:1, more suitably 0.0003:1, suitably 0.00003:1. The liquid pharmaceutical composition may, under such circumstances, optionally comprise polysorbate 80 as defined herein.

Suitably, the surfactants referred to in this section (and deemed either absent or present in low quantities) may be cationic, anionic, amphoteric, or non-ionic surfactants. Suitably, the surfactants referred to in this section (and deemed either absent or present in low quantities) include cationic, anionic, and amphoteric surfactants, but may optionally exclude non-ionic surfactants (e.g. polysorbates or spans) or at least may optionally exclude polysorbate 80. As such, the liquid pharmaceutical composition is either (substantially or entirely) free of cationic, anionic, or amphoteric surfactants or comprises one or more of said surfactants in an amount, concentration, molar ratio, or weight ratio of at most that stipulated in any of the preceding paragraphs of this sub-section in relation to "surfactant(s)" more generally.

The liquid pharmaceutical composition is either (substantially or entirely) free of non-ionic surfactants with the optional exception of polysorbate 80 or comprises one or more of said surfactants in an amount, concentration, molar ratio, or weight ratio of at most that stipulated in any of the preceding paragraphs of this sub-section in relation to "surfactant(s)" more generally.

The liquid pharmaceutical composition is either (substantially or entirely) free of polysorbate surfactants with the optional exception of polysorbate 80 or comprises one or more of said surfactants in an amount, concentration, molar ratio, or weight ratio of at most that stipulated in any of the preceding paragraphs of this sub-section in relation to "surfactant(s)" more generally. The liquid pharmaceutical composition may, under such circumstances, optionally comprise polysorbate 80 as defined herein.

The liquid pharmaceutical composition is either (substantially or entirely) free of polysorbate 20 (also known as Tween®20-polyoxyethylene (20) sorbitan monolaurate) surfactants or comprises one or more of said surfactants in an amount, concentration, molar ratio, or weight ratio of at most that stipulated in any of the preceding paragraphs of this sub-section in relation to "surfactant(s)" more generally.

The liquid pharmaceutical composition may suitably be either (substantially or entirely) free of polysorbate 80 surfactants or comprises said surfactant(s) in an amount, concentration, molar ratio, or weight ratio as hereinbefore defined in relation to "surfactant(s)". The liquid pharmaceutical composition is either (substantially or entirely) free of polysorbate 80 surfactants or comprises one or more of said surfactants in an amount, concentration, molar ratio, or weight ratio of at most that stipulated in any of the preceding paragraphs of this sub-section in relation to "surfactant(s)" more generally.

As illustrated in the Example section, liquid pharmaceutical compositions of the invention which (substantially or entirely) exclude surfactants or certain surfactants, as defined above, perform particularly well in stress tests, especially in relation to aggregation, fragmentation and protein unfolding.

Low/No Phosphate

Suitably the liquid pharmaceutical composition is either (substantially or entirely) free of phosphate buffering agents (e.g. sodium dihydrogen phosphate, disodium hydrogen phosphate) or comprises a phosphate buffer system in a concentration of at most 0.1 mM, more suitably at most 0.01 mM, most suitably at most 0.001 mM.

Suitably the liquid pharmaceutical composition is either (substantially or entirely) free of phosphate buffering agents (e.g. sodium dihydrogen phosphate, disodium hydrogen phosphate) or comprises a phosphate buffer system in a molar ratio of phosphate buffer system to any non-phosphate buffer systems present of at most 1:150 (i.e. less than or equal to one mole of phosphate buffering agent for every 150 moles of non-phosphate buffer system present), more suitably at most 1:1500, most suitably at most 1:15,000.

Suitably the liquid pharmaceutical composition is either (substantially or entirely) free of phosphate buffering agents or comprises a phosphate buffer system in a molar ratio of phosphate buffer system to adalimumab of at most 1:3.75 (i.e. less than or equal to one mole of phosphate buffer system for every 3.75 moles adalimumab), more suitably at most 1:37.5, most suitably at most 1:375.

References to "phosphate buffering agents" in the context of their presence or otherwise within liquid pharmaceutical compositions relate to any phosphate salts in any form or protonation state, including phosphate, monohydrogen phosphate, and dihydrogen phosphate. It does, however, suitably exclude any phosphate moieties or residues that may be covalently incorporated as part of a larger compound, such as a phosphorylated or glycosylated peptide or protein.

As illustrated in the Example section, liquid pharmaceutical compositions of the invention which (substantially or entirely) exclude phosphate buffering agents perform particularly well in stress tests, especially in relation to aggregation, fragmentation and protein unfolding.

Optional Additional Components

Tonicifier

The liquid pharmaceutical composition of the invention suitably comprises a "tonicity modifier" (or "tonicifier") or one or more tonicifiers, suitably as defined herein.

The inclusion of a tonicifier suitably contributes to (or increases) the overall osmolality and osmolarity of the composition. Suitably a tonicifier is present within the composition in a quantity or concentration sufficient for the composition to be (substantially) isotonic with body fluids. Suitably a tonicifier is present within the composition in a quantity or concentration sufficient for the composition to have an osmolarity or osmolality within a range defined herein.

Any suitable tonicifier may be used. However, suitably the tonicifier is selected from the group including water-soluble metal salts (e.g. sodium chloride, potassium chloride, magnesium chloride, calcium chloride), water-soluble tonicifying sugars/sugar alcohols (e.g. glucose, sucrose, mannitol), and/or other water-soluble polyols. Suitably the tonicifier(s) is non-buffering (i.e. gives rise to little or no buffering effect). As such, any metal salt tonicifiers are suitably not buffering agents.

The liquid pharmaceutical composition may comprise one or more tonicifiers, though preferably only a single "tonicifier" as such is present (notwithstanding any tonicifying effects imparted to the composition by components intended to serve another function as defined herein).

Most preferably, the tonicifier is or comprises a metal salt (preferably a non-buffering water-soluble metal salt). Suitably, said metal salt is or comprises a metal halide, suitably an alkali or an alkaline earth metal halide, suitably an alkali metal chloride.

In a particular embodiment, the tonicifier is or comprises sodium chloride. In a particular embodiment, the tonicifier is sodium chloride. Sodium chloride is a particularly advantageous stabiliser for use alongside an acetate buffering agent/buffer system in liquid adalimumab formulations.

Suitably, the liquid pharmaceutical composition comprises the tonicifier(s) (most suitably sodium chloride) at a concentration of from about 10 to about 200 mM, more suitably from about 20 to about 100 mM, more suitably from about 25 to about 75 mM. In an embodiment, the tonicifier(s) is present at a concentration of between 40 and 60 mM, most suitably about 50 mM. In an embodiment, sodium chloride is present at a concentration of 50 mM.

Suitably, the liquid pharmaceutical composition comprises the tonicifier(s) (most suitably sodium chloride) at a concentration of from about 0.5 mg/mL to about 12 mg/mL, more suitably from about 1.2 mg/mL to about 5 mg/mL, more suitably from about 1.5 mg/mL to about 4.4 mg/mL. In an embodiment, the tonicifier(s) is present at a concentration of between 2.7 mg/mL and 3.1 mg/mL, most suitably about 2.9 mg/mL. In a particular embodiment, sodium chloride is present at a concentration of about 2.9 mg/mL.

Suitably, the liquid pharmaceutical composition comprises the tonicifier(s) (most suitably sodium chloride) in a molar ratio of tonicifier to adalimumab of from about 30:1 to about 580:1, more suitably from about 60:1 to about 290:1, more suitably from about 70:1 to about 220:1. In an embodiment, the tonicifier(s) is present at a molar ratio of tonicifier to adalimumab of from about 115:1 to about 175:1, most suitably about 145:1. In an embodiment, sodium chloride is present at a molar ratio of sodium chloride to adalimumab of about 145:1.

As illustrated in the Example section, liquid pharmaceutical compositions of the invention including a tonicifier as defined herein perform particularly well in stress tests, especially in relation to aggregation, fragmentation and protein unfolding, which can be important indicators of stability and drug product viability. Furthermore, liquid pharmaceutical compositions comprising sodium chloride, particularly in an amount range as stipulated, perform particularly well.

Surfactant

The liquid pharmaceutical composition of the invention suitably comprises a surfactant or one or more surfactants, suitably as defined herein.

The inclusion of a surfactant suitably contributes to stabilisation of the adalimumab protein.

Any suitable surfactant may be used. However, suitably the surfactant is a non-ionic surfactant, most suitably a polysorbate (polyoxyethylene glycol sorbitan alkyl esters) or span (sorbitan alkyl esters) surfactant.

Though one or more surfactants may be included within the liquid pharmaceutical composition of the invention, most suitably only a single surfactant is present, most suitably a single non-ionic surfactant (suitably as defined herein).

The surfactant(s) are suitably selected from Polysorbate 20 (Polyoxyethylene (20) sorbitan monolaurate), Polysorbate 40 (Polyoxyethylene (20) sorbitan monopalmitate), Polysorbate 60 (Polyoxyethylene (20) sorbitan monostearate), Polysorbate 80 (Polyoxyethylene (20) sorbitan monooleate), Sorbitan monolaurate, Sorbitan monopalmitate, Sorbitan monostearate, Sorbitan tristearate, and/or Sorbitan monooleate.

In a particular embodiment, the surfactant(s) are selected from Polysorbate 20, Polysorbate 40, Polysorbate 60, and/or Polysorbate 80. In a particular embodiment, the liquid pharmaceutical composition comprises a single surfactant selected from Polysorbate 20, Polysorbate 40, Polysorbate 60, and Polysorbate 80.

In a particular embodiment, the surfactant is polysorbate 80 or polysorbate 20. In a particular embodiment, the surfactant is polysorbate 80.

Suitably, the liquid pharmaceutical composition comprises the surfactant(s) (most suitably polysorbate 80) at a concentration of from about 0.0001 to about 5 mM (i.e. 0.1 µM-5 mM), more suitably from about 0.001 to about 2 mM, more suitably from about 0.01 to about 1.0 mM. In an embodiment, the surfactant(s) is present at a concentration of between 0.72 and 0.80 mM, most suitably about 0.76 mM. In an embodiment, polysorbate 80 is present at a concentration of 0.76 mM.

Suitably, the liquid pharmaceutical composition comprises the surfactant(s) (most suitably polysorbate 80) at a concentration of from about 0.001 mg/mL to about 5 mg/mL, more suitably from about 0.01 mg/mL to about 2 mg/mL, more suitably from about 0.05 mg/mL to about 1.5 mg/mL. In an embodiment, the surfactant(s) is present at a concentration of between 0.9 mg/mL and 1.1 mg/mL, most suitably about 1.0 mg/mL. In a particular embodiment, polysorbate 80 is present at a concentration of about 1.0 mg/mL.

Suitably, the liquid pharmaceutical composition comprises the surfactant(s) (most suitably polysorbate 80) in a molar ratio of surfactant(s) to adalimumab of from about 1:3500 to about 15:1, more suitably from about 1:350 to about 6:1, more suitably from about 1:35 to about 3:1. In an embodiment, the surfactant(s) is present at a molar ratio of surfactant(s) to adalimumab of from about 2.1:1 to about 2.3:1, most suitably about 2.2:1. In an embodiment, polysorbate 80 is present at a molar ratio of polysorbate 80 to adalimumab of about 2.2:1.

As illustrated in the Example section, liquid pharmaceutical compositions of the invention including a surfactant as defined herein perform particularly well in stress tests, especially in relation to aggregation, fragmentation and protein unfolding, which can be important indicators of stability and drug product viability. Furthermore, liquid pharmaceutical compositions comprising polysorbate, particularly in an amount range as stipulated, perform particularly well.

Other Parameters Relating to the Invention

Osmolality

Suitably, the osmolality of the liquid pharmaceutical composition is between 200 and 400 mOsm/kg, more suitably between 220 and 390 mOsm/kg, more suitably between 230 and 350 mOsm/kg, more suitably between 240 and 340 mOsm/kg, more suitably between 260 and 320 mOsm/kg, most suitably between 280 and 310 mOsm/kg. Suitably the relative amounts and concentrations of the various components of the composition may be judiciously tuned to achieve the desired osmolality, and the particular novel combination of components allows this to be largely achieved without undermining other important parameters. However, suitably the relative amounts and concentrations of the various components of the composition may be selected so as to optimise other parameters—the present disclosure, including the examples and protocols set forth therein, enable the skilled person to achieve this end and to realise a, some, or all of the benefits of the present invention.

Protein Unfolding Temperature

Suitably, the protein unfolding temperature (suitably as measured via the DSF protocols defined herein) of adalimumab in the liquid pharmaceutical composition of the invention is greater than or equal to 65° C., more suitably greater than or equal to 70° C.

The novel combination of components present within the composition of the invention enables the skilled person to achieve high unfolding temperatures, which may be considered desirable from a thermal stability perspective.

Parameters when Subjected to Thermal Stress

Suitably the quantity (or concentration) of aggregates (suitably derived from adalimumab, and suitably as determined by the SE-HPLC protocols as defined herein) present within the liquid pharmaceutical composition increases by no more than a factor of 4 (i.e. 4 times the amount relative to an arbitrary start time) when the composition is thermally stressed at 40° C. (i.e. the composition is maintained at a temperature of 40° C.) over a period of 28 days, suitably by no more than factor of 3, suitably by no more than factor of 2.5, suitably by no more than factor of 2.2.

Suitably the quantity (or concentration) of fragments (suitably derived from adalimumab and suitably measured via the bioanalyzer protocols defined herein) present within the liquid pharmaceutical composition increases by no more than a factor of 4 (i.e. 4 times the amount relative to an arbitrary start time) when the composition is thermally stressed at 40° C. (i.e. the composition is maintained at a temperature of 40° C.) over a period of 28 days, suitably by no more than factor of 3, suitably by no more than factor of 2.5, suitably by no more than factor of 2.2.

Suitably the turbidity (suitably as measured via nephelometry in accordance with the protocols set forth herein) of the liquid pharmaceutical composition increases by no more than a factor of 2 (i.e. 2 times the amount relative to an arbitrary start time) when the composition is thermally stressed at 40° C. (i.e. the composition is maintained at a temperature of 40° C.) over a period of 28 days, suitably by no more than a factor of 1.5, suitably by no more than a factor of 1.2, and suitably the turbidity does not increase at all.

Suitably the pH of the liquid pharmaceutical composition changes (whether through increase or decrease, though generally by a decrease in pH) by no more than 0.5 pH units when the composition is thermally stressed at 40° C. (i.e. the composition is maintained at a temperature of 40° C.) over a period of 28 days, suitably by no more than 0.2 pH units, suitably by no more than 0.1 pH units, most suitably the pH does not change at all (to one decimal place).

Parameters when Subjected to Mechanical Stress

Suitably the quantity (or concentration) of aggregates (suitably derived from adalimumab, and suitably as determined by the SE-HPLC protocols as defined herein) present within the liquid pharmaceutical composition increases by no more than a factor of 2 (i.e. 2 times the amount relative to an arbitrary start time) when the composition is mechanically stressed (i.e. shaken as per the protocols outlined herein) over a period of 48 hours, suitably by no more than factor of 1.5, suitably by no more than factor of 1.2, suitably by no more than factor of 1.1.

Suitably the quantity (or concentration) of fragments (suitably derived from adalimumab and suitably measured via the bioanalyzer protocols defined herein) present within the liquid pharmaceutical composition increases by no more than a factor of 2 (i.e. 2 times the amount relative to an arbitrary start time) when the composition is mechanically stressed (i.e. shaken as per the protocols outlined herein) over a period of 48 hours, suitably by no more than factor of 1.5, suitably by no more than factor of 1.2, suitably by no more than factor of 1.1.

Suitably the turbidity (suitably as measured via nephelometry in accordance with the protocols set forth herein) of the liquid pharmaceutical composition increases by no more than a factor of 2 (i.e. 2 times the amount relative to an arbitrary start time) when the composition is mechanically stressed (i.e. shaken as per the protocols outlined herein) over a period of 48 hours, suitably by no more than factor of 1.5, suitably by no more than factor of 1.2, suitably by no more than factor of 1.1, and suitably the turbidity does not increase at all.

Suitably the pH of the liquid pharmaceutical composition changes (whether through increase or decrease, though generally by a decrease in pH) by no more than 0.5 pH units when the composition is mechanically stressed (i.e. shaken as per the protocols outlined herein) over a period of 48 hours, suitably by no more 0.2 pH units, suitably by no more than 0.1 pH units, most suitably the pH does not change at all (to one decimal place).

Parameters when Subjected to Light Stress

Suitably the quantity (or concentration) of aggregates (suitably derived from adalimumab, and suitably as determined by the SE-HPLC protocols as defined herein) present within the liquid pharmaceutical composition increases by no more than a factor of 50 (i.e. 50 times the amount relative to an arbitrary start time) when the composition is light stressed (i.e. the composition is exposed to light in accordance with protocols disclosed herein, i.e. 7 hours at 765 W/m$^2$), suitably by no more than factor of 45, suitably by no more than factor of 35, suitably by no more than factor of 30.

Suitably the quantity (or concentration) of fragments (suitably derived from adalimumab and suitably measured via the bioanalyzer protocols defined herein) present within the liquid pharmaceutical composition increases by no more than a factor of 4 (i.e. 4 times the amount relative to an arbitrary start time) when the composition is light stressed (i.e. the composition is exposed to light in accordance with protocols disclosed herein, i.e. 7 hours at 765 W/m$^2$), suitably by no more than factor of 3, suitably by no more than factor of 2.5, suitably by no more than factor of 2.

Suitably the turbidity (suitably as measured via nephelometry in accordance with the protocols set forth herein) of the liquid pharmaceutical composition increases by no more than a factor of 2 (i.e. 2 times the amount relative to an arbitrary start time) when the composition is light stressed (i.e. the composition is exposed to light in accordance with protocols disclosed herein, i.e. 7 hours at 765 W/m$^2$), suitably by no more than a factor of 1.5, suitably by no more than a factor of 1.2, and suitably the turbidity does not increase at all.

Suitably the pH of the liquid pharmaceutical composition changes (whether through increase or decrease, though generally by a decrease in pH) by no more than 0.5 pH units when the composition is light stressed (i.e. the composition is exposed to light in accordance with protocols disclosed herein, i.e. 7 hours at 765 W/m$^2$), suitably by no more than 0.2 pH units, suitably by no more than 0.1 pH units, most suitably the pH does not change at all (to one decimal place).

Suitably the isoform profile of adalimumab, particularly the integrated area of the "main peak", in the liquid pharmaceutical composition (suitably measured via isoelectronic focussing, suitably cIEF, suitably using an iCE280, suitably employing a protocol as set forth herein) is reasonably stable when the composition is light stressed (i.e. the composition is exposed to light in accordance with protocols disclosed herein, i.e. 7 hours at 765 W/m$^2$). Suitably, light stressing is performed in accordance with current ICH Q1B guidelines of the European Medicines Agency (in relation to photostability testing of new active substances and medicinal products), suitably as illustrated by document CPMP/ICH/279/95. Suitably the isoform profile of the adalimumab within the composition, as measured by reference to the integrated area of the "main peak" relating to the adalimumab in an electropherogram produced by isoelectronic focussing (suitably capillary isoelectronic focussing as described herein, or optionally other standard isoelectronic focussing protocols well known in the art), changes by no more than 20% when subjected to light stress (suitably 7 hours exposure to 765 W/m² light, suitably in accordance with current ICH Q1B guidelines of the European Medicines Agency, suitably document CPMP/ICH/279/95), especially where an adalimumab biosimilar is used. Suitably, the isoform profile of adalimumab within the composition (suitably measured by reference to the integrated area of the "main peak" relating to adalimumab) does not change by more than 15% (whether an increase or reduction in peak area) when light stressed in this manner (especially where an adalimumab biosimilar is used), suitably by no more than 10%, suitably by no more than 5%, suitably by no more than 4%, suitably by no more than 3%. Prior art adalimumab compositions exhibit inferior isoform profile stability due to photo-oxidation phenomenon which is duly inhibited through using an acetate buffer within the particular liquid pharmaceutical compositions of the invention. As such, in the liquid pharmaceutical compositions of the invention adalimumab exhibits superior photostability. In a particular embodiment, adalimumab has a photostability in the liquid pharmaceutical composition of the invention greater than commercial HUMIRA® formulations as defined herein (suitably as indicated by the relative isoform profiles, particularly in relation to the adalimumab main peak), suitably even where adalimumab biosimilars are used. It will be understood that the "main peak" corresponding to adalimumab refers to the main adalimumab peak of an electropherogram (i.e. that with the highest integrated peak area) resulting from isoelectronic focussing measurements, suitably performed as defined herein. Suitably the electropherogram is acquired at 280 nm, suitably over pre-focusing and focusing times of 1 and 6 minutes respectively, suitably at a voltage of 1500 V (pre-focusing) and 3000 V (focusing). Suitably the peaks are absorbance peaks, suitably at 280 nm. The separation of the various isoforms is suitably achieved using 100 mM sodium hydroxide (in 0.1% methyl cellulose) as a cathodic solution and suitably 80 mM o-phosphoric acid (in 0.1% methyl cellulose) as an anodic solution. Suitably samples for isoelectronic focussing measurements are prepared according to a protocol defined herein or elsewhere in the art, but in particular may suitably involve one or more of all of: i) purification; ii) removal of salts (e.g. with centrifugation, suitably with a cut off at 10 kDa); iii) pre dilution to give a protein content of approximately 5.0 mg/mL, suitably approximately 1.0 mg/mL, wherein the diluent may optionally include methyl cellulose, Pharmalyte 5-8 (GE Healthcare), Pharmalyte 8-10.5 (GE Healthcare), low pI marker 7.05 (Protein Simple), high pI marker 9.50 (Protein Simple) and purified water; iv) one or more additional centrifugation steps (e.g. 3 mins at 10000 rpm, suitably followed by 2 mins at 7000 rpm, suitably on a 150 micolitre sample). The isoelectronic focussing is suitably capillary isoelectron focussing (cIEF), and is suitably performed using an iCE280 system by Protein Simple.

Parameters when Subjected to Freeze/Thaw Cycles

Suitably the quantity (or concentration) of aggregates (suitably derived from adalimumab, and suitably as determined by the SE-HPLC protocols as defined herein) present within the liquid pharmaceutical composition increases by no more than a factor of 1.5 (i.e. 1.5 times the amount relative to an arbitrary start time) when the composition is subjected to five freeze/thaw cycles (i.e. the composition is frozen and thawed five times in accordance with protocols disclosed herein, i.e. −80° C. to 20° C. five times), suitably by no more than factor of 1.2, suitably by no more than factor of 1.1, suitably by there is (substantially) no increase at all in the quantity (or concentration) of aggregates.

Suitably the quantity (or concentration) of sub-visible particles or precipitates, with a particle size less than or equal to 25 microns, present within the liquid pharmaceutical composition increases by no more than a factor of 4 (i.e. 4 times the amount relative to an arbitrary start time) when the composition is subjected to five freeze/thaw cycles (i.e. the composition is frozen and thawed five times in accordance with protocols disclosed herein, i.e. −80° C. to 20° C. five times), suitably by no more than factor of 3, suitably by no more than factor of 2.5, suitably by no more than factor of 2.2. Suitably the quantity (or concentration) of sub-visible particles or precipitates, with a particle size less than or equal to 10 microns, present within the liquid pharmaceutical composition increases by no more than a factor of 4 (i.e. 4 times the amount relative to an arbitrary start time) when the composition is subjected to five freeze/thaw cycles (i.e. the composition is frozen and thawed five times in accordance with protocols disclosed herein, i.e. −80° C. to 20° C. five times), suitably by no more than factor of 3, suitably by no more than factor of 2.5, suitably by no more than factor of 2.2.

Suitably the quantity (or concentration) of sub-visible particles or precipitates, with a particle size less than or equal to 25 microns, present within the liquid pharmaceutical composition increases by no more than a factor of 4 (i.e. 4 times the amount relative to an arbitrary start time) when the composition is subjected to 5 freeze/thaw cycles, suitably by no more than factor of 3, suitably by no more than factor of 2.5, suitably by no more than factor of 2.2. Suitably the quantity (or concentration) of sub-visible particles or precipitates, with a particle size less than or equal to 10 microns, present within the liquid pharmaceutical composition increases by no more than a factor of 4 (i.e. 4 times the amount relative to an arbitrary start time) when the composition is subjected to 5 freeze/thaw cycles, suitably by no more than factor of 3, suitably by no more than factor of 2.5, suitably by no more than factor of 2.2.

Methods of Stabilising Antibody

In view of the aforementioned points in this sub-section, and the data presented in the examples, the present invention also provides a method of stabilising liquid adalimumab compositions (chemically and/or physically optionally in relation to any one or more of the aforementioned parameters/properties), comprising mixing with adalimumab with any relevant components required to form a liquid pharmaceutical composition as defined herein. Different embodiments will suitably require different combinations of components to be mixed, potentially in different amounts, and the skilled person can readily deduce such combinations and amounts by reference to the foregoing disclosure relating to the liquid pharmaceutical composition. Such different combinations of components may stabilise liquid adalimumab compositions in different respects. For instance, mixing adalimumab with the aforementioned components to form a liquid pharmaceutical composition as defined herein may stabilise adalimumab by:

i) Increasing the protein unfolding temperature of adalimumab;
ii) Inhibiting the formation of aggregates;
iii) Inhibiting the formation of fragments;
iv) Inhibiting the formation of sub-visible particles (either 25 microns or microns);
v) Inhibiting turbidification;
vi) Inhibiting pH changes;
vii) Inhibiting photo-oxidation; and/or viii) Reducing instability upon freeze/thaw cycles.

As such, the present invention provides a method of achieving one, some, or all of the following benefits:
i) Increased protein unfolding temperatures for adalimumab;
ii) Inhibition of formation of aggregates;
iii) Inhibition of formation of fragments;
iv) Inhibition of formation of sub-visible particles (either 25 microns or microns);
v) Inhibition of turbidification;
vi) Inhibition of pH changes;
vii) Inhibition of photo-oxidation;
viii) Reduced instability upon freeze/thaw cycles; and/or
ix) Stabilisation of the isoform profile (especially with respect to the "main peak" as defined herein);

the method comprising manufacturing a liquid pharmaceutical composition of adalimumab as defined herein.

Suitably, the liquid pharmaceutical compositions of the invention have a shelf life of at least 6 months, suitably at least 12 months, suitably at least 18 months, more suitably at least 24 months. Suitably, the liquid pharmaceutical compositions of the invention have a shelf life of at least 6 months, suitably at least 12 months, suitably at least 18 months, more suitably at least 24 months, at a temperature of 2-8° C.

Enabling the Skilled Person to Optimise Key Stability Properties

The novel combination of components disclosed for use in liquid pharmaceutical compositions of the invention enables the skilled person to produce (and judiciously fine-tube) compositions which exhibit comparable or enhanced properties relative to compositions of the prior art. In particular, the present disclosure now provides the skilled person with all the necessary tools to optimise formulation stability, and in particular optimise one or more of: inhibition of aggregation, fragmentation, protein unfolding, precipitation, pH slippage, and oxidation (especially photo-oxidation). Furthermore, the skilled person is given guidance on how to achieve such optimisations (through judiciously varying the compositions) and how, in the process, to minimise any detrimental side-effects. The present disclosure enables the skilled person to work across the scope of the invention to produce a variety of specific compositions which exhibit comparable or improved properties relative to compositions of the prior art, and this can be achieved using fewer components.

Particular Embodiments

In an embodiment, the liquid pharmaceutical composition comprises:
adalimumab;
an acetate buffering agent (e.g. sodium acetate) (or an acetate buffer system);
a sugar stabiliser (e.g. trehalose); and
a surfactant (e.g. polysorbate 80).

In an embodiment, the liquid pharmaceutical composition comprises:
adalimumab;
an acetate buffering agent (e.g. sodium acetate) (or an acetate buffer system);
a sugar stabiliser (e.g. trehalose);
a tonicifier (e.g. sodium chloride); and
optionally a surfactant (e.g. polysorbate 80).

In an embodiment, the liquid pharmaceutical composition comprises adalimumab, acetate buffer system, and a sugar stabiliser in a molar ratio of 1:14-40:288-865 respectively. In an embodiment, the liquid pharmaceutical composition comprises adalimumab, acetate buffer system, sugar stabiliser, and a tonicifier in a molar ratio of 1:14-40:288-865: 28-576 respectively. In an embodiment, the liquid pharmaceutical composition comprises adalimumab, acetate buffer system, sugar stabiliser, tonicifier, and surfactant in a molar ratio of 1:14-40:288-865: 28-576:0.1-3.2 respectively.

In an embodiment, the liquid pharmaceutical composition comprises adalimumab, acetate buffer system, and a sugar stabiliser in a molar ratio of 1:14-40:548-605 respectively. In an embodiment, the liquid pharmaceutical composition comprises adalimumab, acetate buffer system, sugar stabiliser, and a tonicifier in a molar ratio of 1:14-40:548-605: 115-173 respectively. In an embodiment, the liquid pharmaceutical composition comprises adalimumab, acetate buffer system, sugar stabiliser, tonicifier, and surfactant in a molar ratio of 1:14-40:548-605: 115-173:2-2.4 respectively.

In an embodiment, the liquid pharmaceutical composition comprises adalimumab, sodium acetate/acetic acid buffer system, and trehalose in a molar ratio of 1:5.7-145: 288-865 respectively. In an embodiment, the liquid pharmaceutical composition comprises adalimumab, sodium acetate/acetic acid buffer system, trehalose, and sodium chloride in a molar ratio of 1:5.7-145: 288-865:28-576 respectively. In an embodiment, the liquid pharmaceutical composition comprises adalimumab, sodium acetate/acetic acid buffer system, trehalose, sodium chloride, and polysorbate 80 in a molar ratio of 1:5.7-145: 288-865:28-576:0.002-11 respectively.

In an embodiment, the liquid pharmaceutical composition comprises adalimumab, sodium acetate/acetic acid buffer system, and trehalose in a molar ratio of 1:14-40:548-605 respectively. In an embodiment, the liquid pharmaceutical composition comprises adalimumab, sodium acetate/acetic acid buffer system, trehalose, and sodium chloride in a molar ratio of 1:14-40:548-605: 115-173 respectively. In an embodiment, the liquid pharmaceutical composition comprises adalimumab, sodium acetate/acetic acid buffer system, trehalose, sodium chloride, and polysorbate 80 in a molar ratio of 1:14-40:548-605: 115-173:2-2.4 respectively.

In an embodiment, the liquid pharmaceutical composition comprises adalimumab, sodium acetate/acetic acid buffer system, and trehalose in a molar ratio of 1:28.8:576 respectively. In an embodiment, the liquid pharmaceutical composition comprises adalimumab, sodium acetate/acetic acid buffer system, trehalose, and sodium chloride in a molar ratio of 1:28.8:576:144 respectively. In an embodiment, the liquid pharmaceutical composition comprises adalimumab, sodium acetate/acetic acid buffer system, trehalose, sodium chloride, and polysorbate 80 in a molar ratio of 1:28.8:576: 144:2.2 respectively.

In an embodiment, the liquid pharmaceutical composition comprises adalimumab, acetate buffering species, and trehalose in a weight ratio of 25-75:0.12-3.0:15-140 respectively. In an embodiment, the liquid pharmaceutical composition comprises adalimumab, acetate buffering species, trehalose, and sodium chloride in a weight ratio of 25-75:0.12-3.0:15-140:0.5-12 respectively. In an embodiment, the liquid pharmaceutical composition comprises adalimumab, acetate buffering species, trehalose, sodium chloride, and polysorbate 80 in a weight ratio of 25-75:0.12-3.0:15-140:0.5-12: 0.01-2 respectively.

In an embodiment, the liquid pharmaceutical composition comprises adalimumab, acetate buffering species, and trehalose in a weight ratio of 45-55:0.30-0.84:65-72 respectively. In an embodiment, the liquid pharmaceutical composition comprises adalimumab, acetate buffering species, trehalose, and sodium chloride in a weight ratio of 45-55:0.30-0.84: 65-72:2.7-3.1 respectively. In an embodiment, the liquid pharmaceutical composition comprises adalimumab, acetate buffering species, trehalose, sodium chloride, and polysorbate 80 in a weight ratio of 45-55:0.30-0.84:65-72:2.7-3.1:0.9-1.1 respectively.

In an embodiment, the liquid pharmaceutical composition comprises adalimumab, acetate buffering species, and trehalose in a weight ratio of 50:0.6:68 respectively. In an embodiment, the liquid pharmaceutical composition comprises adalimumab, acetate buffering species, trehalose, and sodium chloride in a weight ratio of 50:0.6:68:2.9 respectively. In an embodiment, the liquid pharmaceutical composition comprises adalimumab, acetate buffering species, trehalose, sodium chloride, and polysorbate 80 in a weight ratio of 50:0.6:68:2.9:1 respectively.

Any of the aforementioned embodiments relating to molar and/or weight ratios of the various components may be additionally defined by reference to the (substantial or entire) absence or low levels of component(s) such as arginine, amino acids, surfactants (optionally with the exception of polysorbate 80), and/or phosphate buffering agents/systems, as defined anywhere herein.

It will be appreciated that the buffering agent (e.g. sodium acetate) or buffer system (e.g. sodium acetate/acetic acid) of any of the aforementioned embodiments may be directly incorporated into the compositions or may be produced in situ, for instance, via an acid base reaction, suitably by reacting a conjugate acid of the buffering agent (e.g. acetic acid) with a base (e.g. sodium hydroxide). Regardless of the method used to provide or produce the buffering agent or buffer system, suitably the resulting composition ultimately comprises an appropriate balance of the buffering agent and any acid/base conjugate to furnish the desired pH. The skilled person will be readily able to calculate or experimentally determine, without undue effort, the appropriate balance of buffering agent and acid/base conjugate, and/or the amount of base which needs to be added to a conjugate acid in order to produce the appropriate amount of buffering agent and furnish the desired pH.

In an embodiment, the liquid pharmaceutical composition comprises:
  adalimumab;
  an acetate buffering agent (e.g. sodium acetate) (or acetate buffer system);
  a sugar stabiliser (e.g. trehalose);
  a tonicifier (e.g. sodium chloride);
  optionally a surfactant (e.g. polysorbate 80); and
  water (for injection);
  wherein the composition:
    is (substantially or entirely) free of arginine (suitably L-arginine); comprises arginine in a concentration of at most 0.1 mM;
    is (substantially or entirely) free of amino acids or comprises one or more amino acids in a (collective) concentration of at most 0.1 mM;
    is (substantially or entirely) free of surfactants with the optional exception of polysorbate 80 or comprises one or more of said surfactants (optionally excluding polysorbate 80) in a (collective) concentration of at most 1 mM; and/or
    is (substantially or entirely) free of phosphate buffering agents (e.g. sodium dihydrogen phosphate, disodium hydrogen phosphate) or comprises a phosphate buffer system in a concentration of at most 0.1 mM.

In an embodiment, the liquid pharmaceutical composition comprises:
  Adalimumab (suitably in a concentration as defined herein);
  5 to 14 mM acetate buffer system (e.g. sodium acetate/acetic acid);
  100 to about 300 mM a sugar stabiliser (e.g. trehalose);
  10 to about 200 mM a tonicifier (e.g. sodium chloride);
  (optionally) 0.05 mg/mL to about 1.5 mg/mL surfactant (e.g. polysorbate 80); and
  water (for injection);
  wherein the composition:
    has a pH between 5.0 and 6.7 (e.g. pH 5.2)
    is (substantially or entirely) free of arginine (suitably L-arginine); comprises arginine in a concentration of at most 0.1 mM;
    is (substantially or entirely) free of amino acids or comprises one or more amino acids in a (collective) concentration of at most 0.1 mM;
    is (substantially or entirely) free of surfactants with the optional exception of polysorbate 80 or comprises one or more of said surfactants (optionally excluding polysorbate 80) in a (collective) concentration of at most 1 mM; and/or
    is (substantially or entirely) free of phosphate buffering agents (e.g. sodium dihydrogen phosphate, disodium hydrogen phosphate) or comprises a phosphate buffer system in a concentration of at most 0.1 mM.

In an embodiment, the liquid pharmaceutical composition comprises:
  25 to about 75 mg/mL adalimumab;
  2 to about 50 mM sodium acetate/acetic acid buffer system;
  100 to about 300 mM trehalose;
  10 to about 200 mM sodium chloride;
  0.001 mg/mL to about 5 mg/mL polysorbate 80; and
  water (for injection);
  wherein the composition:
    has a pH between 5.0 and 5.5;
    is (substantially or entirely) free of arginine (suitably L-arginine) or comprises arginine in a concentration of at most 0.1 mM;
    is (substantially or entirely) free of amino acids or comprises one or more amino acids in a (collective) concentration of at most 0.1 mM;
    is (substantially or entirely) free of surfactants with the exception of polysorbate 80 or comprises one or more of said surfactants (excluding polysorbate 80) in a (collective) concentration of at most 1 mM; and/or
    is (substantially or entirely) free of phosphate buffering agents (e.g. sodium dihydrogen phosphate, disodium hydrogen phosphate) or comprises a phosphate buffer system in a concentration of at most 0.1 mM.

In an embodiment, the liquid pharmaceutical composition comprises:
  45 to about 55 mg/ml adalimumab;
  5 to 14 mM sodium acetate/acetic acid buffer system;
  190 to 210 mM trehalose;
  40 to 60 mM sodium chloride;
  0.9 mg/mL and 1.1 mg/mL polysorbate 80; and
  water (for injection);
  wherein the composition:
    has a pH between 5.1 and 5.3;
    is (substantially or entirely) free of arginine (suitably L-arginine) or comprises arginine in a concentration of at most 0.001 mM;
    is (substantially or entirely) free of amino acids or comprises one or more amino acids in a (collective) concentration of at most 0.001 mM.

is (substantially or entirely) free of surfactants with the exception of polysorbate 80 or comprises one or more of said surfactants (excluding polysorbate 80) in a (collective) concentration of at most 0.0001 mM; and/or is (substantially or entirely) free of phosphate buffering agents (e.g. sodium dihydrogen phosphate, disodium hydrogen phosphate) or comprises a phosphate buffer system in a concentration of at most 0.001 mM.

In an embodiment, the liquid pharmaceutical composition comprises:
50 mg/ml adalimumab;
10 mM sodium acetate/acetic acid buffer system;
200 mM trehalose;
50 mM sodium chloride;
1.0 mg/mL polysorbate 80; and
water (for injection);
wherein the composition:
has a pH of 5.2;
is free of arginine;
is free of amino acids;
is free of surfactants with the exception of polysorbate 80; and
is free of phosphate buffering agents/systems.

Preferably, the liquid pharmaceutical composition consists essentially of:
25 to about 75 mg/mL adalimumab;
2 to about 50 mM sodium acetate/acetic acid buffer system;
100 to about 300 mM trehalose;
10 to about 200 mM sodium chloride;
0.001 mg/mL to about 5 mg/mL polysorbate 80; and
water (for injection);
wherein the composition has a pH between 5.0 and 5.5.

More preferably, the liquid pharmaceutical composition consists essentially of:
40 to about 60 mg/mL adalimumab;
5 to about 15 mM sodium acetate/acetic acid buffer system;
175 to about 225 mM trehalose;
25 to about 75 mM sodium chloride;
0.5 mg/mL to about 1.5 mg/mL polysorbate 80; and
water (for injection);
wherein the composition has a pH between 5.1 and 5.3.

Ideally, the liquid pharmaceutical composition consists essentially of:
50 mg/mL adalimumab;
10 mM sodium acetate/acetic acid buffer system;
200 mM trehalose;
50 mM sodium chloride;
1 mg/mL polysorbate 80; and
water (for injection);
wherein the composition has a pH of 5.2.

Suitably, the liquid pharmaceutical composition may be as set forth in any of the preceding embodiments, except that the absence or low levels of component(s) such as arginine, amino acids, surfactants (optionally with the exception of polysorbate 80), and phosphate buffering agents/systems, rather than being defined by reference to concentration(s) (i.e. molarity) may instead be defined by reference to corresponding molar ratios of the component to buffer system; corresponding weight ratios of the component to adalimumab; or corresponding molar ratios of the component to adalimumab. The skilled person will readily deduce for each component, from the relevant section of this specification relating to that specific component, which molar and weight ratios correspond to which concentrations, since herein the relevant molar and weight ratios are listed to respectively correspond to given concentrations. For example, in the case of arginine, the optional concentrations of "at most 0.1 mM, more suitably at most 0.01 mM, most suitably at most 0.001 mM" respectively correspond with a molar ratio of arginine to buffer system of "at most 1:150 . . . more suitably at most 1:1500, most suitably at most 1:15,000"; with "a weight ratio of arginine to adalimumab of at most 1:3000 . . . more suitably at most 1:30,000, most suitably at most 1:300,000"; and with a molar ratio of arginine to adalimumab of at most 1:3.75 . . . more suitably at most 1:37.5, most suitably at most 1:375". The same correspondences apply for amino acids, surfactants, and phosphate buffering agents/systems.

Method of Manufacturing a Liquid Pharmaceutical Composition

The present invention provides a method of manufacturing a liquid pharmaceutical composition, suitably as defined herein. The method suitably comprises mixing together, in any particular order deemed appropriate, any relevant components required to form a liquid pharmaceutical composition as defined herein. The skilled person may refer to the Examples or techniques well known in the art for forming liquid pharmaceutical compositions (especially those for injection via syringe). Different embodiments will suitably require different combinations of components to be mixed, potentially in different amounts. The skilled person can readily deduce such combinations and amounts by reference to the foregoing disclosure relating to the liquid pharmaceutical composition.

Suitably the method involves mixing together the relevant components suitably, in a diluent (e.g. water), suitably so that all of the components are (substantially or entirely) dissolved in the diluent.

The method may involve first preparing a pre-mixture (or pre-solution) of some or all components (optionally with some or all of the diluent) excluding adalimumab, and adalimumab may then itself (optionally with or pre-dissolved in some of the diluent) be mixed with the pre-mixture (or pre-solution) to afford the liquid pharmaceutical composition, or a composition to which final components are then added to furnish the final liquid pharmaceutical composition. Most suitably, the pre-mixture contains all components except for the adalimumab and optionally also some diluent (which may be used to pre-dissolve adalimumab), suitably so that adalimumab is added to a mixture which offers optimal stabilisation of adalimumab. Suitably the aforementioned pre-mixture is prepared with the desired pH for the final liquid pharmaceutical formulation.

Suitably, the method involves forming a buffer system, suitably a buffer system comprising a buffering agent as defined herein. The buffer system is suitably formed in a pre-mixture prior to the addition of adalimumab, though the buffer system may optionally be formed with adalimumab present. The buffer system may be formed through simply mixing the buffering agent (supplied ready-made) with its acid/base conjugate (suitably in appropriate relative quantities to provide the desired pH—this can be determined by the skilled person either theoretically or experimentally). In the case of an acetate buffer system, this means mixing sodium acetate with acetic acid. Alternatively, the buffer system may be formed through adding a strong acid (e.g. HCl) to the buffering agent (e.g. sodium acetate) in order to form in situ the acid/base conjugate (e.g. acetic acid) (again suitably in appropriate relative quantities to provide the desired pH). Alternatively, the buffer system may be formed through adding a strong base (e.g. sodium hydroxide) to the acid/base conjugate (e.g. acetic acid) of the buffering agent (e.g. sodium acetate) in order to form in situ the buffering agent (again suitably in appropriate relative quantities to provide the desired pH). The pH of either the pre-mixture of final liquid pharmaceutical composition may be judiciously adjusted by adding the required quantity of strong base or strong acid, or even a quantity of buffering agent or acid/base conjugate.

In certain embodiments, the buffering agent and/or buffer system is pre-formed as a separate mixture, and the buffer system is transferred to a precursor of the liquid pharmaceutical composition (comprising some or all components save for the buffering agent and/or buffer system, suitably comprising adalimumab and potentially only adalimumab) via buffer exchange (e.g. using diafiltration until the relevant concentrations or osmolality is reached). Additional excipients may be added thereafter if necessary in order to produce the final liquid pharmaceutical composition. The pH may be adjusted once or before all the components are present.

Any, some, or all components may be pre-dissolved or pre-mixed with a diluent prior to mixing with other components.

The final liquid pharmaceutical composition may be filtered, suitably to remove particulate matter. Suitably filtration is through filters sized at or below 1 μm, suitably at 0.22 μm. Suitably, filtration is through either PES filters or PVDF filters, suitably with 0.22 μm PES filters.

The present invention also provides a liquid pharmaceutical composition obtainable by, obtained by, or directly obtained by the method of manufacture herein described.

Drug-Delivery Device

The present invention provides a drug delivery device comprising a liquid pharmaceutical composition as defined herein. Suitably the drug delivery device comprises a chamber within which the pharmaceutical composition resides. Suitably the drug delivery device is sterile.

The drug delivery device may a vial, ampoule, syringe, injection pen (e.g. essentially incorporating a syringe), or intravenous bag. Most suitably the drug delivery device is a syringe, suitably an injection pen. Suitably the syringe is a glass syringe. Suitably the syringe comprises a needle, suitably a 29 G1/2" needle.

The present invention provides a method of manufacturing a drug delivery device, suitably as defined herein, the method comprising incorporating a liquid pharmaceutical composition as defined herein within a drug delivery device. Such manufacture typically involves charging the liquid pharmaceutical composition as defined herein to a syringe, suitably via a needle affixed thereto. The needle may thereafter be removed, replaced, or remain.

According to an eleventh aspect of the present invention there is provided a drug delivery device obtainable by, obtained by, or directly obtained by a method of manufacture defined herein.

Package

The present invention provides a package comprising a liquid pharmaceutical composition as defined herein. Suitably the package comprises a drug delivery device as defined herein, suitably a plurality of drug delivery devices. The package may comprise any suitable container for containing one or more drug delivery devices.

The present invention provides a method of manufacturing a package, the method comprising incorporating a liquid pharmaceutical composition as defined herein within a package. Suitably this is achieved by incorporating said liquid pharmaceutical composition within one or more drug delivery devices, and thereafter incorporating the one or more pre-filled drug delivery devices into a container present within the package.

The present invention provides a package obtainable by, obtained by, or directly obtained by a method of manufacture defined herein.

Kit of Parts

The present invention provides a kit of parts comprising a drug delivery device (without the liquid pharmaceutical composition incorporated therein), a liquid pharmaceutical composition as defined herein (optionally contained in a separate package or container), and optionally a set of instructions with directions regarding the administration (e.g. sub-cutaneous) of the liquid pharmaceutical composition. The user may then fill the drug delivery device with the liquid pharmaceutical composition (which may be provided in a vial or ampoule or such like) prior to administration.

Uses of Pharmaceutical Liquid Composition and Methods of Treatment

According to a twelfth aspect of the present invention there is provided a method of treating a disease or medical disorder; a liquid pharmaceutical composition for use in therapy; a use of a liquid pharmaceutical composition in the manufacture of a medicament for the treatment of a disease or disorder; a method of treating a tumour necrosis factor-alpha (TNF-α)-related autoimmune disease; a liquid pharmaceutical composition for use in the treatment of a tumour necrosis factor-alpha (TNF-α)-related autoimmune disease; a use of a liquid pharmaceutical composition in the manufacture of a medicament for the treatment of a tumour necrosis factor-alpha (TNF-α)-related autoimmune disease; a method of treating rheumatoid arthritis, psoriatic arthritis, ankylosing spondylitis, Crohn's disease, ulcerative colitis, moderate to severe chronic psoriasis and/or juvenile idiopathic arthritis; a liquid pharmaceutical composition for use in the treatment of rheumatoid arthritis, psoriatic arthritis, ankylosing spondylitis, Crohn's disease, ulcerative colitis, moderate to severe chronic psoriasis and/or juvenile idiopathic arthritis; and a use of a liquid pharmaceutical composition in the manufacture of a medicament for the treatment of rheumatoid arthritis, psoriatic arthritis, ankylosing spondylitis, Crohn's disease, ulcerative colitis, moderate to severe chronic psoriasis and/or juvenile idiopathic arthritis; as defined herein.

The liquid pharmaceutical compositions defined herein may be used to treat any one or more of the aforementioned diseases or medical disorders. In a particular embodiment, the liquid pharmaceutical compositions are used to treat rheumatoid arthritis, Crohn's disease and psoriasis.

The liquid pharmaceutical compositions are suitably parenterally administered, suitably via sub-cutaneous injection.

EXAMPLES

Materials and Equipment

The following materials were used in the preparation of formulations described in the Examples that follow:

| Ingredient |
| --- |
| Acetic acid (glacial) 100% |
| Adalimumab DS |
| Arginine monohydrochloride |
| Aspartic Acid |
| Citric Acid Monohydrate |
| Dibasic sodium phosphate |

| Ingredient |
|---|
| dihydrate |
| Lysine hydrochloride |
| Mannitol |
| Monobasic sodium phosphate dihydrate |
| Poloxamer 188 |
| Polysorbate 80 |
| Sodium chloride |
| Sodium citrate |
| Sodium hydroxide solution 30% |
| Trehalose dihydrate |
| WFI |

The following disposable equipment and materials were used in the Examples and Screen Experiments which follow.

| Item | Code | Supplier |
|---|---|---|
| Eppendorf Tubes (0.5 mL, 1.5 mL, 2.0 mL) | NA | Eppendorf |
| Falcon | 352096 (15 mL), 352070 (50 mL) polypropylene tubes | Becton Dickinson |
| PES membrane (0.22 μm) filter unit | MillexGP Express PES membrane REF SLGP033RS | Millipore |
| PETG bottles | 3420-1000, 3420-0500, 2019-0250, 3420-0125, 3420-0060, 2019-0030 | Nalgene |

The following packaging was used in the Examples and Screen Experiments which follow.

| Item | Code | Supplier |
|---|---|---|
| DIN2R Type I glass vial | 0212060.6112 11200000A | Nuova Ompi |
| 1 mL stopper | S2-F451 RSV; D 21-7S RB2-40 | Daikyo Seiko, LTD |
| 13 mm flip-off cap | 12000350 | MS-A |

The following equipment was used in the Examples and Screen Experiments which follow.

| Item | Mod. | Manufacturer |
|---|---|---|
| Analytical scales | AX205, PG2002-S | Mettler Toledo |
| Benchtop xenon instrument | Suntest CPS+ | Atlas |
| Calibrated pipettes | P20, P100, P200, P1000 | Gilson |
| HPLC | Alliance | Waters |
| iCE280 | Fast IEF Analyzer | Convergent Bioscience |
| Osmometer | Osmomat 030/D | Gonotec |
| PCR | 7500 Fast Real-Time | AB Applied Biosystem |
| pH meters | Seven Multi | Mettler Toledo |
| Refrigerators | +2-8° C. | Angelantoni |
| Software Design Expert | ver. 7.1.5 | Stat-Ease, Inc. |
| Thermostatic cabinets | +25° C., +40° C. | Angelantoni |
| Turbidimeter | 2100AN IS | Hach Lange |
| UV Spectrophotometer | Lambda 35 | Perkin Elmer |

Analytical Techniques and Protocols

The following analytical methods of protocols were employed, in the Examples and Screening Experiments which follow, for the reasons stated in the table below:

| Method No. | Analytical Method | Scope of the test |
|---|---|---|
| 1 | Bioanalyzer | Purity |
| 2 | DSF | Unfolding temperature |
| 3 | iCE280 | Isoforms profile |
| 4 | OD | Protein Content |
| 5 | SE-HPLC | Aggregates determination |
| 6 | Nephelometry | Turbidity |
| 7 | Osmolality | Osmolality of solution |
| 8 | pH | pH determination |
| 9 | Sub-visible particles | Particle count |

The individual protocols for each of the above analytical methods are described in turn below, and references in the Examples and Screening Experiments to any such analytical methods used these protocols.

1. Purity—Bioanalyzer

A 2100 Bioanalyzer was used. Protocols can be found in the relevant instruction manual. However, the protocols have been additionally refined as follows.

Solutions:

Gel-Dye Mix (Staining Solution):

Add 25 μL of 230plus dye concentrate to a protein 230plus gel matrix tube.

Vortex well, and spin down the tube for 15 seconds. Transfer to a spin filter and centrifuge at 2500 rpm for at least 20 min. The solution is ready to use. Store the solution at +5±3° C. for not more than 4 weeks.

Destaining Solution:

Pipette 650 μL of gel matrix into a spin filter. Centrifuge at 2500 rpm for at least 25 min. Store the solution at +5±3° C. for not more than 4 weeks.

Sample Buffer:

It is recommended to divide the 200 μL of sample buffer into aliquots of 25 μL and defreeze aliquot for each chip. Store the Sample buffer stock solution and the aliquots at −20° C., not longer than the expiring date provided by the supplier.

Maleimide Stock Solution:

Dissolve 23.4 mg of Male imide in 1 mL MilliQ water (O.24M). Vortex well the solution. Subsequently dilute the solution 1:4 with MilliQ water. (e.g. 50 μL Stock Sol.+150 μL MilliQ). The final concentration of the diluted Maleimide solution is 60 mM. (Since no data is available yet on the stability of this solution, it must be prepared freshly before starting each analytical session).

OTf-Solution:

For the analysis of Adalimumab samples the reducing solution must be prepared with 1M DTT, therefore dissolve 154.0 mg DTT in 1 mL MilliQ Water.

Non-Reducing Solution:

Add 1 μl. of MilliQ water to a sample buffer aliquot (25 4) and vortex for 5 seconds. Use the non-reducing solution within its preparation day.

Reducing Solution:

Add 1 μl, of the according DTf-Solution to a sample buffer aliquot (25 μL) and vortex for 5 seconds. Use the reducing solution within its preparation day.

Sample Preparation:

Samples are analysed at the concentration ranging between 2.4-3 mg/ml.

If it's necessary the samples can be diluted to the target concentration using Milli Q water.

Samples are prepared according to the Reagent Kit Guide using the reducing and non-reducing sample buffers according to the instruction in the Reagent Kit Guide and also mentioned above. It is strongly recommended to use, differently from the guide, greater volumes to achieve reproducible and accurate results. An example how to prepare the ladder and the samples is reported below:

Sample Preparation Solution Reducing and Non Reducing Condition

| Reagent | Volume μL | Total Volume μL |
|---|---|---|
| Sample diluted at 3 mg/mL | 3 μL | 6 μL |
| Sample buffer (reducing or not reducing) | 2 μL | |
| Maleimide solution | 1 μL | |
| Samples have to be mixed (via vortex) well and spun down | | |
| All samples and the Ladder are heated 5 minutes at 70° C. | | |
| MilliQ water | 84 μL | 90 μL |
| Vortex well and spin down | | |
| Loading 6 μL all Sample and Ladder | | |

Note 1: For the IPCs whose concentration is between 2.4 mg/ml and 3.0 mg/mL, the sample preparation follows the table above but the volume of MilliQ Water added after sample heating is calculated in order to reach a final protein concentration of 0.1 mg/ml.

An example of sample preparation for a sample having concentration between 2.4 and 3.0 mg/mL, is reported here below:

Sample Preparation Solution Reducing and Non Reducing Condition

| Reagent | Volume μL | Total Volume μL |
|---|---|---|
| Sample (2.6 mg/mL) | 3 μL | 6 μL |
| Sample buffer (reducing or not reducing) | 2 μL | |
| Maleimide solution | 1 μL | |
| Samples have to be mixed (via vortex) well and spun down | | |
| All samples and the Ladder are heated 5 minutes at 70° C. | | |
| MilliQ water | 72 μL | 78 μL |
| vortex well and spin down | | |
| Loading 6 μL all Sample and Ladder | | |

Note 2: AH wells have to be loaded. If the sample number is lower than the available wells, the empty wells can be used for additional duplicates or blank samples.

Preparing the System and the Chip:
  To clean the system before and as well after an analysis fill the "Electrode Cleaner" with 600IIL MilliQ Water and place it into the Agilent 2100 Bioanalyzer, close the lid and let the system cease. No further action is required.
  Adjust the base-plate of the chip priming station to position "A" and the syringe clip to its middle position.

Preparing the Ohio

| System Preparation |
|---|
| Insert a new Protein Chip in the priming station |
| Pipette 12 μL of Gel-Dye Mix in the well marked G (Up right) |
| Set the plunger at 1 mL and close the chip priming station |
| Press the plunger until it is held by the clip |
| Wait 60 seconds and then release the clip |
| Wait 5 seconds and slowly pull back the plunger to the 1 mL mark |
| Open the chip priming station |
| Remove the solution in this well |

| System Preparation |
|---|
| Pipette 12 μL of Gel-Dye Mix in the well marked G (Up right) and in all remaining wells marked with G |
| Pipette 12 μL of Destaining Solution in the well marked with DS |

Loading of the Ladder and the Sample:
  Transfer 6 μL of each sample into a sample well and as well 6 μL of the ladder in the dedicated well, which is clearly indicated with a ladder symbol.
  Place the chip into the Agilent 2100 Bioanalyzer and start the analysis within 5 min.

Example of Sample Set

| Well | Sample | Amount μL |
|---|---|---|
| 1 | Blank | 6 |
| 2 | Blank | 6 |
| 3 | Unknown sample1 rep1 | 6 |
| 4 | Unknown sample1 rep2 | 6 |
| 5 | Unknown sample2 rep1 | 6 |
| 6 | Unknown sample2 rep2 | 6 |
| 7 | Unknown sample3 rep1 | 6 |
| 8 | Unknown sample3 rep2 | 6 |
| 9 | Current Reference Material Rep 1 | 6 |
| 10 | Current Reference Material Rep 1 | 6 |
| Ladder | Ladder | 6 |

Data Analysis and Evaluation of the Results:
  To gain results the following minimum operations have to be executed
    Place the chip in the specific spot and close the lid.
    In the instrument context select Assay—Electrophoresis-Protein-Protein 230 Plus.
    Click on START to start the analysis, which is completed within 30 minutes.
    The raw data are shown by clicking on "Data Analysis" where all experiments, carried out at the day, are listed. Click on the experiment of interest and select it.
    The gel generated from the chosen experiment is automatically opened.
    Data can be shown as an electropherogram or gel-like image.
    Detailed information regarding the integration of the peaks in the electropherogram (to gain the purity data) is included in the manual of the software. The purity of a sample is automatically given by the system by automatic integration, but if needed, the manual integration can be applied.

Results:
  In non-reducing condition the results are indicated as % Purity, and % LMW (sum of peaks before monomer).
  In reducing condition the results are indicated as % Purity, as sum of heavy chain and light chain.
  The indicative molecular weight values are reported in the table below:

Indicative Molecular Weight of Adalimumab

| Condition | Results | KDa |
|---|---|---|
| Non Reducing | Monomer | 151 |
| Reducing | LC | 27 |
| | HC | 58 |

2. Unfolding Temperature—DSF

DSF (differential scanning fluorimetry) was performed as follows:

2 microliters of Sypro Orange (Orange protein gel stain, cod. S6650, Life Technologies) previously diluted 500-fold in water for injection were added to 20 microliters of drug product solution. Upon addition of Sypro Orange, the DP solutions (triplicate preparation) are filled in 96-well plates (MicroAmp Fast 96-W Reaction Plate 0.1 mL, cod. 4346907). The plates are then sealed with a protective, transparent cover (MicroAmp Optical Adhesive Film, cod. 4311971) and then subjected to centrifugation to remove air bubbles. The plates are then inserted in the 7500 Fast Real-Time AB Applied Biosystem PCR system and scanned for emission profiles at temperatures from room temperature to 90-100° C. The dependence of intensity of fluorescence emission on temperature is a curve which typically shows an inversion point/discontinuation at the denaturation temperature, parameter used to compared the different compositions.

3. Isoforms Profile—iCE280 cIEF by iCE280 (isoforms profile): After purification and removal of salts with centrifugation in Amicon Ultra-4 centrifugal devices (cut off 10 kDa), the samples were pre-diluted to the concentration of 5.0 mg/mL with purified water. A second dilution was then made to 1.0 mg/mL with a solution composed of: methyl cellulose, Pharmalyte 5-8 (GE Healthcare), Pharmalyte 8-10.5 (GE Healthcare), low pI marker 7.05 (Protein Simple), high pI marker 9.50 (Protein Simple) and purified water. Upon dilution the samples were centrifuged at 10000 rpm for 3 minutes. An additional centrifugation step (2 minutes at 7000 rpm) is then conducted on 150 microL of each sample transferred in glass inserts. The cIEF (capillary isoelectric focusing) was carried out with the iCE280 system by Protein Simple, using capillary cartridges Fc with 100 micron ID coating and total length of 50 nm (Cat. No. 101700/101701 by Protein Simple). The separation of the various isoforms is made using 100 mM sodium hydroxide (in 0.1% methyl cellulose) as a cathodic solution and 80 mM o-phosphoric acid (in 0.1% methyl cellulose) as an anodic solution. The electropherogram is acquired at 280 nm over pre-focusing and focusing times of 1 and 6 minutes respectively, at a voltage of 1500 V (pre-focusing) and 3000 V (focusing).

4. Protein Content—OD

OD (protein content) measurements were taken on samples which were initially diluted gravimetrically (triplicate independent dilutions were made) with relevant buffer or placebo from starting concentration to about 10 mg/mL. The diluted solutions were tested for absorbance at 280 and 320 nm in 0.1 cm pathlength quartz cuvettes, at room temperature, with a double-beam spectrophotometer (Lambda35 by Perkin Elmer). The value of 1.35 was used as molar extinction coefficient of Adalimumab.

5. Aggregates Determination—SE-HPLC

The samples were diluted with DPBS 1× to a concentration of 0.5 mL and injected (20 microL injection volume) in a Column TSK gel Super SW3000 4.6 mm ID X30.0 cm cod.18675 by Tosoh maintaining isocratic conditions (mobile phase: 50 mM Sodium Phosphate+0.4M Sodium perchlorate, pH 6.3±0.1). UV detection was made at 214 nm at a flow rate of 0.35 mL. The duration of each analytical run was 15 minutes. Prior to the analysis the samples were maintained at 2-8° C. in the autosampler of the Waters Alliance HPLC systems used for this test.

6. Turbidity—Nephelometry

Turbidity was assessed via nephelometric (effect based on the light diffusion effect caused by particles with dimensions typically <1 micron) measurements conducted with a turbidimeter 2100AN IS Turbidimeter by Hach at room temperature. Minimum amounts of 3 mL of solution were placed in reduced volume glass cuvettes and tested for diffusive effect after prior calibration of the instrument with a series of standard solutions (0.1-7500 NTU).

7. Osmolality Determination—Osmolality

Osmolality was measured based on the cryoscopic characteristic of the solutions. The tests were conducted with an Osmomat 030-D by Gonotech subjecting 50 microL of the sample to freezing. The freezing temperature depends on the osmolality of the solution (i.e. on the presence of agents dissolved such as salts, sugars, other ionic and non-ionic species, etc).

8. pH Determination—pH pH was determined using potentiometric measurements conducted at room temperature with Mettler Toledo Seven Multi pH meters.

9. Particle Count—Sub-Visible Particles

The samples were 5-fold diluted with purified water to a final volume of 25 mL. The number of particles are determined at room temperature by PAMAS SVSS by Aminstruments collecting four independent runs and averaging the results for each respective dimensional fraction of interest.

Example 1—Formulations for First Formulation Screen

The following first set of formulations (often referenced herein as DoE1 formulations) are shown below in Table 1.

TABLE 1

List of DoE1 formulations for later Screen Experiments 1

| Form # | Salt (NaCl) concentration (mM) | Buffer type (10 mM) | pH | Stabilizer |
|---|---|---|---|---|
| 1 | 25 | Acetate | 4.6 | Lysine Hydrochloride (100 mM) |
| 2 | 100 | Acetate | 4.6 | Arginine Monohydrocloride + Aspartic Acid (80 mM + 20 mM) |
| 3 | 50 | Acetate | 4.8 | Arginine Monohydrocloride + Aspartic Acid (80 mM + 20 mM) |
| 4 | 25 | Acetate | 4.8 | Mannitol (200 mM) |
| 5 | 75 | Acetate | 4.8 | Mannitol (200 mM) |
| 6 | 50 | Acetate | 5.0 | Lysine Hydrochloride (100 mM) |
| 7 | 100 | Acetate | 5.0 | Trehalose dihydrate (200 mM) |
| 8 | 25 | Acetate | 5.2 | Trehalose dihydrate (200 mM) |
| 9 | 75 | Acetate | 5.2 | Arginine Monohydrocloride + Aspartic Acid (80 mM + 20 mM) |
| 10 | 75 | Acetate | 5.2 | Trehalose dihydrate (200 mM) |

The formulations of Table 1 were manufactured starting from a preformulated, surfactant—free DS material.

An aliquot of the DS was diafiltrated with 10 mM sodium acetate/acetic acid buffer at pH 5.0 until a three-fold volume exchange with the buffer was achieved. Then the required excipients have been added to the buffer-exchanged DS materials and the pH adjusted to the target by addition of a diluted solution of sodium hydroxide. Each formulation was filtered through 0.22 μm PES filters.

In Table 2, the results in terms of material recovery and osmolality for the three buffer-exchanges DS materials are reported.

TABLE 2

Recovery and osmolality of the DS materials after buffer exchange

| | Starting | | | After exchange | | | |
|---|---|---|---|---|---|---|---|
| Buffer | DS volume (mL) | Starting DS Concentration (mg/mL) | Protein Treated (mg) | Final Volume (mL) | Final Concentration (mg/mL) | Protein Recovered (mg) | Recovery (%) | Osmolality (mOsm/kg) |
| Acetate | 200 | 63.3 | 12660 | 180 | 65.2 | 11736 | 93 | 30 |

There was good recovery for the sodium acetate buffer (>90%). The osmolality values indicate the satisfactory degree of buffer exchange reached, with a minimal residual of species coming from the originating DS.

Example 2—Formulations for Second Formulation Screen

The following second set of formulations (often referenced herein as DoE2 formulations) are shown below in Table 3 (as derived from Table 4 below that).

TABLE 1

List of DoE2 formulations for later Screen Experiments 2 (formulations derived from that presented in Table 4 with the extra surfactant indicated)

| | Polysorbate 80 concentration (mg/mL) | | |
|---|---|---|---|
| Formulations | 0 | 0.5 | 1 |
| Form 1 (deriving from Form A, Table 4) | x | — | — |
| Form 2 (deriving from Form A, Table 4) | — | x | — |
| Form 3 (deriving from Form A, Table 4) | — | — | X |

TABLE 4

Formulation prototype deriving from the DoE1 screen

| Form | Salt (NaCl) mM | Buffer type (10 mM) | pH | Stabilizer |
|---|---|---|---|---|
| A | 75 | Acetate | 5.2 | Trehalose dihydrate (200 mM) |

The DoE2 formulations (Table 3) were manufactured starting from a preformulated, surfactant—free, DS material.

As before, aliquots of the DS have been diafiltrated until a three-fold volume exchange was achieved. Then the required excipients have been added to the buffer-exchanged DS materials and the pH adjusted to the target by addition of a diluted solution of sodium hydroxide. Each formulation was filtered through 0.22 μm PES filters.

In Table 5, the results in terms of osmolality and turbidity for the buffer-exchanges DS materials are reported.

The osmolality values 40 mOsm/kg) indicated the satisfactory degree of buffer exchange reached, with a minimal residual of species coming from the originating DS.

TABLE 5

Osmolality and turbidity of the DS materials after buffer exchange

| Buffer | Turbidity (NTU) | Osmolality (mOsm/kg) |
|---|---|---|
| Acetate | 19 | 29 |

Example 3—Comparative Formulations for Both First and Second Screens

For comparison and control purposes, three reference formulations were prepared or obtained, including Ref-1 (Humira® composition manufactured by the Applicant); Ref-2 (RMP US—Humira® commercial drug product from the USA); and Ref-3 (RMP EU—Humira® commercial drug product from the EU). All of these reference formulations had the composition shown in Table 6.

TABLE 6

Composition of Humira DP

| Ingredient | Amount per container (mg) (filling volume = 0.8 mL) | Amount (mg/mL) |
|---|---|---|
| Adalimumab | 40 | 50 |
| Citric Acid Monohydrate | 1.04 | 1.3 |
| Dibasic sodium phosphate dihydrate | 1.22 | 1.53 |
| Mannitol | 9.6 | 12 |
| Monobasic sodium phosphate dihydrate | 0.69 | 0.86 |
| Polysorbate 80 | 0.8 | 1 |
| Sodium chloride | 4.93 | 6.16 |
| Sodium citrate | 0.24 | 0.3 |
| WFI and sodium hydroxide | q.b. to adjust pH to 5.2 | q.b. to adjust pH to 5.2 |

Screening

A first formulation screen (DoE1) led to the identification of various factors (e.g. pH, presence of NaCl, excipient type) responsible for protein stability, and ultimately to the selection of formulations to be pursued in a second screen (DoE2), which sought to fine-tune the formulations and evaluate how surfactants, such as Polysorbate 80, can impact the stability of the protein.

Each of the two screens involved various analytical testing, as defined hereinbefore and referred to hereinafter, upon a range of different formulations which were exposed to varying levels of thermal, mechanical, and light stress over prolonged periods (e.g. 1 month). These formulation screens enabled the gathering of a significant amount of data, which provided surprising and valuable insights allowing for the development of new advantageous formulations.

The results of the two formulations screens are presented below.

Screening Experiment 1—Analysis and Screening of Example 1 Formulations Against Comparative Formulations of Example 3

Preliminary DoE screening (Step 1) evaluated the effect that ionic strength (given by NaCl), pH and different stabilizers exerts on the protein in the course of short term stability studies.

A response surface D-Optimal statistical design has been applied. Three factors were considered:
  Ionic strength (driven by NaCl concentration, which was varied in the range 25 mM-100 mM and was set as a numeric factor);
  pH (the range 4.6-6.4 buffered by acetate, was investigated;
  Stabilizer/Excipient (categoric factor comprising several levels: Lysine Hydrochloride, Arginine+Aspartic Acid, Mannitol, Trehalose Dihydrate).

These formulations were manufactured, as described in Example 1 above, starting from DS without Polysorbate 80 and were therefore surfactant—free.

Table 7 below summarizes the formulations tested within this screening. In addition to the 10 formulations proposed, two controls have also been analysed as comparators:
  Humira commercial drug product "DP" (Formulated as per Example 3 above)
  MS drug substance "DS" formulated as Humira commercial DP (Formulated as per Example 3 above)

The formulations were tested according to the plan reported in Table 8. Thermal stress up to 1 month at 40° C. was considered. High throughput assessment made with the DSF technique (aimed at a fast screening based on determination of protein unfolding temperature) was performed at T0.

TABLE 8

Panel of analytical tests carried out on preliminary DoE formulations (Step 1): 1-month thermal stress conditions at 40° C.

| Accelerated (40° C.) | | Stability time (weeks) | | |
| --- | --- | --- | --- | --- |
| Methods | Test | 0 | 2 w | 4 w |
| OD | Content | x | — | x |
| SE-HPLC | Aggregates | x | x | x |
| Bionalyzer | Purity | x | x | x |
| pH | pH | x | x | x |
| Osmolality | Osmolality | x | — | — |
| DSF | Unfolding T | x | — | — |

1.1 Osmolality Screen

The osmolality of the DoE1 formulations compounded starting from the buffer exchanges DS materials (par. 5.1.1) is reported in Table 9.

Most formulations were found in the range of osmolality of 250-400 mOsm/kg, while slightly higher values were observed at the highest sodium chloride concentrations.

TABLE 7

List of DoE1 formulations (Step 1) screened through thermal stress conditions (stability at 40° C.) and high throughput determination of protein unfolding temperature (DSF).

| Form # | Salt (NaCl) conc (mM) | Buffer type (10 mM) | pH | Stabilizer |
| --- | --- | --- | --- | --- |
| 1 | 25 | Acetate | 4.6 | Lysine Hydrochloride (100 mM) |
| 2 | 100 | Acetate | 4.6 | Arginine Monohydrocloride + Aspartic Acid (80 mM + 20 mM) |
| 3 | 50 | Acetate | 4.8 | Arginine Monohydrocloride + Aspartic Acid (80 mM + 20 mM) |
| 4 | 25 | Acetate | 4.8 | Mannitol (200 mM) |
| 5 | 75 | Acetate | 4.8 | Mannitol (200 mM) |
| 6 | 50 | Acetate | 5.0 | Lysine Hydrochloride (100 mM) |
| 7 | 100 | Acetate | 5.0 | Trehalose dihydrate (200 mM) |
| 8 | 25 | Acetate | 5.2 | Trehalose dihydrate (200 mM) |
| 9 | 75 | Acetate | 5.2 | Arginine Monohydrocloride + Aspartic Acid (80 mM + 20 mM) |
| 10 | 75 | Acetate | 5.2 | Trehalose dihydrate (200 mM) |
| Ref-1 (MS) | Humira composition (formulation manufactured with MS Drug Substance) - Example 3 | | | |
| Ref-2 (RMP US) | Humira commercial DP (USA) - Example 3 | | | |
| Ref-3 (RMP EU) | Humira commercial DP (EU) - Example 3 | | | |

TABLE 9

Osmolality (mOsm/kg) recorded at time 0 for DoE1 screening formulations

| Form # | Salt (NaCl) concentration (mM) | Buffer type (10 mM) | pH | Stabilizer | Time 0 |
|---|---|---|---|---|---|
| 1 | 25 | Acetate | 4.6 | Lysine Hydrochloride (100 mM) | 0.302 |
| 2 | 100 | Acetate | 4.6 | Arginine Monohydrocloride + Aspartic Acid (80 mM + 20 mM) | 0.407 |
| 3 | 50 | Acetate | 4.8 | Arginine Monohydrocloride + Aspartic Acid (80 mM + 20 mM) | 0.339 |
| 4 | 25 | Acetate | 4.8 | Mannitol (200 mM) | 0.322 |
| 5 | 75 | Acetate | 4.8 | Mannitol (200 mM) | 0.423 |
| 6 | 50 | Acetate | 5.0 | Lysine Hydrochloride (100 mM) | 0.342 |
| 7 | 100 | Acetate | 5.0 | Trehalose dihydrate (200 mM) | 0.506 |
| 8 | 25 | Acetate | 5.2 | Trehalose dihydrate (200 mM) | 0.341 |
| 9 | 75 | Acetate | 5.2 | Arginine Monohydrocloride + Aspartic Acid (80 mM + 20 mM) | 0.366 |
| 10 | 75 | Acetate | 5.2 | Trehalose dihydrate (200 mM) | 0.441 |
| Reference In-House (Humira composition, Merck Serono DS) | | | | | 0.374 |
| RMP (USA) Humira | | | | | NA |
| RMP (EU) Humira | | | | | 0.310 |

1.2 Protein Content (OD)

The protein content of the DoE1 formulations was determined at time 0 and after 1 month at 40° C.

FIG. 1 is a bar chart showing the protein content (mg/mL) of the DoE1 formulations (of Example 1), along with reference standards (representing comparator HUMIRA® formulations), at an arbitrary start point (blue bars, time=0) and after 4 weeks (red bars) of the formulation(s) being heated at 40° C.

The results presented in FIG. 1, indicated no significant changes occurring over time. All concentrations were found in line with the target of 50 mg/mL.

1.3 Aggregation (SE-HPLC)

Figure 2:
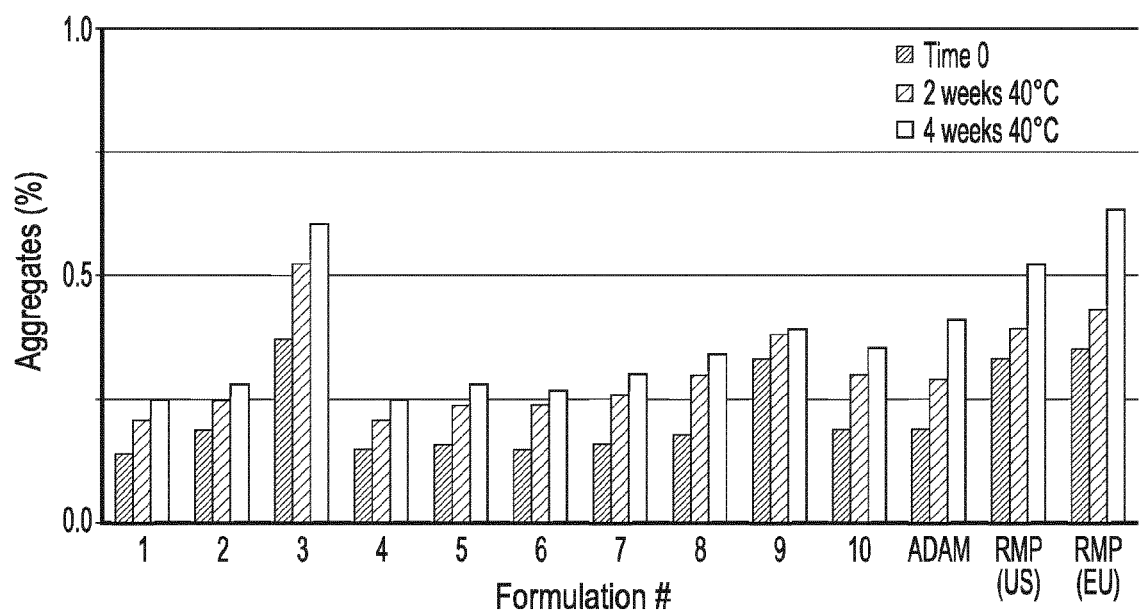
FIG. 2 is a bar chart showing the % aggregation, as determined by SE-HPLC, of the DoE1 formulations (of Example 1), along with reference standards (representing comparator HUMIRA® formulations), at an arbitrary start point (blue bars, time=0) and after both 2 weeks (green bars) and 4 weeks (orange bars) of the formulation(s) being heated at 40° C.

FIG. 2 is a bar chart showing the % aggregation, as determined by SE-HPLC, of the DoE1 formulations (of Example 1), along with reference standards (representing comparator HUMIRA® formulations), at an arbitrary start point (blue bars, time=0) and after both 2 weeks (green bars) and 4 weeks (orange bars) of the formulation(s) being heated at 40° C. The total aggregates observed by SE-HPLC over stability at 40° C. are graphically represented in FIG. 2. Minimal increases in aggregation were observed in all formulation. However, even after 1 month, all aggregation levels amounted to less than 1%.

1.4 Fragmentation (Bioanalyzer)

Figure 3:
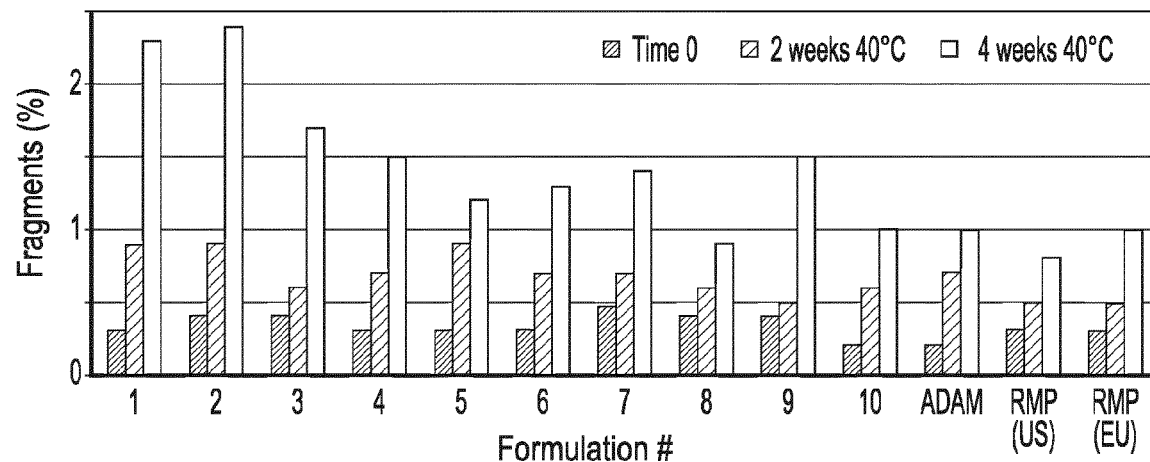
FIG. 3 is a bar chart showing the % fragmentation, as determined by a Bioanalyzer, of the DoE1 formulations (of Example 1), along with reference standards (representing comparator HUMIRA® formulations), at an arbitrary start point (dark blue bars, time=0) and after both 2 weeks (pink bars) and 4 weeks (light blue bars) of the formulation(s) being heated at 40° C.

FIG. 3 is a bar chart showing the % fragmentation, as determined by a Bioanalyzer, of the DoE1 formulations (of Example 1), along with reference standards (representing comparator HUMIRA® formulations), at an arbitrary start point (dark blue bars, time=0) and after both 2 weeks (pink bars) and 4 weeks (light blue bars) of the formulation(s) being heated at 40° C.

In FIG. 3, the variation of fragments over time as determined by Bioanalyzer is reported. Formulations at more acidic pH (typically lower than or equal to 5.0, as in Formulations 1-7) tend to undergo faster fragmentation rates. Moreover, the presence of amino acids at this pH range can considerably worsen the stability profile (Formulations 1-2-3). The detrimental effect of aminoacidic species is also confirmed at pH 5.2-5.4 (Formulation 9).

At pH>5.0 and in presence of sugar/polyols, all the formulas, including the references, are comparable (fragmentation lower than 1% after 1 month at 40° C.).

The data were analysed by means of ANOVA which confirmed the statistical significance of the pH factor (p-value<0.001), also indicating that pH values>5.0 should be targeted to minimize fragmentation.

Sodium chloride was not found to be a factor critical to stability in the range 25-100 mM.

1.5 pH Screening

Table 10 shows the pH of the DoE1 formulations (of Example 1), along with reference standards (representing comparator HUMIRA® formulations), at an arbitrary start point (time=0) and after both 2 weeks and 4 weeks of the formulation(s) being heated at 40° C.

As can be seen from Table 10, no deviations from targeted pH were observed.

TABLE 10 pH of DoE1 screening formulations determined over stability at 40° C.

| | | | | | | Stability time | |
|---|---|---|---|---|---|---|---|
| Form # | Salt (NaCl) conc (mM) | Buffer type (10 mM) | pH | Stabilizer | Time 0 | 2 weeks 40° C. | 4 weeks 40° C. |
| 1 | 25 | Acetate | 4.6 | Lysine Hydrochloride (100 mM) | 4.6 | 4.7 | 4.7 |
| 2 | 100 | Acetate | 4.6 | Arginine Monohydrocloride + Aspartic Acid (80 mM + 20 mM) | 4.7 | 4.6 | 4.7 |
| 3 | 50 | Acetate | 4.8 | Arginine Monohydrocloride + Aspartic Acid (80 mM + 20 mM) | 4.8 | 4.8 | 4.8 |
| 4 | 25 | Acetate | 4.8 | Mannitol (200 mM) | 4.8 | 4.8 | 4.8 |
| 5 | 75 | Acetate | 4.8 | Mannitol (200 mM) | 4.8 | 4.8 | 4.8 |
| 6 | 50 | Acetate | 5.0 | Lysine Hydrochloride (100 mM) | 5.0 | 5.0 | 5.0 |
| 7 | 100 | Acetate | 5.0 | Trehalose dihydrate (200 mM) | 5.0 | 5.0 | 5.0 |
| 8 | 25 | Acetate | 5.2 | Trehalose dihydrate (200 mM) | 5.2 | 5.2 | 5.2 |
| 9 | 75 | Acetate | 5.2 | Arginine Monohydrocloride + Aspartic Acid (80 mM + 20 mM) | 5.1 | 5.2 | 5.2 |
| 10 | 75 | Acetate | 5.2 | Trehalose dihydrate (200 mM) | 5.2 | 5.2 | 5.2 |
| Reference In-House (Humira composition, Merck Serono DS) | | | | | 5.2 | 5.2 | 5.2 |
| RMP (USA) Humira | | | | | 5.3 | 5.3 | 5.3 |
| RMP (EU) Humira | | | | | 5.3 | 5.3 | 5.3 |

1.6 Unfolding Temperature (DSF)

DSF is a high throughput method which aims at the determination of the unfolding temperature of proteins by virtue of increasing interactions with fluorescent probes as temperature ramps are applied to the samples. When the protein starts to unfold, it will progressively expose hydrophobic patches to the solvent attracting the fluorescent probes that will pass from the free state in solution (non-fluorescent) to the bound state (via hydrophobic interactions) with the protein, thus increasing the degree of fluorescent signal.

From the evaluation of the fluorescence signal, it was possible to determine the midpoint of the sigmoidal curves, which indicates the transition point of each formulation. It is assumed that the higher the transition point, the higher the resistance of the formula to thermal stress.

Figure 4:
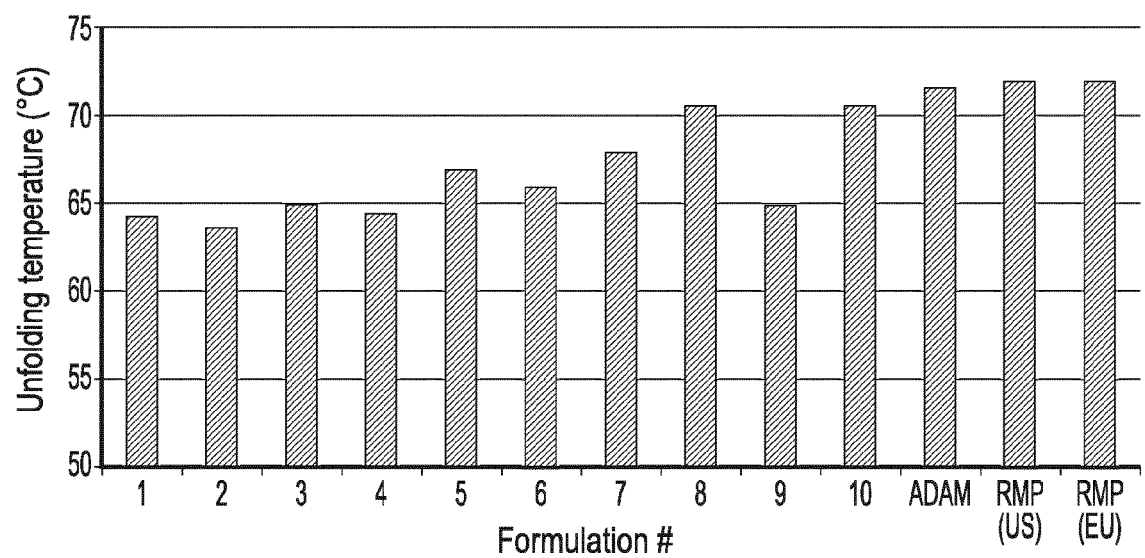
FIG. 4 is a bar chart showing the unfolding temperature (° C.), as determined by DSF, of the DoE1 formulations (of Example 1), along with reference standards (representing comparator HUMIRA® formulations).

The results of the assessment conducted on the DoE1 screening formulations are reported in FIG. 4. FIG. 4 is a bar chart showing the unfolding temperature (° C.), as determined by DSF, of the DoE1 formulations (of Example 1), along with reference standards (representing comparator HUMIRA® formulations).

The unfolding temperature of the three reference formulations is 71-72° C. Few formulations, aside from the references, were found to have unfolding temperatures higher than 70° C., but those that did include:

Formulations 8 and 10 (formulations in sodium acetate buffer pH 5.2+Trehalose dihydrate at varying sodium chloride concentrations)

Therefore, this test confirmed the results previously obtained for fragmentation by Bioanalyzer: polyols/sugars can positively impact the thermal stability of the protein, especially at pH>5.0, while sodium chloride does not seem to significantly affect its behavior.

The ANOVA model for response surface identified pH (p-value<0.01) and excipient (0.01<p-value<0.05) as the significant factors affecting protein stability.

1.7 Iso Forms Profile Change Vs RMP

The isoforms profile of DoE screening formula 10 has been tested after 10-11 weeks at 40° C. and compared to Reference samples.

The data, in terms of main peak and acidic cluster variations, are reported in Table 11.

Comparable variations are obtained for the five samples tested.

TABLE 11

Isoforms profile by iCE280 of most promising formulations from DoE screening 1 and references.

| ID | Time 0 | 10 weeks (40° C.) | 11 weeks (40° C.) |
|---|---|---|---|
| Main | | | |
| DoE1-10 | 56.7 | 40.1 | — |
| Ref-1 (MS) | 55.8 | 38.5 | — |
| Ref-3 RMP (EU) | 56.5 | 40.7 | — |
| Ref-2 RMP (US) | 56.8 | 40.6 | — |
| Acidic cluster | | | |
| DoE1-10 | 19.3 | 39.3 | — |
| Ref-1 (MS) | 19.8 | 40.5 | — |
| Ref-3 RMP (EU) | 19.5 | 38.9 | — |
| Ref-2 RMP (US) | 20.2 | 39.8 | — |

Conclusion of Screening Experiment 1

The results obtained from Bioanalyzer and DSF testing were combinately evaluated by means of the ANOVA model for response surfaces in order to determine the best compositions that can possibly guarantee the highest thermal stability to the protein.

The list of the compositions recommended are reported in Table 12, which also compares the performances of the resulting prototypes formulations with the Humira RMP, in terms of unfolding temperature and fragmentation change over 1 month at 40° C.

Formulation A corresponds to DoE1 Formulation 10 and the real data were reported.

Comparing these formulas to the RMP it can be concluded that the behavior of these prototype formulations in response to thermal stress is comparable with that observed for the RMP.

TABLE 12

Outcome of DoE1 experiments: recommended compositions for second screen

| Form | Salt (NaCl) mM | Buffer type (10 mM) | pH | Stabilizer |
|---|---|---|---|---|
| A | 75 | Acetate | 5.2 | Trehalose dihydrate (200 mM) |

Somewhat unexpectedly, formulations containing trehalose dihydrate as the sole stabilizer performed extremely well, especially in terms of fragmentation inhibition, unfolding inhibition, and pH maintenance. Such trehalose-based formulations also exhibited good performance in terms of aggregation and precipitation. That trehalose was such a strong candidate as a stabiliser, especially on its own, was extremely promising in view of its antioxidant properties, which would impart further long-term chemical stability (especially vis a vis oxidation and/or photo-oxidation) to adalimumab formulations. Furthermore, that trehalose can be used alone and yet still exhibit excellent performance, was considered especially encouraging and paved the way to less complex formulations employing fewer components—this would in turn reduce processing and costs associated with the production of the relevant adalimumab drug product. As such, these trehalose-based formulations were taken into a second round of screening experiments in order to fine-tune the formulations.

Screening Experiment 2—Analysis and Screening of Example 2 Formulations Against Comparative Formulations of Example 3

A formulation prototype from the previous screen was identified (Table 12). Since the previous step was conducted with no surfactant added, the second step aimed to screen a series of levels of compounded Polysorbate 80 surfactant (range: 0-1 mg/mL) in order to assess whether surfactant addition is required to favor protein stability.

Table 3 (Example 2) summarizes the design of this second step of the study and lists the formulations (DoE2 formulations) tested in this second screening exercise.

Typically, surfactants have been observed to contrast mechanical stress-induced aggregation and shaking stress tests have been therefore executed so as to evaluate how Polysorbate 80 affects protein stability and response to shaking.

As with Step 1, the reference compositions described in Example 3 have also been evaluated so as to provide a baseline for the development of a new formulation.

The complete list of analyses conducted on this block of formulations is reported in Table 13. In this second screen, the respective formulations were exposed to three different types of stress, thermal, mechanical, and light.

TABLE 13

Panel of analytical tests carried out on DoE2 formulations (Step 2): 1-month thermal stress conditions at 40° C. (A), shaking stress at 200 rpm (B) and light exposure according to ICH Q1B (C).

A. Thermal stress a 40° C.

| Accelerated (40° C.) | | Stability time (weeks) | | |
|---|---|---|---|---|
| Methods | Test | 0 | 2 w | 4 w |
| OD | Content | x | — | x |
| iCE280 | Isoforms | x | x | x |
| SE-HPLC | Aggregates | x | x | x |
| Bionalyzer | Purity | x | x | x |
| pH | pH | x | x | x |
| Osmolality | Osmolality | x | — | — |
| Nephelometry | Turbidity | x | x | x |
| DSF | Unfolding T | x | — | — |

B. Shaking stress conditions

| Shaking stress (200 rpm) | | Stability time (hours) | | |
|---|---|---|---|---|
| Methods | Test | 0 | 24 h | 48 h |
| OD | Content | x | — | — |
| SE-HPLC | Aggregates | x | x | x |
| Bioanalyzer | Purity | x | x | x |
| pH | pH | x | x | x |
| Nephelometry | Turbidity | x | x | x |

C. Light Exposure 7 hours of exposure at 765 W/m² (ICH Q1B).

| Light exposure | | Sample | |
|---|---|---|---|
| Methods | Test | Time 0 | Exposed |
| OD | Content | x | — |
| 10E280 | Isoforms | x | x |
| SE-HPLC | Aggregates | x | x |
| Bioanalyzer | Purity | x | x |
| pH | pH | x | x |
| Nephelometry | Turbidity | x | x |

Thermal stress tests were performed by simply heating a sample of the relevant formulations at the stipulated temperature for the stipulated amount of time (typically 2 weeks or 4 weeks/1 month).

Mechanical stress tests were performed by simply mechanically shaking a sample of the relevant formulations at room temperature at 200 rpm for the stipulated period of time (typically 24 hours or 48 hours).

Light stress tests were performed by simply exposing a sample of the relevant formulations to 765 W/m² light (in accordance with ICH Q1B guidelines of the European Medicines Agency in relation to photostability testing of new active substances and medicinal products) for 7 hours.

2.1 Osmolality

The osmolality of the DoE2 screening formulations are reported in Table 14. The values, comprised in the range 378-401 mOsm/kg are probably overestimated due to the presence of Trehalose dihydrate that can lead to some increase in viscosity affecting the cryoscopic point of the solutions and hence the osmolality. This was confirmed by measurements in relation to other test formulations, which were 3-fold diluted with WFI prior to the osmolality test in order to decrease the viscosity: the real osmolality of all these formulas is <350 mOsm/kg.

TABLE 14

Osmolality of DoE2 screening formulations (tested undiluted)

| Form # | Salt (NaCl) concentration (mM) | Buffer type (10 mM) | pH | Stabilizer | Surfactant (Polysorbate 80) concentration (mg/mL) | Time 0 |
|---|---|---|---|---|---|---|
| DoE2-1 | 50 | Acetate | 5.2 | Trehalose dihydrate (200 mM) | 0 | 390 |
| DoE2-2 | 50 | Acetate | 5.2 | Trehalose dihydrate (200 mM) | 0.5 | 386 |
| DoE2-3 | 50 | Acetate | 5.2 | Trehalose dihydrate (200 mM) | 1 | 388 |

2.2 Protein Content (OD)

The protein content of all the DoE2 formulations at time 0 were in line with the protein concentration target of 50 mg/mL (Table 15).

TABLE 15

Protein content (OD) of DoE2 screening formulations (tested undiluted)

| Form # | Salt (NaCl) concentration (mM) | Buffer type (10 mM) | pH | Stabilizer | Surfactant (Polysorbate 80) concentration (mg/mL) | Time 0 |
|---|---|---|---|---|---|---|
| DoE2-1 | 50 | Acetate | 5.2 | Trehalose dihydrate (200 mM) | 0 | 50.6 |
| DoE2-2 | 50 | Acetate | 5.2 | Trehalose dihydrate (200 mM) | 0.5 | 52.0 |
| DoE2-3 | 50 | Acetate | 5.2 | Trehalose dihydrate (200 mM) | 1 | 51.3 |

2.3 Aggregates with Thermal Stress (SE-HPLC)

Figure 5:
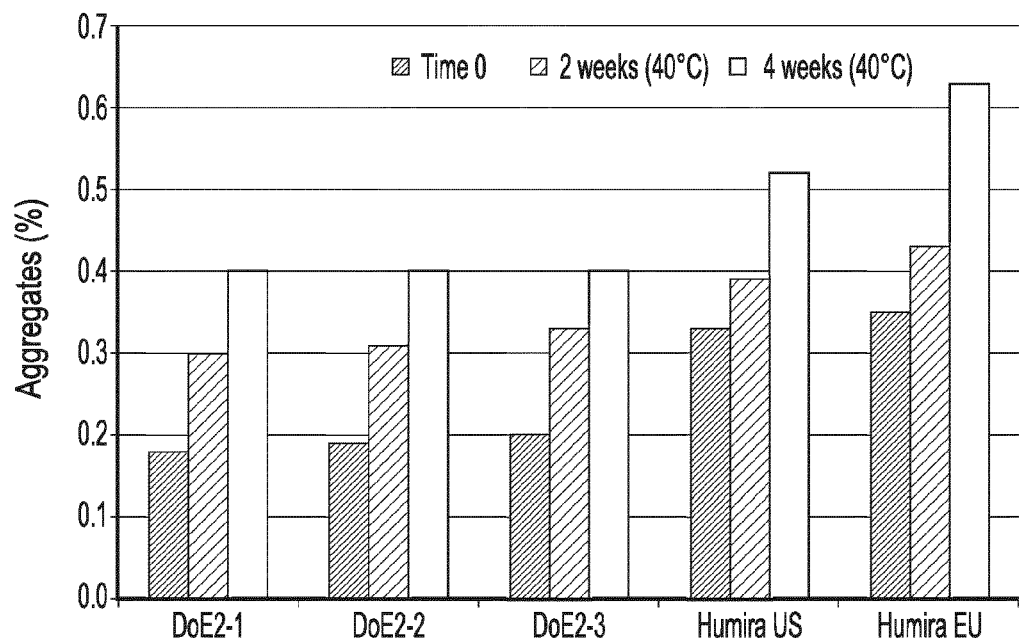
FIG. 5 is a bar chart showing the % aggregation, as determined by SE-HPLC, of the DoE2 formulations (of Example 2), along with reference standards (representing comparator HUMIRA® formulations), at an arbitrary start point (red bars, time=0) and after both 2 weeks (green bars) and 4 weeks (purple bars) of the formulation(s) being heated at 40° C.

The variations in total aggregates by SE-HPLC are presented in FIG. 5. FIG. 5 is a bar chart showing the % aggregation, as determined by SE-HPLC, of the DoE2 formulations (of Example 2), along with reference standards (representing comparator HUMIRA® formulations), at an arbitrary start point (red bars, time=0) and after both 2 weeks (green bars) and 4 weeks (purple bars) of the formulation(s) being heated at 40° C.

Minimal changes were observed for all the formulation, being the total aggregates amount after 1 month at 40° C. below 1%.

The performances of the DoE2 screening formulations are comparable/slightly better than those of the RMP materials.

2.4 Fragmentation with Thermal Stress (Bioanalyzer)

Figure 6:
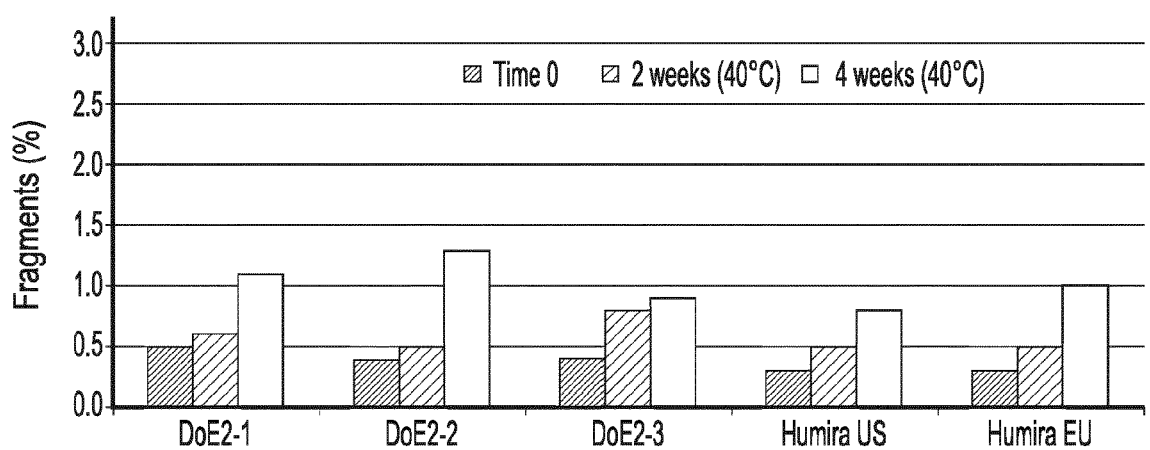
FIG. 6 is a bar chart showing the % fragmentation, as determined by a Bioanalyzer, of the DoE2 formulations (of Example 2), along with reference standards (representing comparator HUMIRA® formulations), at an arbitrary start point (blue bars, time=0) and after both 2 weeks (red bars) and 4 weeks (green bars) of the formulation(s) being heated at 40° C.

The variations in fragments by Bioanalyzer are presented in FIG. 6. FIG. 6 is a bar chart showing the % fragmentation, as determined by a Bioanalyzer, of the DoE2 formulations (of Example 2), along with reference standards (representing comparator HUMIRA® formulations), at an arbitrary start point (blue bars, time=0) and after both 2 weeks (red bars) and 4 weeks (green bars) of the formulation(s) being heated at 40° C.

In sodium acetate the presence of Polysorbate 80 at 1 mg/mL seems to slightly improve stability (cfr. DoE2-3 vs. DoE2-1 and DoE2-2) providing performances comparable to those observed in the RMP.

2.5 Isoforms Profile with Thermal Stress (iCE280)

Figure 7:
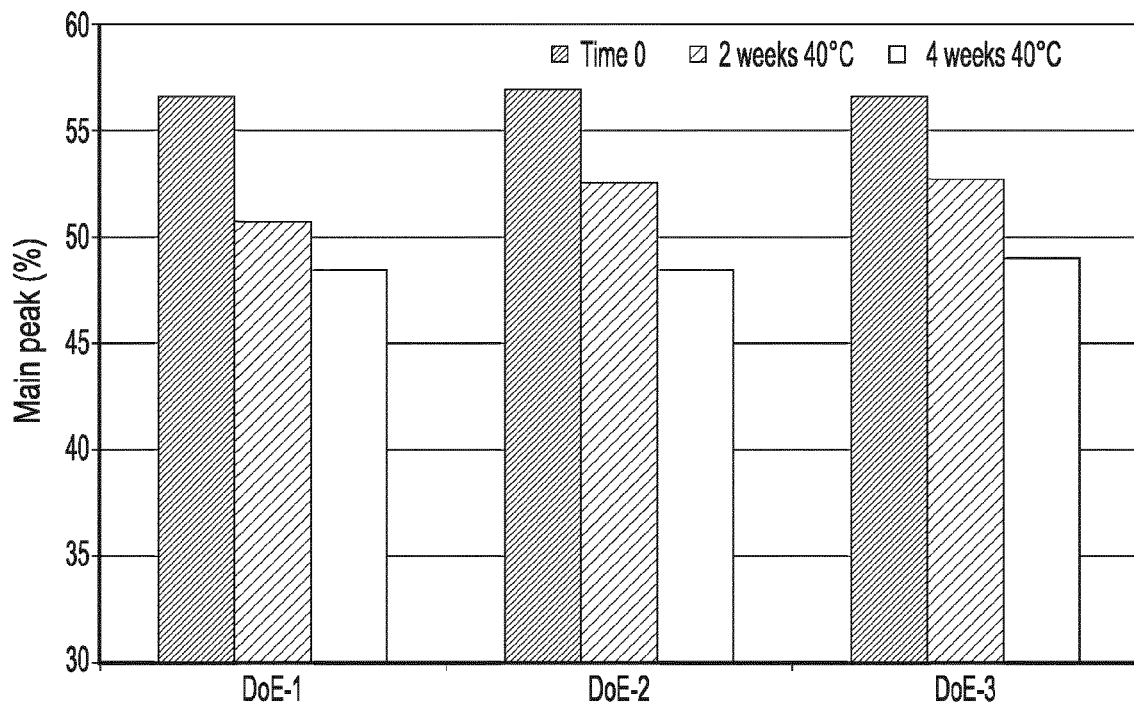
FIG. 7 is a bar chart showing the main peak isoforms profile, as determined by iCE280 analysis, of the DoE2 formulations (of Example 2) at an arbitrary start point (blue bars, time=0) and after both 2 weeks (red bars) and 4 weeks (green bars) of the formulation(s) being heated at 40° C.
Figure 8:
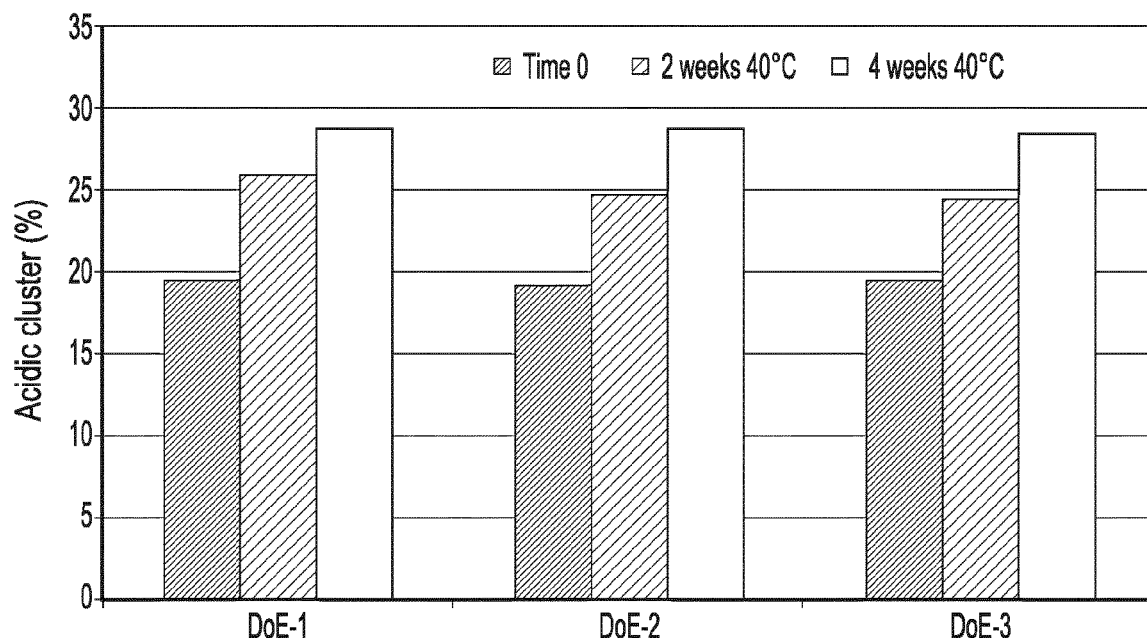
FIG. 8 is a bar chart showing the acid cluster peak(s) isoforms profile, as determined by iCE280 analysis, of the DoE2 formulations (of Example 2) at an arbitrary start point (blue bars, time=0) and after both 2 weeks (red bars) and 4 weeks (green bars) of the formulation(s) being heated at 40° C.

The main peak and acidic cluster changes of the three formulations over 1 month at 40° C. are reported in FIGS. 7 and 8 respectively FIG. 7 is a bar chart showing the main peak isoforms profile, as determined by iCE280 analysis, of the DoE2 formulations (of Example 2) at an arbitrary start point (blue bars, time=0) and after both 2 weeks (red bars) and 4 weeks (green bars) of the formulation(s) being heated at 40° C.

FIG. 8 is a bar chart showing the acid cluster peak(s) isoforms profile, as determined by iCE280 analysis, of the DoE2 formulations (of Example 2) at an arbitrary start point (blue bars, time=0) and after both 2 weeks (red bars) and 4 weeks (green bars) of the formulation(s) being heated at 40° C.

These results confirm the experimental evidences already highlighted by iCE280 on the prototype formulations (resulting from the first screening).

The results, in terms of acidic cluster, are in line with the observations made for the main peak.

2.6 pH Screen with Thermal Stress

The variation in pH of the DoE2 formulations (of Example 2) over a period of time during which the formulations are heated at 40° C. is shown in Table 16.

pH was entirely stable over the testing period.

2.7 Turbidity with Thermal Stress (Nephelometry)

Figure 9:
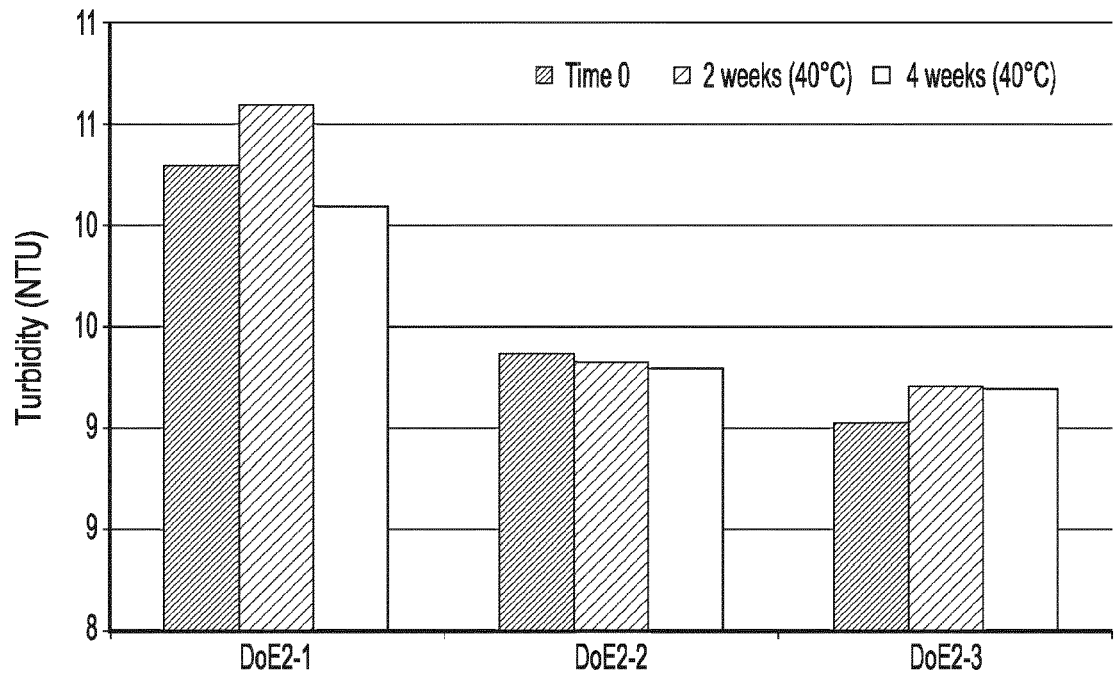
FIG. 9 is a bar chart showing the turbidity, as determined by Nephelometry, of the DoE2 formulations (of Example 2) at an arbitrary start point (blue bars, time=0) and after both 2 weeks (red bars) and 4 weeks (green bars) of the formulation(s) being heated at 40° C.

FIG. 9 is a bar chart showing the turbidity, as determined by Nephelometry, of the DoE2 formulations (of Example 2) at an arbitrary start point (blue bars, time=0) and after both 2 weeks (red bars) and 4 weeks (green bars) of the formulation(s) being heated at 40° C.

The turbidity of the three formulations is, time 0, in the range of typically opalescent solutions (6-18 NTU). With respect to the originating DS materials, of typical turbidity of 19-52 NTU, the DP solutions after aseptic filtration are considerably clarified.

Importantly, turbidity values of Humira RMP are normally around 10 NTU, in line with our formulas.

2.8 Aggregates with Mechanical Stress (SE-HPLC)

Figure 10:
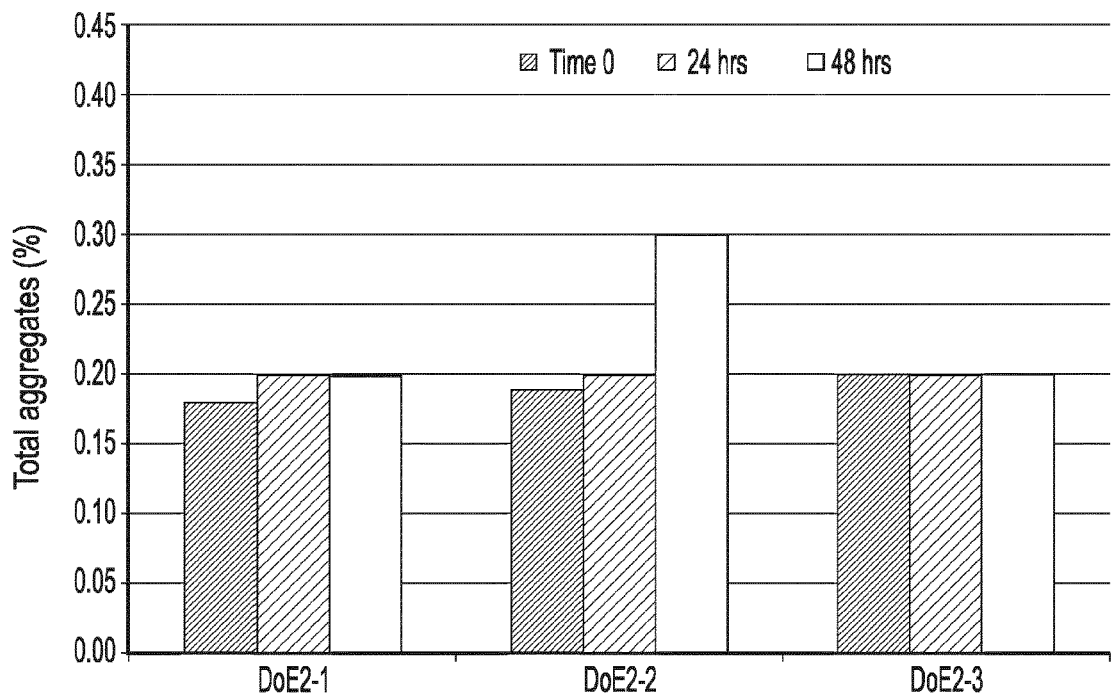
FIG. 10 is a bar chart showing the % aggregation, as determined by SE-HPLC, of the DoE2 formulations (of Example 2) at an arbitrary start point (blue bars, time=0) and after both 24 hours (red bars) and 48 hours (green bars) of the formulation(s) being mechanically agitated (shaking).

FIG. 10 is a bar chart showing the % aggregation, as determined by SE-HPLC, of the DoE2 formulations (of Example 2) at an arbitrary start point (blue bars, time=0) and after both 24 hours (red bars) and 48 hours (green bars) of the formulation(s) being mechanically agitated (shaking).

The variations in total aggregates by SE-HPLC are presented in FIG. 10.

Remarkably, no change (DoE2-1 and DoE2-3) or a maximum change of +0.1% (DoE2-2) are observed.

2.9 Fragmentation with Mechanical Stress (Bioanalyzer)

Figure 11:
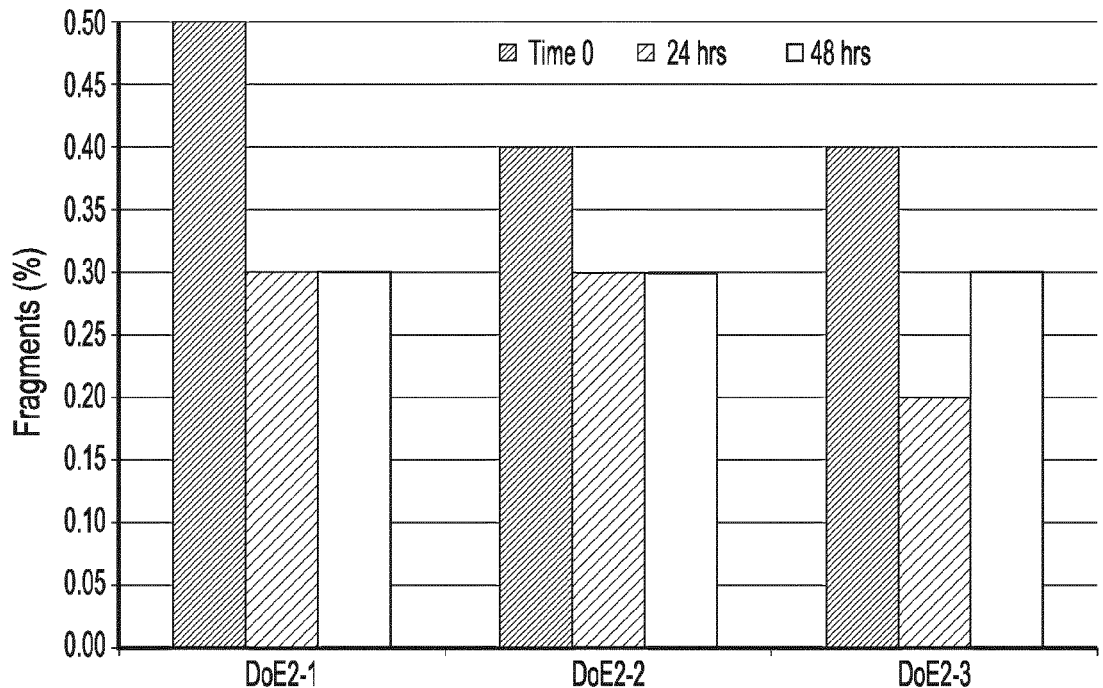
FIG. 11 is a bar chart showing the % fragmentation, as determined by a Bioanalyzer, of the DoE2 formulations (of Example 2) at an arbitrary start point (blue bars, time=0) and after both 24 hours (red bars) and 48 hours (green bars) of the formulation(s) being mechanically agitated (shaking).

FIG. 11 is a bar chart showing the % fragmentation, as determined by a Bioanalyzer, of the DoE2 formulations (of Example 2) at an arbitrary start point (blue bars, time=0) and after both 24 hours (red bars) and 48 hours (green bars) of the formulation(s) being mechanically agitated (shaking).

The variations in fragments by Bioanalyzer are presented in FIG. 11. Minimal changes are observed, being all the values recorded equal to or lower than 0.5%.

After 48 hour shaking at room temperature all the samples presented fragmentation in the range 0.2-0.4%. No trend towards fragmentation increases was highlighted upon mechanical shaking.

2.10 pH Screening with Mechanical Stress

The variation in pH of the DoE2 formulations (of Example 2) over a period of time during which the formulations are mechanically agitated (shaking) is shown in Table 17. No changes where observed.

TABLE 16

| | | | | | | | | |
|---|---|---|---|---|---|---|---|---|
| DoE2 screening: pH (thermal stress at 40° C.) | | | | | | | | |
| Form # | Salt (NaCl) concentration (mM) | Buffer type (10 mM) | | pH | Stabilizer | Surfactant (Polysorbate 80) concentration (mg/mL) | Time 0 | 2 weeks (40° C.) | 4 weeks (40° C.) |
| DoE2-1 | 50 | Acetate | 5.2 | Trehalose dihydrate (200 mM) | 0 | 5.2 | 5.2 | 5.2 |
| DoE2-2 | 50 | Acetate | 5.2 | Trehalose dihydrate (200 mM) | 0.5 | 5.2 | 5.3 | 5.3 |
| DoE2-3 | 50 | Acetate | 5.2 | Trehalose dihydrate (200 mM) | 1 | 5.2 | 5.3 | 5.3 |

TABLE 17

| Form # | Salt (NaCl) concentration (mM) | Buffer type (10 mM) | pH | Stabilizer | Surfactant (Polysorbate 80) concentration (mg/mL) | Time 0 | 24 hours | 48 hours |
|---|---|---|---|---|---|---|---|---|
| DoE2-1 | 50 | Acetate | 5.2 | Trehalose dihydrate (200 mM) | 0 | 5.2 | 5.2 | 5.2 |
| DoE2-2 | 50 | Acetate | 5.2 | Trehalose dihydrate (200 mM) | 0.5 | 5.2 | 5.3 | 5.3 |
| DoE2-3 | 50 | Acetate | 5.2 | Trehalose dihydrate (200 mM) | 1 | 5.2 | 5.3 | 5.3 |

DoE2 screening: pH (mechanical shaking)

2.11 Turbidity with Mechanical Stress (Nephelometry)

Figure 12:
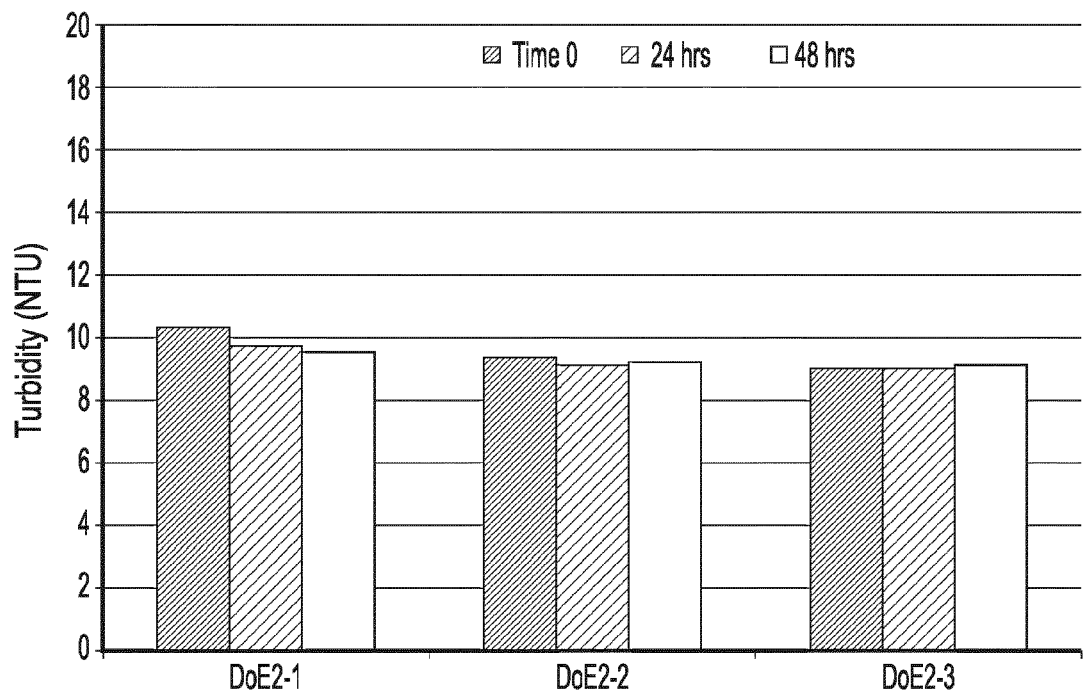
FIG. 12 is a bar chart showing the turbidity, as determined by Nephelometry, of the DoE2 formulations (of Example 2) at an arbitrary start point (blue bars, time=0) and after both 24 hours (red bars) and 48 hours (green bars) of the formulation(s) being mechanically agitated (shaking).

FIG. 12 is a bar chart showing the turbidity, as determined by Nephelometry, of the DoE2 formulations (of Example 2) at an arbitrary start point (blue bars, time=0) and after both 24 hours (red bars) and 48 hours (green bars) of the formulation(s) being mechanically agitated (shaking). No changes were observed.

2.12 Aggregates with Light Stress (SE-HPLC)

Figure 13:
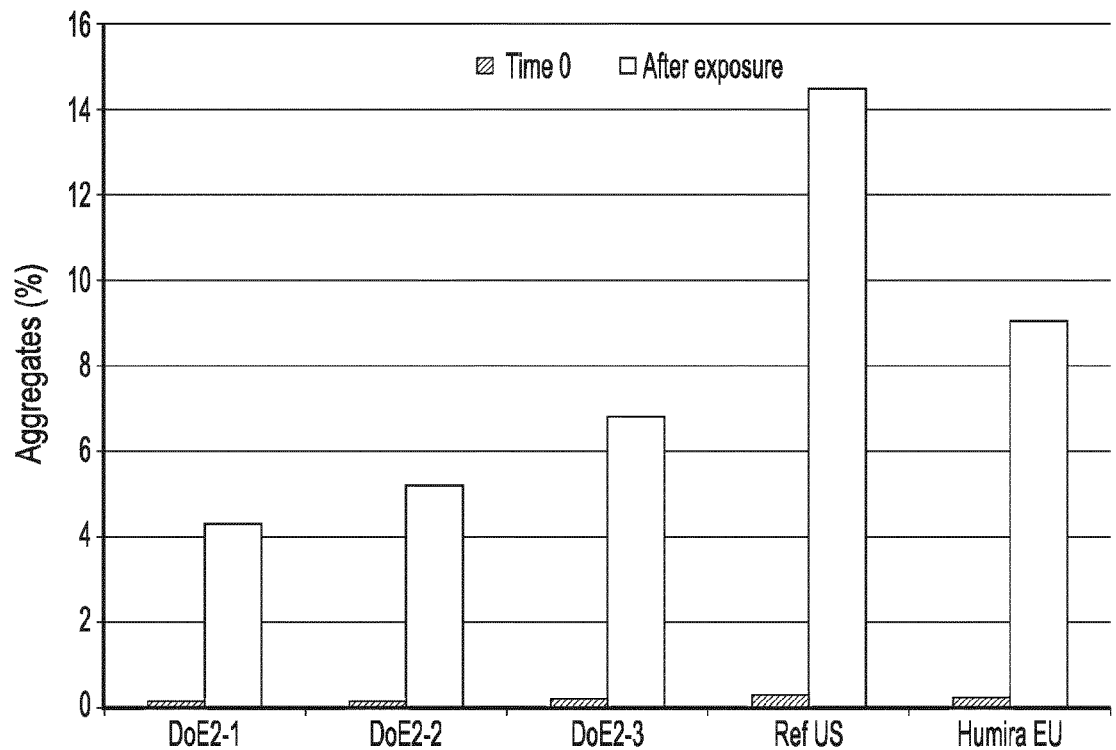
FIG. 13 is a bar chart showing the % aggregation, as determined by SE-HPLC, of the DoE2 formulations (of Example 2), along with reference standards (representing comparator HUMIRA® formulations), before exposure to light (blue bars, time=0) and after 7-hour light exposure at 765 W/m$^2$ (red bars).

FIG. 13 is a bar chart showing the % aggregation, as determined by SE-HPLC, of the DoE2 formulations (of Example 2), along with reference standards (representing comparator HUMIRA® formulations), before exposure to light (blue bars, time=0) and after 7-hour light exposure at 765 W/m² (red bars).

Comparisons were also made with Humira samples (from US and EU) treated at the same conditions. In the RMP, aggregation increases up to 9-15% upon light exposure (at time 0 aggregates are lower than 1%). All the DoE2 formulations present lower or comparable increases and therefore better/similar resistance to thermal stress. More in detail:

Formulations in acetate buffer: 4.3 4 6.8% total aggregates upon light exposure 2.13 Fragmentation with Light Stress (Bioanalyzer)

Figure 14:
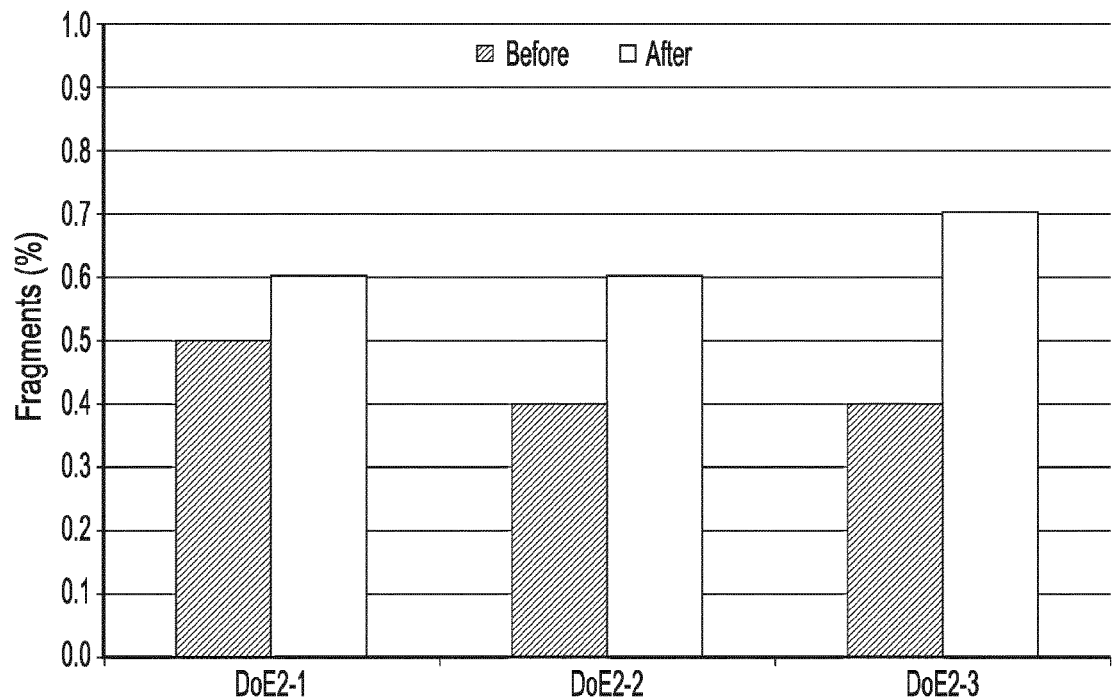
FIG. 14 is a bar chart showing the % fragmentation, as determined by a Bioanalyzer, of the DoE2 formulations (of Example 2) before exposure to light (blue bars, time=0) and after 7-hour light exposure at 765 W/m$^2$ (red bars).

FIG. 14 is a bar chart showing the % fragmentation, as determined by a Bioanalyzer, of the DoE2 formulations (of Example 2), along with reference standards (representing comparator HUMIRA® formulations), before exposure to light (blue bars, time=0) and after 7-hour light exposure at 765 W/m² (red bars).

Figure 16:
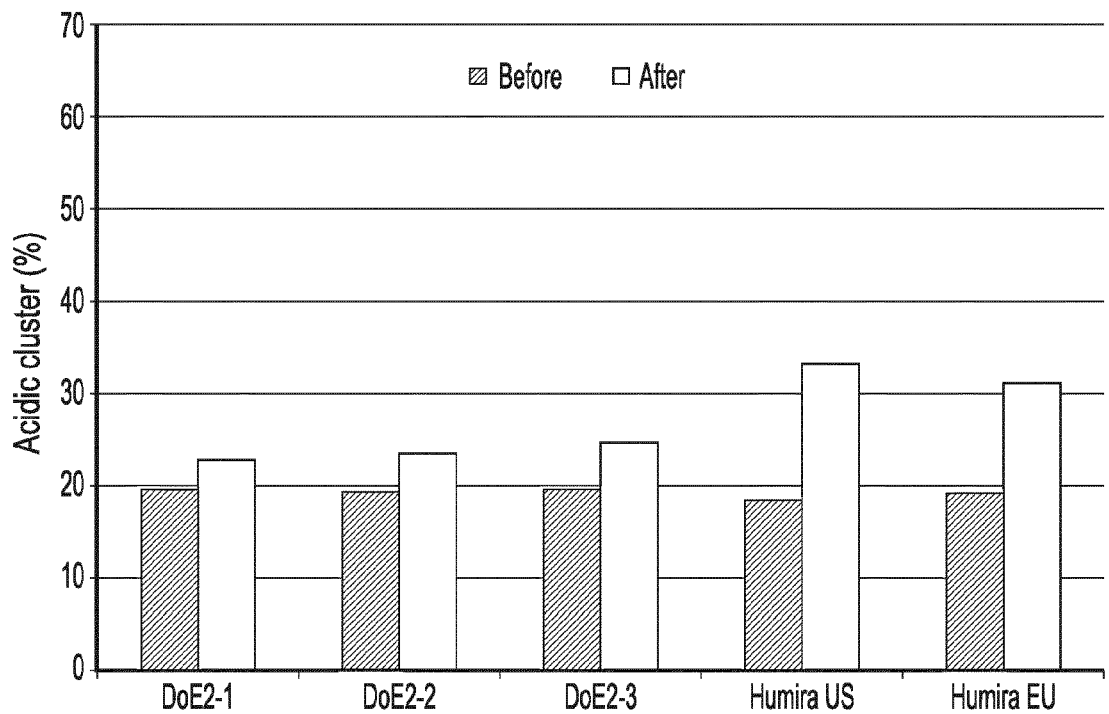
FIG. 16 is a bar chart showing the acid cluster peak(s) isoforms profile, as determined by iCE280 analysis, of the DoE2 formulations (of Example 2), along with reference standards (representing comparator HUMIRA® formulations), before exposure to light (blue bars, time=0) and after 7-hour light exposure at 765 W/m$^2$ (red bars).

FIG. 16 is a bar chart showing the acid cluster peak(s) isoforms profile, as determined by iCE280 analysis, of the DoE2 formulations (of Example 2), along with reference standards (representing comparator HUMIRA® formulations), before exposure to light (blue bars, time=0) and after 7-hour light exposure at 765 W/m² (red bars).

In the Humira RMP, the light exposure determines significant effects: most relevantly, decreases in main peak abundance (around −9%) and concurrent increase in acidic cluster (up to +15%), related to photooxidation phenomena, are observed.

Acetate formulas can considerably improve the resistance of the protein to degradation phenomena: decreases in main peak abundance are around −3.5% or lower, increases in acidic cluster scored a maximum of +4%.

2.15 Turbidity with Light Stress (Nephelometry)

Figure 17:
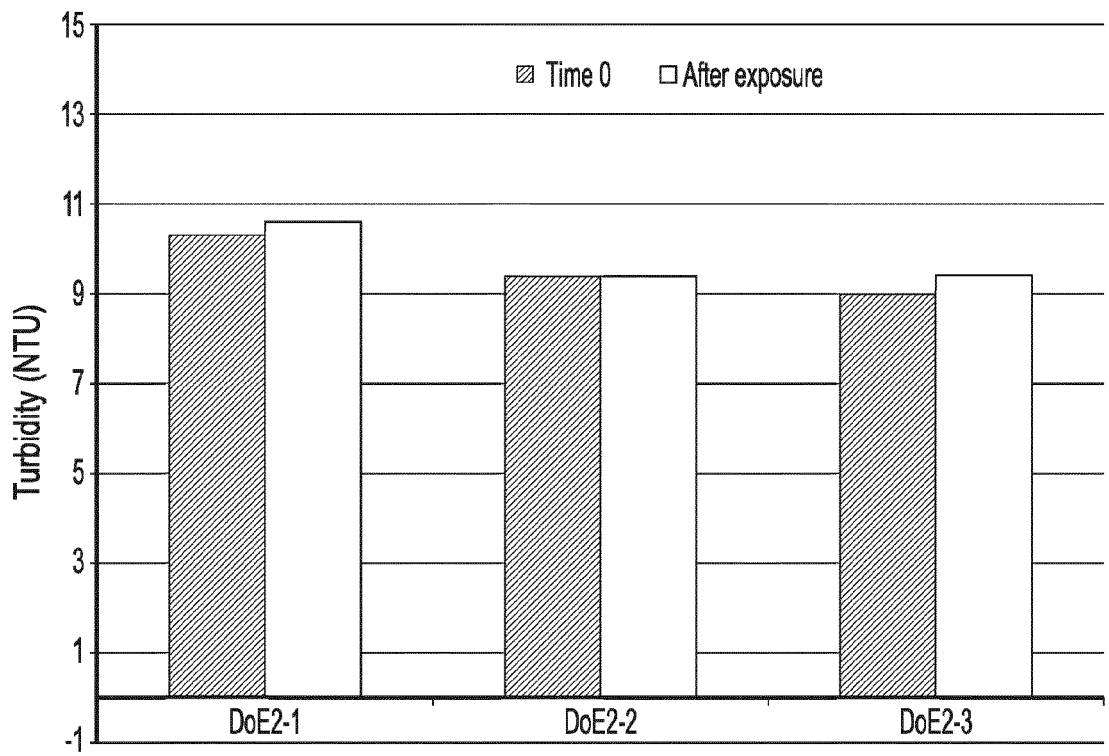
FIG. 17 is a bar chart showing the turbidity, as determined by Nephelometry, of the DoE2 formulations (of Example 2) before exposure to light (blue bars, time=0) and after 7-hour light exposure at 765 W/m$^2$ (red bars).

FIG. 17 is a bar chart showing the turbidity, as determined by Nephelometry, of the DoE2 formulations (of Example 2) before exposure to light (blue bars, time=0) and after 7-hour light exposure at 765 W/m² (red bars). Essentially no changes were observed.

2.16 pH Screen with Light Stress

The variation in pH of the DoE2 formulations (of Example 2), over a period of time during which the formulations are exposed for 7-hours to light at 765 W/m², is shown in Table 18. No changes where observed.

TABLE 18

DoE2 screening: pH (light exposure)

| Form # | Salt (NaCl) concentration (mM) | Buffer type (10 mM) | pH | Stabilizer | Surfactant (Polysorbate 80) concentration (mg/mL) | Time 0 | After exposure |
|---|---|---|---|---|---|---|---|
| DoE2-1 | 50 | Acetate | 5.2 | Trehalose dihydrate (200 mM) | 0 | 5.2 | 5.2 |
| DoE2-2 | 50 | Acetate | 5.2 | Trehalose dihydrate (200 mM) | 0.5 | 5.2 | 5.3 |
| DoE2-3 | 50 | Acetate | 5.2 | Trehalose dihydrate (200 mM) | 1 | 5.2 | 5.3 |

Minimal increases were highlighted (+0.3% at most, after exposure). All fragmentation amounts are well below 1% after 7-hour exposure (FIG. 14).

2.14 Isoforms Profile with Light Stress (iCE2280)

Figure 15:
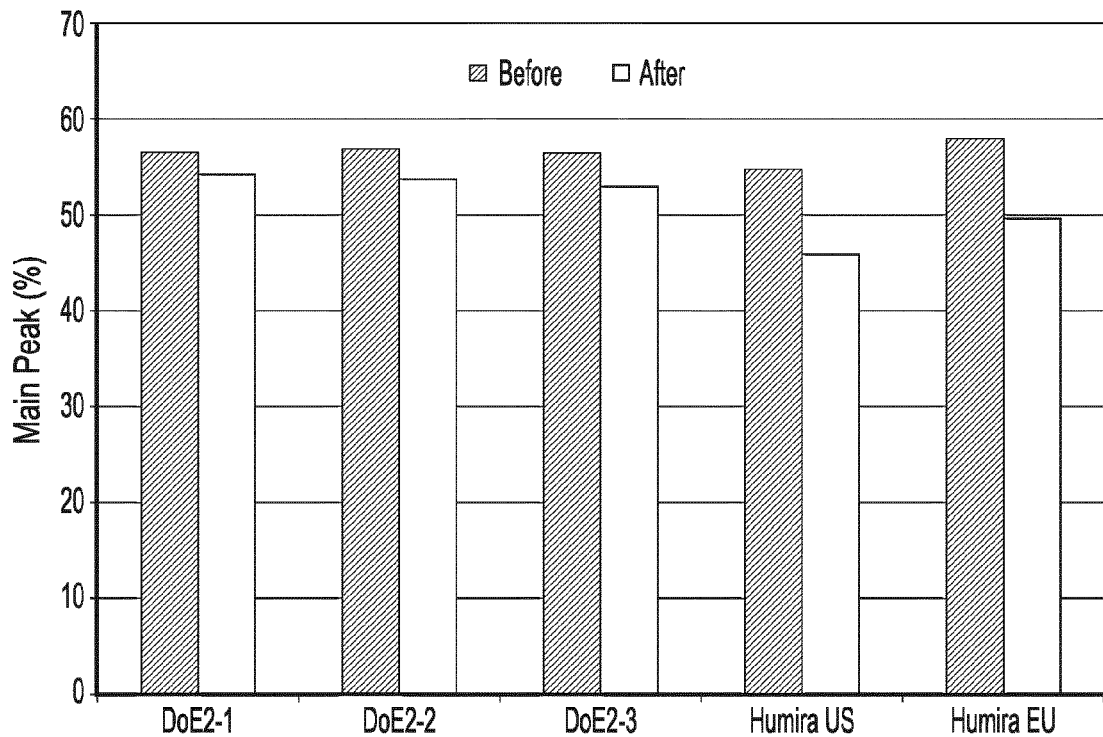
FIG. 15 is a bar chart showing the main peak isoforms profile, as determined by iCE280 analysis, of the DoE2 formulations (of Example 2), along with reference standards (representing comparator HUMIRA® formulations), before exposure to light (blue bars, time=0) and after 7-hour light exposure at 765 W/m$^2$ (red bars).

FIG. 15 is a bar chart showing the main peak isoforms profile, as determined by iCE280 analysis, of the DoE2 formulations (of Example 2), along with reference standards (representing comparator HUMIRA® formulations), before exposure to light (blue bars, time=0) and after 7-hour light exposure at 765 W/m² (red bars).

2.17 Effect of Surfactant on Freeze-Thawing Cycles

Isoforms profiles, aggregates and sub-visible particles of the three DoE2 formulations have been determined before and after five freeze-thawing cycles (−80° C.→room temperature) in order to assess whether the surfactant exerts any impact.

Figure 18:
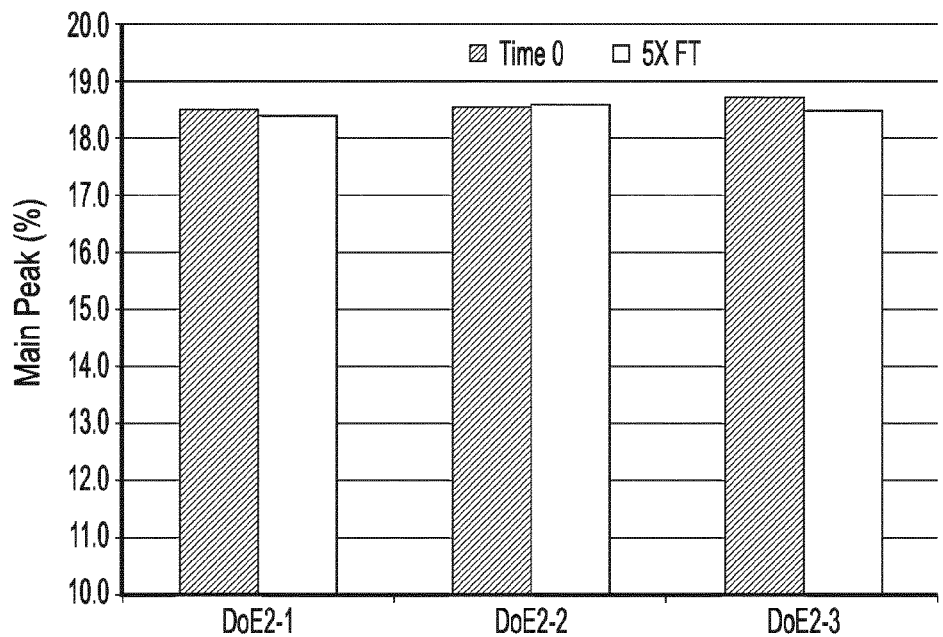
FIG. 18 is a bar chart showing the main peak isoforms profile, as determined by iCE280 analysis, of the DoE2 formulations (of Example 2) before (blue bars, time=0) and after m$^2$ (red bars) five freeze-thawing cycles (−80° C.→room temperature).

FIG. 18 is a bar chart showing the main peak isoforms profile, as determined by iCE280 analysis, of the DoE2 formulations (of Example 2) before (blue bars, time=0) and after m² (red bars) five freeze-thawing cycles (−80° C.→room temperature).

Figure 19:
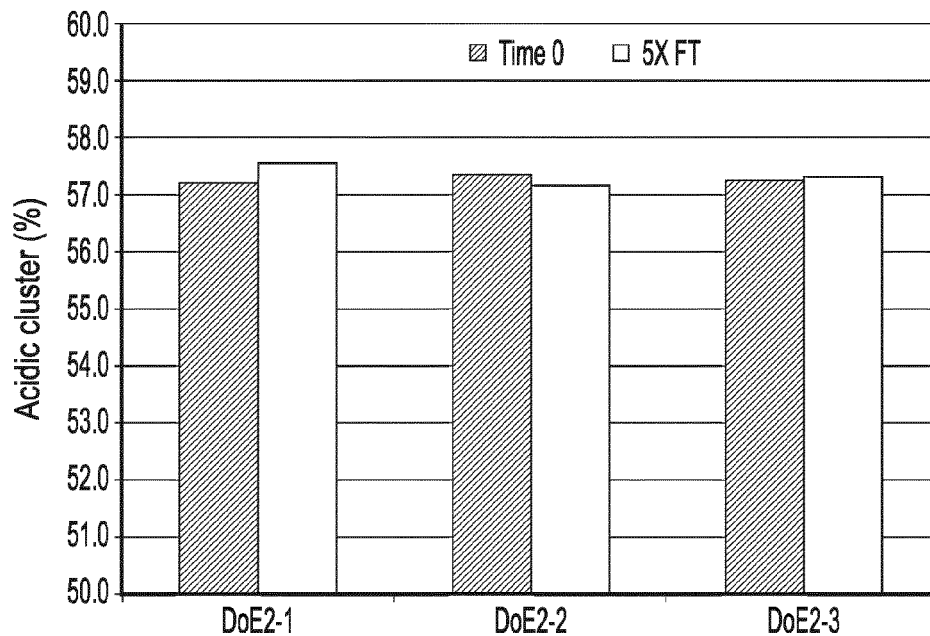
FIG. 19 is a bar chart showing the acid cluster peak(s) isoforms profile, as determined by iCE280 analysis, of the DoE2 formulations (of Example 2) before (blue bars, time=0) and after m$^2$ (red bars) five freeze-thawing cycles (−80° C.→room temperature).

FIG. 19 is a bar chart showing the acid cluster peak(s) isoforms profile, as determined by iCE280 analysis, of the DoE2 formulations (of Example 2) before (blue bars, time=0) and after m² (red bars) five freeze-thawing cycles (−80° C.→room temperature).

Figure 20:
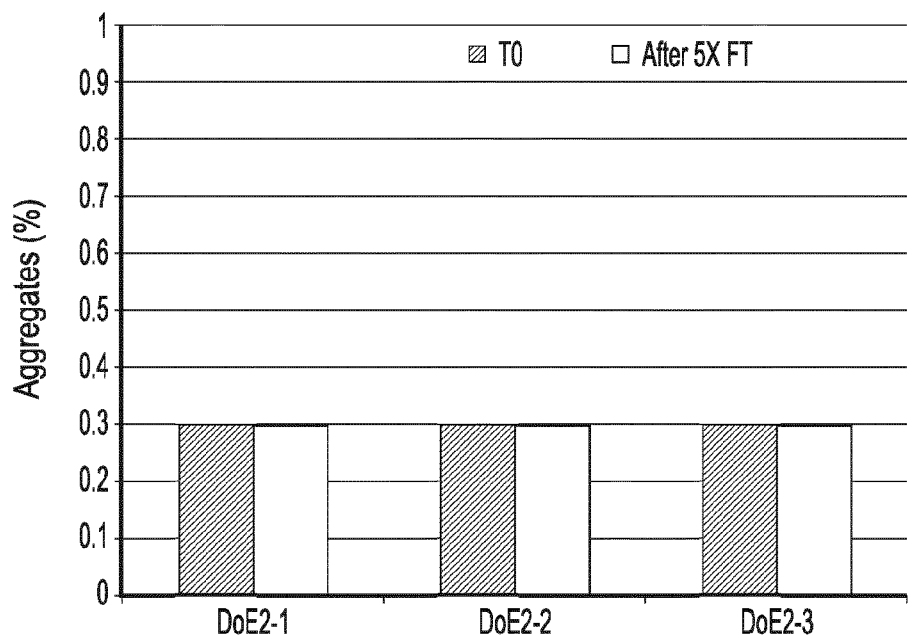
FIG. 20 is a bar chart showing the % aggregation, as determined by SE-HPLC, of the DoE2 formulations (of Example 2), along with reference standards (representing comparator HUMIRA® formulations) before (blue bars, time=0) and after m$^2$ (red bars) five freeze-thawing cycles (−80° C.→room temperature).

FIG. 20 is a bar chart showing the % aggregation, as determined by SE-HPLC, of the DoE2 formulations (of Example 2), along with reference standards (representing comparator HUMIRA® formulations) before (blue bars, time=0) and after m² (red bars) five freeze-thawing cycles (−80° C.→room temperature).

Figure 21:
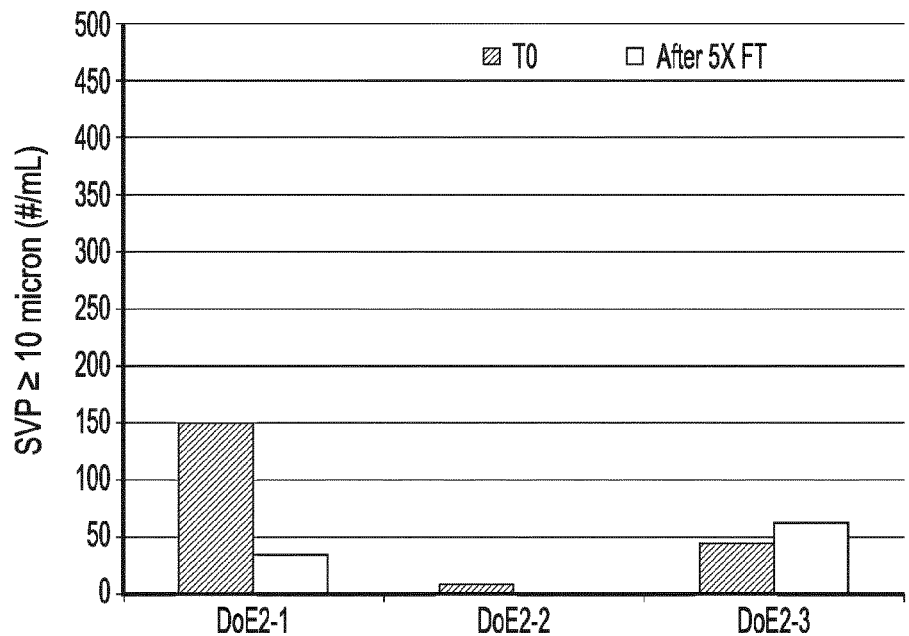
FIG. 21 is a bar chart showing the number concentration (#/mg) of sub-visible particles with a particle size less than or equal to 10 microns, as determined by sub-visible particle count analysis, of the DoE2 formulations (of Example 2) before (blue bars, time=0) and after m$^2$ (red bars) five freeze-thawing cycles (−80° C.→room temperature).

FIG. 21 is a bar chart showing the number concentration (#/mg) of sub-visible particles with a particle size less than or equal to 10 microns, as determined by sub-visible particle count analysis, of the DoE2 formulations (of Example 2) before (blue bars, time=0) and after m² (red bars) five freeze-thawing cycles (−80° C.→room temperature).

Figure 22:
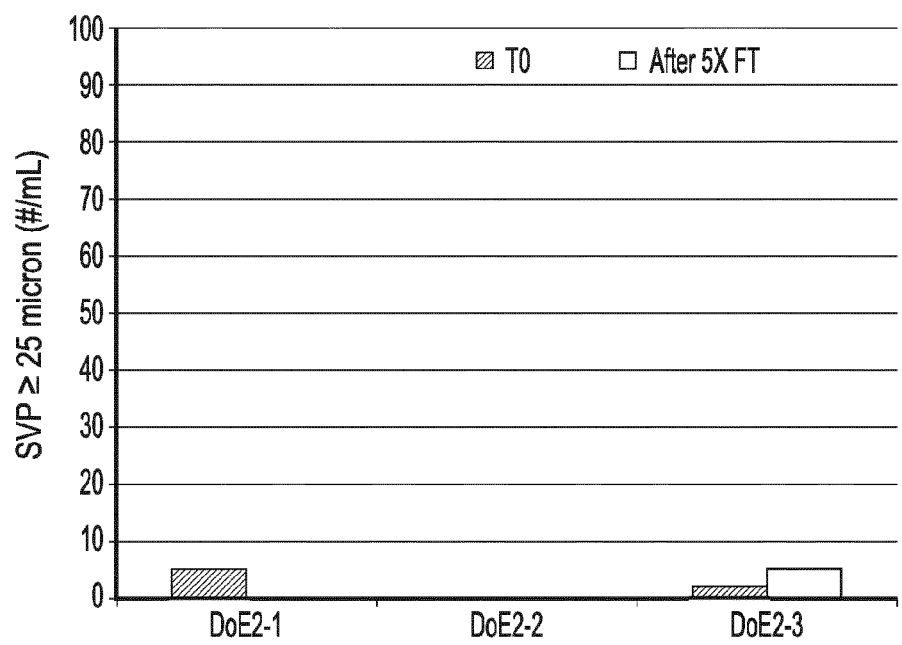
FIG. 22 is a bar chart showing the number concentration (#/mg) of sub-visible particles with a particle size less than or equal to 25 microns, as determined by sub-visible particle count analysis, of the DoE2 formulations (of Example 2) before (blue bars, time=0) and after m$^2$ (red bars) five freeze-thawing cycles (−80° C.→room temperature).

FIG. 22 is a bar chart showing the number concentration (#/mg) of sub-visible particles with a particle size less than or equal to 25 microns, as determined by sub-visible particle count analysis, of the DoE2 formulations (of Example 2) before (blue bars, time=0) and after m² (red bars) five freeze-thawing cycles (−80° C.→room temperature).

No changes in isoforms and in aggregates were observed (FIGS. 18-20) upon freeze-thawing, whilst minimal, non-critical changes (FIGS. 21-22) in sub-visible particles were highlighted, and found to be non-related to the presence of surfactant.

Conclusion of Screening Experiment 2

On the basis of the data collected, relevant to thermal, mechanical and light stress, the following conclusion can be made:

Formulations in 10 mM Sodium Acetate/Acetic Acid Buffer at pH 5.2 (DoE2-1, DoE2-2, DoE2-3):

Upon thermal stress, performances comparable or better (lower increase in aggregation) than Humira were highlighted. Beneficial impact deriving from higher Polysorbate 80 concentrations.

No change in the quality attributes upon mechanical shaking.

Improved performances with respect to Humira when subjected to continuous (7 hours) irradiation.

Based on the screening work carried out on different formulations varying in buffer/pH, stabilizer, isotonicity agent (NaCl) amount and surfactant (Polysorbate 80) level, the best composition, showing comparable or even improved characteristics with respect to Humira upon different stressing conditions (thermal, mechanical, light) has been identified as:

| Ingredient | Amount (mg/mL) |
| --- | --- |
| Adalimumab | 50 |
| Acetic Acid glacial 100% | 0.60 * |
| Trehalose dihydrate | 75.67 ** |
| Polysorbate 80 | 1.00 |
| Sodium chloride | 2.92 *** |
| WFI and sodium hydroxide | q.b. to adjust pH to 5.2 |

* corresponding to 10 mM sodium acetate/acetic acid buffer;
** corresponding to 200 mM;
*** corresponding to 50 mM Such formulations can be readily incorporated within pre-filled glass syringes with 29 G ½" needles).

ABBREVIATIONS

DoE Design of experiment
DP Drug product
DS Drug substance
DSF Differential scanning fluorimetry
OD Optical density
PES Polyethersulphone
rpm rounds per minute
RT Room Temperature
SE-HPLC Size exclusion high performance liquid chromatography
SMI Summary manufacturing instructions
SOP Standard operating procedure
WI Working instruction

CLAUSES

1. A liquid pharmaceutical composition comprising:
   (a) adalimumab;
   (b) an acetate buffering agent (or acetate buffer system); and
   (c) a sugar stabiliser selected from the group including trehalose, mannitol, sucrose, maltose, lactose, xylitol, arabitol, erythritol, lactitol, maltitol, and inositol;
   wherein the composition is either (substantially or entirely) free of arginine or comprises arginine in a concentration of at most 0.1 mM.

2. The liquid pharmaceutical composition according to clause 1, wherein the composition further comprises an acid/base conjugate of the buffering agent such that together the buffering agent and its acid/base conjugate are present at a level and in a relative amount sufficient for the composition to have a pH between pH 5.0 and 5.5, wherein the acetate buffering agent is sodium acetate and the acid/base conjugate is acetic acid.

3. The liquid pharmaceutical composition according to any preceding clause, wherein the sugar stabiliser is trehalose.

4. The liquid pharmaceutical composition according to any preceding clause, wherein the composition is either (substantially or entirely) free of amino acids or comprises one or more amino acids in a (collective) concentration of at most 0.1 mM.

5. The liquid pharmaceutical composition according to clause 4, wherein the composition is free of amino acids.

6. The liquid pharmaceutical composition according to any preceding clause, wherein the composition is either (substantially or entirely) free of surfactants, with the optional exception of polysorbate 80, or comprises one or more surfactants (optionally excluding polysorbate 80) in a (collective) concentration of at most 0.001 mM.

7. The liquid pharmaceutical composition according to any preceding clause, wherein the composition is (substantially or entirely) free of polysorbate 20.

8. The liquid pharmaceutical composition according to any preceding clause, wherein the composition is either (substantially or entirely) free of phosphate buffering agents or comprises a phosphate buffer system in a concentration of at most 0.1 mM.

9. The liquid pharmaceutical composition according to any preceding clause, further comprising a tonicifier selected from sodium chloride, potassium chloride, magnesium chloride, or calcium chloride.

10. The liquid pharmaceutical composition according to any preceding clause, further comprising polysorbate 80.

11. The liquid pharmaceutical composition according to any preceding clause, wherein the osmolality of the composition is between 220 and 400 mOsm/kg.

12. The liquid pharmaceutical composition according to any preceding clause, wherein the protein unfolding temperature of adalimumab in the liquid pharmaceutical composition is greater than or equal to 70° C.

13. The liquid pharmaceutical composition according to any preceding clause, wherein the composition comprises adalimumab, acetate buffering species, and trehalose in a weight ratio of 25-75:0.12-3.0:15-140 respectively.

14. The liquid pharmaceutical composition according to any preceding clause, wherein the composition comprises adalimumab, acetate buffering species, trehalose, and sodium chloride in a weight ratio of 45-55:0.30-0.84:65-72:2.7-3.1 respectively.

15. The liquid pharmaceutical composition according to any preceding clause, wherein the composition comprises:
- 45 to about 55 mg/ml adalimumab;
- 5 to 14 mM sodium acetate/acetic acid buffer system;
- 190 to 210 mM trehalose;
- 40 to 60 mM sodium chloride;
- 0.9 mg/mL and 1.1 mg/mL polysorbate 80; and
- water (for injection);
- wherein the composition:
  - has a pH between 5.1 and 5.3;
  - is free of arginine or comprises arginine in a concentration of at most 0.001 mM;
  - is free of amino acids or comprises one or more amino acids in a (collective) concentration of at most 0.001 mM.
  - is free of surfactants with the exception of polysorbate 80 or comprises one or more of said surfactants (excluding polysorbate 80) in a (collective) concentration of at most 0.0001 mM; and/or
  - is free of phosphate buffering agents (e.g. sodium dihydrogen phosphate, disodium hydrogen phosphate) or comprises a phosphate buffer system in a concentration of at most 0.001 mM.

16. A drug delivery device comprising a liquid pharmaceutical composition according to any preceding clause.

17. A liquid pharmaceutical composition according to any of clauses 1 to 15 for use in the treatment of rheumatoid arthritis, psoriatic arthritis, ankylosing spondylitis, Crohn's disease, ulcerative colitis, moderate to severe chronic psoriasis and/or juvenile idiopathic arthritis.

The invention claimed is:

1. A liquid pharmaceutical composition consisting of:
   i) adalimumab;
   ii) an acetate buffer system in a molar ratio of buffer system to adalimumab of from 5:1 to 29:1;
   iii) a stabiliser, which is an amino acid other than arginine, lysine, aspartic acid, and histidine, in a molar ratio of stabiliser to adalimumab from 290:1 to 576:1;
   iv) a surfactant, which is polysorbate 80, in a molar ratio of surfactant to adalimumab of from 0.3:1 to 3:1; and
   v) water;
   wherein the molar ratio of surfactant to buffer system is from 1:100 to 1:10; and
   wherein the composition:
   is free of arginine, lysine, aspartic acid, and histidine;
   has a pH between 5.1 and 5.3; and
   has an osmolality between 260 and 320 mOsm/kg.

2. The liquid pharmaceutical composition of claim 1, wherein the stabiliser is glycine.

3. The liquid pharmaceutical composition of claim 1, wherein the stabiliser is present in a molar ratio of stabiliser to adalimumab of from about 290:1 to about 430:1.

4. The liquid pharmaceutical composition of claim 3, wherein the stabiliser is glycine.

5. A drug delivery device comprising the liquid pharmaceutical composition of claim 1.

6. A method of treating rheumatoid arthritis, psoriatic arthritis, ankylosing spondylitis, Crohn's disease, ulcerative colitis, moderate to severe chronic psoriasis and/or juvenile idiopathic arthritis in a patient in need of such treatment, said method comprising administering to said patient a therapeutically effective amount of the liquid pharmaceutical composition of claim 1.

7. The method of claim 6, wherein the method is for treating psoriatic arthritis, ankylosing spondylitis, Crohn's disease, ulcerative colitis, moderate to severe chronic psoriasis and/or juvenile idiopathic arthritis in a patient in need of such treatment.

8. The liquid pharmaceutical composition of claim 1, wherein the acetate buffer system is present in a molar ratio of buffer system to adalimumab of from 5:1 to 14:1.

9. The liquid pharmaceutical composition of claim 1, wherein the acetate buffer system is present in a molar ratio of buffer system to adalimumab of about 14:1.

10. The liquid pharmaceutical composition of claim 1, wherein the composition has an osmolality between 260 and 280 mOsm/kg.

11. The liquid pharmaceutical composition of claim 1, wherein the surfactant is present in a molar ratio of surfactant to adalimumab of at most 2.1:1.

* * * * *